United States Patent
Tuskan et al.

(10) Patent No.: US 10,017,770 B2
(45) Date of Patent: Jul. 10, 2018

(54) TNT CLONING SYSTEM

(71) Applicant: UT-Battelle, LLC, Oak Ridge, TN (US)

(72) Inventors: Gerald A. Tuskan, Oak Ridge, TN (US); Xiaohan Yang, Knoxville, TN (US); Henrique Cestari De Paoli, Oak Ridge, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 0 days.

(21) Appl. No.: 14/789,112

(22) Filed: Jul. 1, 2015

(65) Prior Publication Data
US 2016/0002644 A1 Jan. 7, 2016

Related U.S. Application Data

(60) Provisional application No. 62/020,510, filed on Jul. 3, 2014, provisional application No. 62/020,496, filed on Jul. 3, 2014.

(51) Int. Cl.
*C12N 15/66* (2006.01)
*C12N 15/64* (2006.01)

(52) U.S. Cl.
CPC ............ *C12N 15/64* (2013.01); *C12N 15/66* (2013.01)

(58) Field of Classification Search
None
See application file for complete search history.

(56) References Cited

U.S. PATENT DOCUMENTS

| 9,115,352 B2 * | 8/2015 | Van den Brulle | C12N 15/10 |
| 9,206,433 B2 * | 12/2015 | Minshull | C12N 15/64 |
| 2004/0198687 A1 * | 10/2004 | Rozema | C12N 15/88 514/44 R |

OTHER PUBLICATIONS

Gibson (Methods in Enzymology, 2011, vol. 498, Chapter 15).*
Boavida, L.C., et al., "Arabidopsis Tetraspanins are Confined to Discrete Expression Domains and Cell Types in Reproductive Tissues and Form Homo- and Heterodimers When Expressed in Yeast" Plant physiology (2013) pp. 696-712, vol. 163.
Brunet, E. et al., "Intercalator conjugates of pyrimidine locked nucleic acid-modified triplex-forming oligonucleotides: improving DNA binding properties and reaching cellular activities" Nucleic acids research (2005) pp. 4223-4234, vol. 33, No. 13.
DePaoli, H.C. et al., "Synthetic biology as it relates to CAM photosynthesis: challenges and opportunities" Journal of experimental botany (Feb. 2014) pp. 3381-3393, vol. 65.
Donnelly, M.L. et al., "The 'cleavage' activities of foot-and-mouth disease virus 2A site-directed mutants and naturally occurring '2A-like' Sequences" The Journal of general virology (2001) pp. 1013-1025, vol. 82.
Engler, C., et al., "A One Pot, One Step, Precision Cloning Method with High Throughput Capability" PloS one (Nov. 2008) pp. e3647-1-e3647-7, vol. 3, No. 11.
Francois, I.E. et al., "Transgenic Expression in Arabidopsis of a Polyprotein Construct Leading to Production of Two Different Antimicrobial Proteins" Plant physiology (Apr. 2002) pp. 1346-1358, vol. 128.
Gibson, D.G. et al., "Enzymatic assembly of DNA molecules up to several hundred kilobases" Nature methods (May 2009) pp. 343-345, vol. 6, No. 5.
Guye, P., et al., "Rapid, modular and reliable construction of complex mammalian gene circuits" Nucleic acids research (2013) pp. 1-6, vol. 41, e156.
Hajdukiewicz, P., et al., "The small, versatile pPZP family of Agrobacterium binary vectors for plant transformation" Plant molecular biology (1994) pp. 989-994, vol. 25.
Hillson, N.J., et al., "j5 DNA Assembly Design Automation Software" ACS synthetic biology (2012) pp. 14-21, vol. 1.
Kim, J.H. et al., "High Cleavage Efficiency of a 2A Peptide Derived from Porcine Teschovirus-1 in Human Cell Lines, Zebrafish and Mice" PLoS One (Apr. 2011) pp. e18556-1-e18556-8, vol. 6, No. 4.
Knight, T., "Idempotent Vector Design for Standard Assembly of Biobricks" MIT Artificial Intelligence Laboratory (2003) pp. 1-11.
Litcofsky, K.D., et al., "Iterative plug-and-play methodology for constructing and modifying synthetic gene networks" Nature methods (Nov. 2012) pp. 1077-1080, vol. 9, No. 11.
McKenzie, G.J. et al., "Fast, easy and efficient: site-specific insertion of transgenes into Enterobacterial chromosomes using Tn7 without need for selection of the insertion event" BMC Microbiology (2006) pp. 1-7, vol. 6, No. 39.
Nikolova, E.N., et al., "Characterizing the Protonation State of Cytosine in Transient G•C Hoogsteen Base Pairs in Duplex DNA" Journal of the American Chemical Society (May 2013) pp. 6766-6769, vol. 135, No. 18.
Praseuth, D. et al., "Triple helix formation and the antigene strategy for sequence-specific control of gene expression" Biochimica et biophysica acta (1999) pp. 181-206, vol. 1489.
Roberts, R.J., et al., "REBASE—a database for DNA restriction and modification: enzymes, genes and genomes" Nucleic acids research (2015) pp. D298-D299, vol. 43.
Sarrion-Perdigones, A. et al., "GoldenBraid 2.0: A Comprehensive DNA Assembly Framework for Plant Synthetic Biology" Plant physiology (Jul. 2013) pp. 1618-1631, vol. 162.
Sarrion-Perdigones, A. et al., "GoldenBraid: An Iterative Cloning System for Standardized Assembly of Reusable Genetic Modules" PloS one (Jul. 2011) pp. e21622-1-e21622-11, vol. 6, No. 7.
Slootweg, E. et al., "Nucleocytoplasmic Distribution is Required for Activation of Resistance by the Potato NB-LRR Receptor Rx1 and is Balanced by its Functional Domains" The Plant cell (Dec. 2010) pp. 4195-4215, vol. 22.
Walhout, A.J. et al., "Protein Interaction Mapping in C. elegans Using Proteins Involved in Vulval Development" Science (Jan. 2000) pp. 116-122, vol. 287.
Ward, B., Type IIS restriction enzyme footprinting I. Measurement of a triple helix dissociation constant with Eco57I at 25°C"Nucleic acids research (1996) pp. 2435-2440, vol. 24, No. 12.

* cited by examiner

*Primary Examiner* — Catherine S Hibbert
(74) *Attorney, Agent, or Firm* — Scully Scott Murphy & Presser

(57) ABSTRACT

Disclosed herein are vectors and components for a nucleic acid cloning system, and methods of use of the vectors and components in cloning nucleic acid fragments of interest. The cloning system includes two families of destination vectors which can be used in alternating form to systematically combine nucleic acid fragments of interest.

10 Claims, 30 Drawing Sheets
(26 of 30 Drawing Sheet(s) Filed in Color)

FIG. 16A

TNT CLONING SYSTEM

CROSS-REFERENCE TO RELATED APPLICATIONS

This application claims priority to U.S. Provisional Application No. 62/020,496, filed Jul. 3, 2014, and U.S. Provisional Application No. 62/020,510, filed Jul. 3, 2014, each of which is incorporated herein in its entirety.

STATEMENT REGARDING FEDERALLY SPONSORED RESEARCH OR DEVELOPMENT

This invention was made with government support under Contract No. DE-AC05-000R22725 awarded by the US Department of Energy. The government has certain rights in the invention.

INCORPORATION BY REFERENCE OF SEQUENCE LISTING

The Sequence Listing in the ASCII text file, named as 32028_SEQ_3.txt of 73 KB, created on Mar. 8, 2017, and submitted to the United States Patent and Trademark Office via EFS-Web, is incorporated herein by reference.

BACKGROUND OF THE DISCLOSURE

Current cloning methods include sequence homology methods such as isothermal assembly (Gibson, D. G. et al., *Nature methods* 6, 343-345 (2009)), recombination (Walhout, A. J. et al., *Science* 287, 116-122 (2000)) or design of sequence signatures left by restriction digestion followed by ligation of DNA, such as BioBricks (described in 2003 by Knight, T. from the MIT Artificial Intelligence Laboratory) and GoldenGate (Engler, C., et al., *PloS one* 3, e3647 (2008)) (for a review, see, DePaoli, H. C., et al., *Journal of experimental botany* 65, 3381-3393 (2014)). Each method has its disadvantages, and so far, a platform capable of uniting flexibility, fidelity, efficiency and universality for unbiased handling of multiple DNA segments has yet to be developed. The homology-based methods require sequence overlap, which limit the type and order of fragment cloning. Some strategies, such as designing adaptors that allow for sequences to be part of alternate libraries, only partially surpasses this limitation and in the process create scars and intermediary products are often incompatible with future assembling units (Guye, P., et al., *Nucleic acids research* 41, e156 (2013)). Moreover, PCR-based methods are error prone, and restriction enzyme-based methods require specific recognition sequences to be present at specific sites which will in turn limit the number of fragments based on the number of restriction sites that can be used (Litcofsky, K. D., et al., *Nature methods* 9, 1077-1080 (2012); Knight (2003).

One way to overcome such limitation is to use restriction enzymes that recognize a sequence outside the fragment of interest (FOI). If two sets of such enzymes are used in an alternating pattern, the same enzymes can be reused forming a 'cloning loop'. The most recent use of such principles was revealed in the GoldenBraid (GB) method, which introduced the term endless assembly (Sarrion-Perdigones, A. et al., *Plant physiology* 162, 1618-1631 (2013), Sarrion-Perdigones, A. et al., *PloS one* 6, e21622 (2011)). Upon creation of different gene collections, carrying a user-defined 4 nucleotide signature, the GB method provides an alternative to homology-based methods by building some transcriptional units and joining them together in vitro. However, the GB method requires multiple libraries, uses linkers/adaptors to produce functional parts, involves software to assist the construct design (Hillson, N. J., et al., *ACS synthetic biology* 1, 14-21 (2012)) and leaves non-standard signatures, making it difficult to establish a common platform for different laboratories.

In addition to the above problems, restriction enzyme-based methods often obligate a mutation step to be performed within the FOIs at the enzyme recognition sequence in order to properly manipulate the DNA segment, a process called domestication. The prescribed need to use overlap from homology-based methods and the domestication from restriction enzymes-based methods strongly restricts or even excludes several FOI (for example, regulatory regions) in multigene assemblies. Therefore, to properly support synthetic biology and genetic circuit engineering, within the framework of screening and analyzing many alternative and sharable network designs experimentally, these hurdles at the cloning level must be overcome.

BRIEF SUMMARY OF THE DISCLOSURE

Disclosed herein is a new cloning system for virtually any DNA fragments to be quickly, reliably and flexibly clustered and shared. In some aspects, the disclosed cloning system provides two families of double-stranded vectors, and methods of cloning that involve potentially infinite rounds of cloning between vectors of the first family and vectors of the second family, such that multiple genetic elements can be combined together to form a final vector with many combined genetic components.

The first and second vector families share the same first type IIS restriction enzyme site, the same second type IIS restriction enzyme site, and the same three or more "signature elements", which are pre-selected 3-nucleotide signature elements that allow cleavage and release of nucleic acid fragments of interest from one family of vectors, and ligation and insertion into another vector or another family of vectors.

The first family of destination vectors includes at least two first family destination vectors 1A and 2. Each of the destination vectors in the first family includes the same first type IIS restriction enzyme site, the same second type IIS restriction enzyme site, and a selectable marker gene, and wherein each destination vector comprises at least three different signature elements selected from four 3-nucleotide signature elements.

The cloning region of each vector in the first family of vectors is arranged, from 5' to 3' on the forward/sense strand of each vector, as follows: (a) the forward sequence of the first type IIS restriction enzyme site; (b) the forward sequence of the first signature element; (c) the reverse complement sequence of the second type IIS restriction enzyme site, with the restriction enzyme cleavage site at the 3' end of the first signature element; (d) the selectable marker gene; (e) the forward sequence of the second type IIS restriction enzyme site, with the restriction enzyme cleavage site at the 5' end of the second signature element; (f) the forward sequence of a second signature element; and (g) the reverse complement sequence of the first type IIS restriction enzyme site.

In addition to the above arrangement, the first family destination vectors 1A and 2 are further organized as follows. The first family destination vector 1A further includes, from 5' to 3' on the sense strand, the forward sequence of a third signature element between (f) the forward sequence of the second signature element and (g) the reverse complement sequence of the first type IIS restriction enzyme site. The first family destination vector 2 further includes, from 5' to 3' on the sense strand, the forward sequence of the third signature element between (a) the forward sequence of the first type IIS restriction enzyme site and (b) the forward sequence of the first signature element.

The first family of destination vectors can further include first family destination vectors B and C. Destination vector B includes, from 5' to 3' in the sense strand: the forward sequence of the third signature element between (a) the forward sequence of the first type IIS restriction enzyme site and (b) the forward sequence of the first signature element. Vector B further includes the forward sequence of a fourth signature element between (f) the forward sequence of the second signature element and (g) the reverse complement sequence of the first type IIS restriction enzyme site. Destination vector C further includes, from 5' to 3' on the sense strand, the forward sequence of the fourth signature element between (a) the forward sequence of the first type IIS restriction enzyme site and (b) the forward sequence of the first signature element.

Further provided is a second family of double-stranded destination vectors including at least one second family destination vector 1A, each vector in the second family having the same first and second type IIS restriction enzyme sites as in the first family of destination vectors, and at least three signature elements selected from four 3-nucleotide signature elements which are the same signature elements as in the first family of destination vectors, and further including a selectable marker gene that can be the same or different from the selectable marker gene of the first family destination vectors.

Each second family destination vector includes, from 5' to 3' in the sense strand: (a) the forward sequence of the second type IIS restriction enzyme site; (b) the forward sequence of the first signature element; (c) the reverse complement sequence of the first type IIS restriction enzyme site; (d) the selectable marker gene; (e) the forward sequence of the first type IIS restriction enzyme site; (f) the forward sequence of said second signature element; and (g) the reverse complement sequence of the second type IIS restriction enzyme site, with the restriction enzyme cleavage site at the 3' end of the third signature element.

The second family destination vector 1A further includes, from 5' to 3' on the sense strand, the forward sequence of a third signature element between (f) the forward sequence of the second signature element and (g) the reverse complement sequence of the second type IIS restriction enzyme site.

The second family of destination vectors can also include, in addition to second family destination vector 1A, a second family destination vector 2 which further includes, from 5' to 3' on the sense strand, the forward sequence of the third signature element between (a) the forward sequence of the second type IIS restriction enzyme site and (b) the forward sequence of the first signature element.

The second family of destination vectors can also include, in addition to second family destination vector 1A, second family destination vectors B and C. Destination vector B further includes, from 5' to 3' on the sense strand, the forward sequence of the third signature element between (a) the forward sequence of the second type IIS restriction enzyme site and (b) the forward sequence of the first signature element; and the forward sequence of a fourth signature element between (f) the forward sequence of the second signature element and (g) the reverse complement sequence of the second type IIS restriction enzyme site. Destination vector C further includes, from 5' to 3' on the sense strand, the forward sequence of said fourth signature element between (a) the forward sequence of the second type IIS restriction enzyme site and (b) the forward sequence of the first signature element.

The first and second type IIS restriction enzyme sites can be selected from restriction enzyme recognition sites for *Enterobacter aerogenes* I (EarI), *Lysobacter gummosus* RFLI (LguI), *Bacillus coagulans* 5I (Bco5I), *Bacillus coagulans* 116I (Bco116I), *Bacillus coagulans* KI (BcoKI), *Bacillus stearothermophilus* XI (BsaXI), *Bacillus stearothermophilus* ZI (BseZI), *Bacillus stearothermophilus* 6I (Bst6I), *Bacillus stearothermophilus* IMI (BssIMI), *Bacillus sphaericus* QI (BspQI), *Bacillus stearothermophilus* IMI (BssIMI), *Bacillus subtilis* 6I (Bsu6I), *Bacillus atrophaeus* HI (BatHI), *Enterobacter amnigenus* RFL1104 (Eam1104I), *Klebsiella pneumoniae* NIH30III (KpnNIH30III), *Planococcus citreus* SI (PciSI), *Rhizobium leguminosarum* AI (RleAI), *Saccharopolyspora* species I (SapI), *Staphylococcus intermedius* I (SimI), and *Vibrio parahaemolyticus* K32I (VpaK32I). In one embodiment, the first and second type IIS restriction enzyme sites are selected from *Enterobacter aerogenes* I (EarI) and *Lysobacter gummosus* RFLI (LguI) restriction enzyme sites. In a further embodiment, the first type IIS restriction enzyme site is an EarI site, and the second type IIS restriction enzyme site is an LguI site. In another embodiment, the first type IIS restriction enzyme site is an LguI site, and the second type IIS restriction enzyme site is an EarI site.

Each member of the first and second families of destination vectors may further contain a second selectable marker which is the same within each family, but which differs between the first and second families. The second selectable markers for said first and second families can be, for example, antibiotic resistance genes.

The disclosed cloning system can further include a ligation buffer which contains a polyglycol polymer, such as a block copolymer of polypropylene glycol (PPG) and polyethylene glycol (PEG). The ligation buffer can further include 20-80 mM Tris-HCl, (pH 7-8); 0.1-4.0 mM, dithiothreitol (DTT); 1-20 mM $MgCl_2$; 0.1-2.0 mM ATP; and 0.1-4.0% polyglycol polymer.

In another embodiment, the first family of destination vectors includes at least one vector for antisense expression of a nucleic acid, wherein the signature elements present in any vector for antisense expression can be present in either a forward or reverse complement orientation in the vector sequence. The vectors for antisense expression can be selected from first family destination vectors 1A-R.

First family destination vector 1A-R includes, from 5' to 3' in the sense strand: the forward sequence of the first type IIS restriction enzyme site; the forward sequence of the first signature element; the reverse complement sequence of the second signature element; the reverse complement sequence of the second type IIS restriction enzyme site; the selectable marker gene; the forward sequence of the second type IIS restriction enzyme site; the reverse complement sequence of the first signature element; the forward sequence of a third signature element; and the reverse complement sequence of the first type IIS restriction enzyme site.

First family destination vector 2-R includes, from 5' to 3' in the sense strand: the forward sequence of the first type IIS restriction enzyme site; the forward sequence of the third signature element; the reverse complement sequence of the second signature element; the reverse complement sequence of the second type IIS restriction enzyme site; the selectable marker gene; the forward sequence of the second type IIS restriction enzyme site; the reverse complement sequence of the first signature element; the forward sequence of the second signature element; and the reverse complement sequence of the first type IIS restriction enzyme site.

First family destination vector B-R includes, from 5' to 3' in the sense strand: the forward sequence of the first type IIS restriction enzyme site; the forward sequence of the third signature element; the reverse complement sequence of the second signature element; the reverse complement sequence of the second type IIS restriction enzyme site; the selectable marker gene; the forward sequence of the second type IIS restriction enzyme site; the reverse complement sequence of the first signature element; the forward sequence of the fourth signature element; and the reverse complement sequence of the first type IIS restriction enzyme site.

First family destination vector C-R includes, from 5' to 3' in the sense strand: the forward sequence of the first type IIS restriction enzyme site; the forward sequence of the fourth signature element; the reverse complement sequence of the second signature element; the reverse complement sequence of the second type IIS restriction enzyme site; the selectable marker gene; the forward sequence of the second type IIS restriction enzyme site; the reverse complement sequence of the first signature element; the forward sequence of the second signature element; and the reverse complement sequence of the first type IIS restriction enzyme site.

Further disclosed herein are methods for generating one or more vectors containing an ordered combination of a plurality of nucleic acid fragments of interest (FOIs). The methods include integrating the plurality of (i.e., at least two) FOIs separately into a plurality of first family destination vectors, with each FOI in a different first family destination vector, to produce a set of modified first family vectors, each modified vector containing an FOI; then transferring the FOI in each vector to a second family destination vector by cleaving the modified first family vectors to release the respective FOIs and ligating the released FOIs with each other and with at least one second family destination vector, such that a plurality of (i.e., at least two FOIs) are integrated into each second family destination vector, to produce one or more modified second family vectors containing an ordered combination of a plurality of FOIs. In each case, the segment of the destination vector containing the selectable marker is excised from the destination vector, and is replaced by the FOI.

This cloning cycle can be repeated, such that, for example, two or more distinct ordered combinations of FOIs in two or more modified second family destination vectors can be placed in sequential order by integrating the ordered combinations of FOIs into a new set of first family destination vectors, such that each new modified first family vector now contains two or more ordered combinations of multiple FOIs. The methods can also start with the second family of vectors as the initial destination vectors, integrate into one or more first family vectors, and so on. The methods are detailed as follows.

The disclosed methods begin with providing two or more polynucleotides, each polynucleotide including (i) an FOI; (ii) the same type IIS restriction enzyme site at each of the 5' and 3' ends, where the restriction enzyme site at each of the 5' and 3' ends can be cleaved by the same first and second type IIS restriction enzymes utilized throughout the methods; and (iii) two 3-nucleotide signature elements, wherein each polynucleotide has the same first signature element 5' of the FOI and the same second signature element 3' of the FOI, the 5' signature element being distinct from the 3' signature element, but the 5' and 3' signature elements are the same signature elements immediately flanking the selectable marker gene on both the first and second family destination vectors. The polynucleotide can be any starting vector, including but not limited to a pSTART vector, or a first or second family destination vector; or the polynucleotide can be a nucleic acid sequence that extends 5-50 nucleotides 5' and/or 3' of the FOI itself.

The methods next involve providing a first family of destination vectors including a plurality of (i.e., at least two) first family vectors (e.g., vector 1A and 2 as described previously); and providing a type IIS restriction enzyme that cleaves each first family vector at the second restriction enzyme site.

The polynucleotides, the first family vectors, the type IIS restriction enzyme, and a DNA ligase, are placed together under conditions that allow the type IIS restriction enzyme to cleave the first family destination vectors and the polynucleotides at the second restriction enzyme site—this cleavage generates a 3-nucleotide first signature element overhang on one end of each first family destination vector, and a 3-nucleotide second signature element overhang on the other end of each first family destination vector, as well as a 3-nucleotide first signature element overhang on the 5' end of each FOI (complementary to that on the destination vectors) and a 3-nucleotide second signature element overhang on the 3' end of each FOI (complementary to that on the destination vectors)—and that also allow ligation of the FOIs into a member of the first family of destination vectors. This creates a set of at least two modified first family vectors, each modified vector having one FOI substituted for the selectable marker gene.

In the next step of the methods, at least one vector (e.g., vector 1A) of a second family of destination vectors is provided, along with a type IIS restriction enzyme that cleaves each vector in the first and second families of destination vectors at the first restriction enzyme site. The modified first family destination vectors (i.e., first family destination vectors each containing a FOI) are placed together with the at least one second family destination vector such as vector 1A, the type IIS restriction enzyme that cleaves the vectors at the first restriction enzyme site, and a DNA ligase, under conditions that allow cleavage and release of the FOIs from the modified first destination vectors and cleavage of the at least one second family destination vector—this cleavage generates a 3-nucleotide first signature element overhang on one end of the second family destination vector, and a 3-nucleotide second signature element overhang on the other end of the second family destination vector, as well as a plurality of FOIs each with a 3-nucleotide overhang on the 5' end and a 3' overhang on the 3' end, and with (i) at least one FOI having a 3-nucleotide first signature element overhang on its 5' end complementary to the 3-nucleotide overhang on the second family destination vector and having a 3-nucleotide signature element overhang on its 3' end complementary to the 3 nucleotide overhang on the 5' end of another FOI, and (ii) at least a further FOI having a 3-nucleotide second signature element overhang on its 3' end complementary to the 3-nucleotide overhang on the second family destination vector and having a 3-nucleotide signature element overhang on its 5' end complementary to the 3 nucleotide overhang on the 3' end of a different FOI; and that allow ligation of a plurality of (at least two) FOIs with each other and into the at least one second family destination vector, and ligation of the FOIs to each other within the second family destination vector in an ordered arrangement, thereby generating at least one modified second family vector with an ordered combination of a plurality of nucleic acid fragments of interest.

In some embodiments, ligation of the FOIs to the second family destination vector occurs as follows: a first FOI having a first signature element on its 5' end is ligated at its 5' end to the 3' end of the second family destination vector, the second family destination vector having a complementary first signature element; and a second FOI having a second signature element on its 3' end is ligated at its 3' end to the 5' end of the second family destination vector, said second family destination vector having a complementary second signature element. Ligation of the FOIs to each other occurs at at least a third signature element, with one FOI having the third signature element on its 3' end, and another FOI having the complementary third signature element on its 5' end, such that they join.

In a specific embodiment, the first FOI, which is or can be joined at its 5' end to the 3' end of the second family destination vector, has the third signature element on its 3' end, and the second FOI, which is or can be joined at its 3' end to the 5' end of the second family destination vector, has the complementary third signature element on its 5' end, such that the first and second fragments of interest are ligated to each other through the third signature element and are joined to the second family destination vector in the ordered combination of vector-first FOI-second FOI-vector.

In a further embodiment, there are three FOIs which are ligated to each other such that, from 5' to 3', the fragments are in the order of first FOI, third FOI, and second FOI, as follows. The first fragment of interest has the third signature element on its 3' end, and the third fragment of interest has the complementary third signature element on its 5' end, so that the first and third fragments of interest are ligated to each other through the third signature element. Further, the second fragment of interest has a fourth signature element on its 5' end, and the third fragment of interest has the complementary fourth signature element on its 3' end, so that the second and third fragments of interest are ligated to each other through the fourth signature element. The first FOI is joined at its 5' end to the vector, and the second FOI is joined at its 3' end to the vector. The ordered combination is thus vector-first FOI-third FOI-second FOI-vector.

The method can further include one or more additional first family destination vectors B and C, as disclosed elsewhere in this application. The method can, in addition, or alternatively, include at least one first family vector 1A-R, 2-R, B-R, and/or C-R, for antisense expression of an FOI. In embodiments of the methods utilizing 1A-R, 2-R, B-R, and/or C-R, the ordered combination of a plurality of nucleic acid fragments of interest includes at least one antisense nucleic acid fragment of interest.

The method can further include a second family destination vector 2 as disclosed elsewhere in this application. The method can, in addition, or alternatively, include one or both second family destination vectors B and/or C, as disclosed elsewhere in this application.

In one embodiment of the disclosed methods, the restriction enzyme sites are removed by restriction enzyme cleavage, and are restored on integration of the FOI into the destination vector.

In some embodiments of the disclosed methods, at least two modified second family destination vectors, each containing a distinct (from one another) ordered combination of a plurality of nucleic acid fragments of interest, are generated. In further embodiments, at least one new vector of the first family of destination vectors is provided, and the modified second destination vectors are combined with the at least one first family destination vector, a type IIS restriction enzyme that cleaves the vectors at the second restriction enzyme site, and a DNA ligase, under conditions that allow release of each distinct ordered combination of nucleic acid fragments of interest as a polynucleotide unit from the modified second destination vectors. In this embodiment, the fragments of interest remain bound to each other in order as a polynucleotide unit with one of a first, third, or fourth signature element at its 5' end and one of a second, third, or fourth signature element at its 3' end.

The polynucleotide units are ligated to each other and into a first family destination vector, just as the individual FOIs were ligated to each other and to the second family destination vectors, as follows. A first unit having a first signature element on its 5' end is ligated at its 5' end to the 3' end of a first family destination vector, the first family destination vector having a complementary first signature element. A second unit having a second signature element on its 3' end is ligated at its 3' end to the 5' end of the same first family destination vector, the first family destination vector having a complementary second signature element. The polynucleotide units are also (before, after, or during ligation to the vector) ligated to each other at at least a third signature element, one unit having the third signature element on its 3' end, and another unit having the complementary third signature element on its 5' end; thereby generating at least one modified first family vector which includes an ordered combination of at least four nucleic acid fragments of interest.

In some embodiment, the ligation reactions are performed in a ligation buffer containing a polyglycol polymer. The ligation buffer can further include 20-80 mM Tris-HCl, (pH 7-8); 0.1-4.0 mM, dithiothreitol (DTT); 1-20 mM $MgCl_2$; 0.1-2.0 mM ATP; and 0.1-4.0% polyglycol polymer.

The disclosed methods can also involve transforming bacteria with the modified vectors. In some embodiments, the bacteria are genetically modified to express *Therms aquaticus* DNA methyltransferase I.

In one embodiment of the claimed methods, at least one of the polynucleotides containing the FOI is a vector with the FOI flanked by a first signature element on the 5' side of the forward strand, and a second signature element on the 3' side of the FOI. The vector further has a first and a second Type IIS restriction enzyme site on the 5' side of the FOI, and the same first and second Type IIS restriction enzyme site on the 3' side of the FOI. In a specific example, the vector is a pSTART vector.

In another embodiment of the claimed methods, the polynucleotide is a nucleic acid fragment that includes the FOI, the signature elements, and the Type IIS restriction enzyme sites, but is not a vector.

BRIEF DESCRIPTION OF THE FIGURES

The patent or application file contains at least one drawing executed in color. Copies of this patent or patent application publication with color drawing(s) will be provided by the Office upon request and payment of the necessary fee.

All sequences present in the Figures are provided in Table 1.

using the templates 8m1 (180 ng) and 4m1 (180 ng). The DNA oligos 26 nt and 26 nt fused to acridine (26 nt-Acr) (always 50 µM) were incubated with each template as in D. Reaction was stopped and gel bands (shown) quantified and plotted as percentage of the control without oligo (N.O.) as in C. EarI activity on each site, s1 (4 mismatches) and s2 (13 mismatches), was evaluated independently (right panel). The 4m1, 5m2, 7m1 and 8m1 templates were originally cloned in pSTART from three GBlocks: two universal GBlocks (TFOsynt_Uni5' and TFOsynt_Uni3') along with its respective central fragment TFOsynt_4 m1, TFOsynt_5 m2, TFOsynt_7 m1, TFOsynt_8 m1.

Figure 16B:
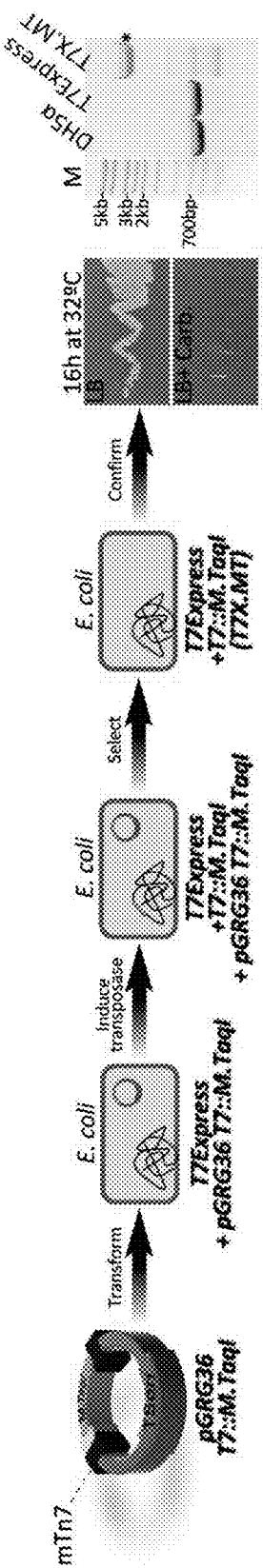

FIGS. 16A-16B. M.TaqI synthesized gene cluster (1884 bp) and graphical representation of its insertion into the T7Express (NEB) genome. (A) M.TaqI gene was codon optimized for *E. coli* as shown (green highlight). T7 elements, promoter (light blue highlight) and terminator (dark blue highlight) plus the lacOperator (yellow highlight) and the overlap region for cloning in pGRG36 (dark red) at the NotI site (underlined) are shown. Ribosome biding site is bold/italic (AAGGAG), light gray is a secondary expression cassette and lower case is a linker sequence. Cloning region is flanked by the terminal repeats of Tn7 (mTn7) at the pGRG36 vector. (B) Graphical representation for construction of T7X.MT as described in McKenzie and Craig (McKenzie, G. J. & Craig, N. L. *BMC Microbiology* 6, 39 (2006)). Briefly, the synthetic fragment shown in A was cloned in pGRG36 using the Gibson assembly strategy, transformed in the T7Express (NEB) strain and selected in carbenicillin plates at 30-32° C. due to a thermosensitive replication origin (TS-ori). Five single colonies were picked and inoculated in liquid LB media in the presence of 0.1% L-arabinose to induce the transposases overnight. Cultures were diluted and plated at 42° C. overnight (to block plasmid replication and allow growth of transgenes). Single colonies were again grown in liquid media and re-streaked in LB plates. Carbenicillin sensitivity tests were conducted (16 h growth at 32° C.) and one sensitive strain (defined as T7X.MT) had the insertion into the genome confirmed by PCR. In the absence of a Tn7 insertion, the genomic primers will yield a ≈678 bp product (DH5a and T7Express, controls). In the presence of the Tn7 insertion this product will increase and final size should be larger than 2562 bp but smaller than 3466 bp (asterisk), depending on the strain used for engineering. The strain shown was used for our methylation tests (see FIGS. 11B-11D) and hosts the TNT-system vectors. The T7X strain was selected for strain development due to its specific genotype that allows stable expression of exogenous proteins (deficient in proteases Lon and OmpT) and its ability in not restricting methylated DNA (McrA$^-$, McrBC$^-$, EcoBr$^-$m$^-$, Mrr$^-$). M.TaqI expression was seen to significantly impair *E. coli* growth if the incubation temperature increased over 42° C. or IPTG concentration increased over 0.5 mM.

DETAILED DESCRIPTION OF THE DISCLOSURE

Disclosed herein is a cloning system ("TNT-cloning") that allows a universal library to be created for different DNA fragments to be directionally joined, up to several kilobases, by picking and mixing DNA components within the system components. This system increases the current capabilities of assembling and sharing multi-gene constructs.

Destination Vectors

The disclosed cloning system provides two families of double-stranded "destination" vectors for integration and combination of nucleic acid fragments of interest, and methods of cloning that involve potentially infinite rounds of cloning between vectors of the two families, such that multiple genetic elements can be combined together to form a final vector with many combined genetic components. The disclosed vectors allow a "cloning loop" that concatenates and automatically matches protein-encoding sequences in frame with each DNA fragment; eliminates the use of sequence overlap/homology, linkers and adaptors; and does not require mutation of DNA fragments that contain internal cleavage sites recognized by restriction enzymes.

Nucleic acid fragments of interest ("FOIs") are initially integrated individually into vectors of a first family. Cloning from vectors of the first family into vectors of the second family provides combination of multiple FOIs into one or more second family vectors, to generate at least one second family vector with two or more FOIs integrated in frame and in a desired sequence with one another.

The first and second vector families (referred to herein as the "alpha" or "α" family, and the "omega" or "Ω" family, where either alpha or omega can be the first vector family or the second vector family) share the same restriction enzyme sites, and the same "signature elements", which are pre-selected 3-nucleotide signature elements that allow cleavage and joining of nucleic acid fragments of interest from one vector to another. These 3-nucleotide signature elements utilized in the disclosed methods provide the name of "TNT" (tri-nucleotide repeat) cloning.

Type IIS Restriction Enzymes and Enzyme Sites

The disclosed vectors contain Type IIS restriction enzyme sites. "Type IIS" restriction enzymes/endonucleases interact with double-stranded DNA at the recognition site, which is typically an asymmetric nucleotide sequence about 4-7 bp long, and the cleavage site, which is usually 1-20 bp away from the recognition site. Type IIS restriction enzymes are listed, for example, on the REBASE website. Any reference to a "restriction enzyme" or "restriction enzyme site" in this disclosure is meant to encompass a Type IIS restriction enzyme or enzyme site. A "Type IIS restriction enzyme site" is defined herein as a nucleic acid sequence that is bound to/recognized by and cleaved by a Type IIS restriction enzyme, with cleavage occurring 3' of the recognition sequence. Thus, a Type IIS restriction enzyme site as disclosed herein encompasses both the recognition site and the cleavage site for a particular Type IIS enzyme. Preferred Type IIS restriction enzyme sites are sites recognized by enzymes that leave a three nucleotide "cohesive" or "sticky" end, that is, a three-nucleotide single strand extension on the forward or reverse strand of a double-stranded polynucleotide sequence, that is available for base-pairing with the complementary cohesive end of another polynucleotide sequence. This three nucleotide cohesive end is designed to be a "signature element" as detailed further herein.

The first and second type IIS restriction enzyme sites can be selected from restriction enzyme recognition sites for *Enterobacter aerogenes* I (EarI), *Lysobacter gummosus* RFLI (LguI), *Bacillus coagulans* 5I (Bco5I), *Bacillus coagulans* 116I (Bco116I), *Bacillus coagulans* KI (BcoKI), *Bacillus stearothermophilus* XI (BsaXI), *Bacillus stearothermophilus* ZI (BseZI), *Bacillus stearothermophilus* 6I (Bst6I), *Bacillus stearothermophilus* IMI (BssIMI), *Bacillus sphaericus* QI (BspQI), *Bacillus stearothermophilus* IMI (BssIMI), *Bacillus subtilis* 6I (Bsu6I), *Bacillus atrophaeus* HI (BatHI), *Enterobacter amnigenus* RFL1104 (Eam1104I), *Klebsiella pneumoniae* NIH30III (KpnNIH30III), *Planococcus citreus* SI (PciSI), *Rhizobium leguminosarum* AI (RleAI), *Saccharopolyspora* species I (SapI), *Staphylococ-*

*cus intermedius* I (SimI), and *Vibrio parahaemolyticus* K32I (VpaK32I). In one embodiment, the first and second type IIS restriction enzyme sites are selected from *Enterobacter aerogenes* I (EarI) and *Lysobacter gummosus* RFLI (LguI) restriction enzyme sites. In a further embodiment, the first type IIS restriction enzyme site is an EarI site, and the second type IIS restriction enzyme site is an LguI site. In another embodiment, the first type IIS restriction enzyme site is an LguI site, and the second type IIS restriction enzyme site is an EarI site.

The alpha and omega destination vector families contain the same two restriction enzyme sites, but in opposite "orientation" in the vector sequence. That is, the first family can have, for example, two first restriction enzyme sites to release the FOI, and two second restriction enzyme sites to integrate a new FOI, while the second family will have the same two first restriction enzyme sites to integrate a new FOI, and the same two second restriction enzyme sites to release an FOI. Thus, combining vectors of a first and second family with either restriction enzyme will allow transfer of an FOI from one family to the other, and continued transfer of FOIs from one family to another can be achieved simply by alternating restriction enzymes in a combined restriction/ligation reaction. This allows for continuous cloning loops to combine FOIs in a desired sequence.

Each destination vector contains a first restriction enzyme site in the 5'-3' orientation on the forward strand, and also a first restriction enzyme site in the 5'-3' orientation on the reverse strand, meaning the forward strand has one first restriction enzyme site in the 5'-3' direction, and one reverse complement of the first restriction enzyme site, opposite the first restriction enzyme site on the reverse strand. Similarly, each destination vector contains a second restriction enzyme site in the 5'-3' orientation on the forward strand, and also a second restriction enzyme site in the 5'-3' orientation on the reverse strand, meaning the forward strand has one second restriction enzyme site in the 5'-3' direction, and one reverse complement of the second restriction enzyme site, opposite the second restriction enzyme site on the reverse strand.

Restriction enzyme sites on each vector are designed so that cleavage occurs immediately 5' to the signature element. Precise cleavage sites and cohesive end signature elements are exemplified in FIGS. 4-7 and in the description of these figures. In addition, cleavage occurs such that the restriction enzyme site being cleaved is removed from the sequence of the fragment of interest and remains on the vector backbone. The restriction enzyme site is restored on integration of the FOI to a new vector.

Signature Elements

Restriction enzyme cleavage leaves a three nucleotide cohesive end "signature" or "signature element" (used interchangeably herein with "signature sequence") on one end of a vector or FOI, and the reverse complement of the signature element on the end of an FOI or vector to which the signature will be joined. The double-stranded signature is restored when the ends are ligated, to allow integration of an FOI or FOIs in the desired orientation in the vector. Although any 3-nucleotide signature can be used, preferred signature elements have no more than 66% GC content and do not encode stop or start codons. In some embodiments, preferred signatures have an adenine positioned to create an M.TaqI methylation site. In contrast to the restriction enzyme site, which is removed from the FOI during digestion and stays on the vector backbone, signature elements remain on both the FOI and the vectors. Examples of signature elements used herein are: acc; gat; agt; agt; aat; ggt; atc (on one strand; the reverse complement of each signature element is on the opposite strand; in this case, the paired signature elements are acc/tgg, gat/cta, agt/tca, aat/tta, ggt/cca, and atc/tag).

As an example, the α2 vector has, from 5'-3' on the forward strand, adjacent signature elements 3 and 1, and signature element 2; each signature element has either a first or second restriction enzyme site immediately 5' to the signature, on either the forward or reverse strand, so that digestion with the respective first or second restriction enzyme cleaves across the signature. See, FIG. 4; the dotted lines across each signature element indicate the precise sequence cleaved by the respective restriction enzyme and the resulting cohesive end signature. As seen in FIG. 2, the α2 vector has an LguI restriction enzyme site on the forward strand 5' to signature element 3 (tgg/acc) that leaves tgg/acc cohesive ends by cleavage across signature element 3. The α2 vector also has an EarI restriction enzyme site on the reverse strand 5' to the reverse complement of signature element 1 (acc/tgg) that leaves acc/tgg cohesive ends across signature element 1. The α2 vector also has an EarI restriction enzyme site on the forward strand and an LguI restriction enzyme site on the reverse strand, each 5' to signature element 2 (gat/cta) on their respective strands, such that digestion with either enzyme leaves gat/cta cohesive ends across signature element 2. In this way, digestion with LguI cleaves at signature elements 3 and 2, while digestion with EarI cleaves at signature elements 1 and 2.

Selectable Markers

Each destination vector has a first selectable marker, which is flanked by restriction enzyme sites and it released on digestion with either restriction enzyme. The first selectable marker is replaced by the fragment of interest. The first and second family destination vectors can have the same first selectable marker, or the first selectable marker can differ between vectors of the first and second families. Selection for loss of the marker is utilized to identify integration of the fragment of interest. Suitable selection markers include chromogenic markers, enzymatic markers, fluorescent markers, or other markers known in the art, the absence of which can be used to detect integration of the FOI. Exemplary markers include, but are not limited to, lacZ (beta-galactosidase gene), bgaB (alpha-galactosidase from *G. stearothermophilus*); xylE (catechol-2,3-dioxygenase from *Pseudomonas putida*), CAT (chloramphenicol acetyltransferase), and GFP (green fluorescent protein).

All first family vectors are all arranged to have the first selectable marker flanked by first and second signature elements, with second enzyme sites 3' of the first and 5' of the second signature elements. All second family vectors are all arranged to have the marker flanked by first and second signature elements, with first enzyme sites 3' of the first and 5' of the second signature elements.

Each destination vector also has a second selectable marker, to identify transformants containing the vector. Suitable second selectable markers include antibiotic resistance genes and gene with exogenous nutritional capability. These may include, for example, resistance to carbenicillin, chloramphenicol, ampicillin, kanamycin, or spectinomycin antibiotic genes, or xylose or lactose nutritional genes.

Additional Components of the Disclosed Vectors

The vectors further include other components required for replication and maintenance in a suitable host organism, for example, one or more origins of replication for replication in a suitable host organism.

First Family of Destination Vectors

The cloning region of each vector in the first family of vectors is arranged, from 5' to 3' on the forward/sense strand of each vector, as follows: (a) the forward sequence of the first type IIS restriction enzyme site; (b) the forward sequence of the first signature element; (c) the reverse complement sequence of the second type IIS restriction enzyme site, with the restriction enzyme cleavage site at the 3' end of the first signature element; (d) the selectable marker gene; (e) the forward sequence of the second type IIS restriction enzyme site, with the restriction enzyme cleavage site at the 5' end of the second signature element; (f) the forward sequence of a second signature element; and (g) the reverse complement sequence of the first type IIS restriction enzyme site.

The first family of destination vectors includes at least two first family destination vectors 1A and 2. Each of the destination vectors in the first family includes the same first type IIS restriction enzyme site, the same second type IIS restriction enzyme site, and a selectable marker gene, and wherein each destination vector comprises at least three different signature elements selected from four 3-nucleotide signature elements.

In addition to the above arrangement, the first family destination vectors 1A and 2 are further organized as follows. The first family destination vector 1A further includes, from 5' to 3' on the sense strand, the forward sequence of a third signature element between (f) the forward sequence of the second signature element and (g) the reverse complement sequence of the first type IIS restriction enzyme site. The first family destination vector 2 further includes, from 5' to 3' on the sense strand, the forward sequence of the third signature element between (a) the forward sequence of the first type IIS restriction enzyme site and (b) the forward sequence of the first signature element.

The first family of destination vectors can further include first family destination vectors B and C. Destination vector B includes, from 5' to 3' in the sense strand: the forward sequence of the third signature element between (a) the forward sequence of the first type IIS restriction enzyme site and (b) the forward sequence of the first signature element. Vector B further includes the forward sequence of a fourth signature element between (f) the forward sequence of the second signature element and (g) the reverse complement sequence of the first type IIS restriction enzyme site. Destination vector C further includes, from 5' to 3' on the sense strand, the forward sequence of the fourth signature element between (a) the forward sequence of the first type IIS restriction enzyme site and (b) the forward sequence of the first signature element.

Further provided is a second family of double-stranded destination vectors including at least one second family destination vector 1A, each vector in the second family having the same first and second type IIS restriction enzyme sites as in the first family of destination vectors, and at least three signature elements selected from four 3-nucleotide signature elements which are the same signature elements as in the first family of destination vectors, and further including a selectable marker gene that can be the same or different from the selectable marker gene of the first family destination vectors.

Each second family destination vector includes, from 5' to 3' in the sense strand: (a) the forward sequence of the second type IIS restriction enzyme site; (b) the forward sequence of the first signature element; (c) the reverse complement sequence of the first type IIS restriction enzyme site; (d) the selectable marker gene; (e) the forward sequence of the first type IIS restriction enzyme site; (f) the forward sequence of said second signature element; and (g) the reverse complement sequence of the second type IIS restriction enzyme site, with the restriction enzyme cleavage site at the 3' end of the third signature element.

The second family destination vector 1A further includes, from 5' to 3' on the sense strand, the forward sequence of a third signature element between (f) the forward sequence of the second signature element and (g) the reverse complement sequence of the second type IIS restriction enzyme site.

The second family of destination vectors can also include, in addition to second family destination vector 1A, a second family destination vector 2 which further includes, from 5' to 3' on the sense strand, the forward sequence of the third signature element between (a) the forward sequence of the second type IIS restriction enzyme site and (b) the forward sequence of the first signature element.

The second family of destination vectors can also include, in addition to second family destination vector 1A, second family destination vectors B and C. Destination vector B further includes, from 5' to 3' on the sense strand, the forward sequence of the third signature element between (a) the forward sequence of the second type IIS restriction enzyme site and (b) the forward sequence of the first signature element; and the forward sequence of a fourth signature element between (f) the forward sequence of the second signature element and (g) the reverse complement sequence of the second type IIS restriction enzyme site. Destination vector C further includes, from 5' to 3' on the sense strand, the forward sequence of said fourth signature element between (a) the forward sequence of the second type IIS restriction enzyme site and (b) the forward sequence of the first signature element.

Each member of the first and second families of destination vectors may further contain a second selectable marker which is the same within each family, but which differs between the first and second families. The second selectable markers for said first and second families can be, for example, antibiotic resistance genes.

The disclosed cloning system can further include a ligation buffer which has polypropylene glycol (PPG). The ligation buffer can further include 20-80 mM Tris-HCl, (pH 7-8); 0.1-4.0 mM, dithiothreitol (DTT); 1-20 mM $MgCl_2$; 0.1-2.0 mM ATP; and 0.1-4.0% PPG.

In another embodiment, the first family of destination vectors further includes at least one vector for antisense expression of a nucleic acid, wherein the signature elements present in any vector for antisense expression can be present in either a forward or reverse complement orientation in the vector sequence. The vectors for antisense expression can be selected from first family destination vectors 1A-R, First family destination vector 1A-R includes, from 5' to 3' in the sense strand: the forward sequence of the first type IIS restriction enzyme site; the forward sequence of the first signature element; the reverse complement sequence of the second signature element; the reverse complement sequence of the second type IIS restriction enzyme site; the selectable marker gene; the forward sequence of the second type IIS restriction enzyme site; the reverse complement sequence of the first signature element; the forward sequence of a third signature element; and the reverse complement sequence of the first type IIS restriction enzyme site.

First family destination vector 2-R includes, from 5' to 3' in the sense strand: the forward sequence of the first type IIS restriction enzyme site; the forward sequence of the third signature element; the reverse complement sequence of the second signature element; the reverse complement sequence of the second type IIS restriction enzyme site; the selectable marker gene; the forward sequence of the second type IIS restriction enzyme site; the reverse complement sequence of the first signature element; the forward sequence of the second signature element; and the reverse complement sequence of the first type IIS restriction enzyme site.

First family destination vector B-R includes, from 5' to 3' in the sense strand: the forward sequence of the first type IIS restriction enzyme site; the forward sequence of the third signature element; the reverse complement sequence of the second signature element; the reverse complement sequence of the second type IIS restriction enzyme site; the selectable marker gene; the forward sequence of the second type IIS restriction enzyme site; the reverse complement sequence of the first signature element; the forward sequence of the fourth signature element; and the reverse complement sequence of the first type IIS restriction enzyme site.

First family destination vector C-R includes, from 5' to 3' in the sense strand: the forward sequence of the first type IIS restriction enzyme site; the forward sequence of the fourth signature element; the reverse complement sequence of the second signature element; the reverse complement sequence of the second type IIS restriction enzyme site; the selectable marker gene; the forward sequence of the second type IIS restriction enzyme site; the reverse complement sequence of the first signature element; the forward sequence of the second signature element; and the reverse complement sequence of the first type IIS restriction enzyme site.

Further disclosed herein are methods for generating one or more vectors containing an ordered combination of a plurality of nucleic acid fragments of interest (FOIs). The methods include integrating each FOI with one type of first family destination vector to produce a set of modified first family vectors, each modified vector containing an FOI; then transferring the FOI in each vector to a second family destination vector, such that at least two FOIs are integrated into each second family destination vector, to produce one or more modified second family vectors containing an ordered combination of a plurality of FOIs. In each case, the segment of the destination vector containing the selectable marker is excised from the destination vector, and is replaced by the FOI.

This cloning cycle can be repeated, such that, for example, two or more distinct ordered combinations of FOIs in two or or more modified second family destination vectors can be placed in sequential order by integrating the ordered combinations of FOIs into a new set of first family destination vectors, such that each new modified first family vector now contains two or more ordered combinations of multiple FOIs. The methods can also start with the second family of vectors as the initial destination vectors, integrate into one or more first family vectors, and so on. The methods are detailed as follows.

The disclosed methods begin with providing two or more polynucleotides, each polynucleotide including (i) an FOI; (2) the same type IIS restriction enzyme site at each of the 5' and 3' ends, where the restriction enzyme site at each of the 5' and 3' ends can be cleaved by the same first and second type IIS restriction enzymes utilized throughout the methods; and (iii) two 3-nucleotide signature sequence elements, wherein each polynucleotide has the same first signature element 5' of the FOI and the same second signature element 3' of the FOI, the 5' signature element being distinct from the 3' signature element. The polynucleotide can be any starting vector, including but not limited to a pSTART vector, or a first or second family destination vector; or the polynucleotide can be a nucleic acid sequence that extends 5-50 nucleotides 5' and/or 3' of the FOI itself.

The methods next involve providing a first family of destination vectors including at least first family vectors 1A and 2 as described previously; and providing a type IIS restriction enzyme that cleaves each first family vector at the second restriction enzyme site.

The polynucleotides, the first family vectors, the type IIS restriction enzyme, and a DNA ligase, are placed together under conditions that allow the type IIS restriction enzyme to cleave the destination vectors and the polynucleotides at the second restriction enzyme site, and that also allow ligation of the FOIs into a member of the first family of destination vectors. To receive an FOI, the first family vectors are cleaved with the second type IIS enzyme, which produces (i) a 3-nucleotide overhang representing (the reverse complement sequence of) the first signature element and (ii) a 3 nucleotide overhang representing (the forward sequence of) the 2nd signature element. The first and second signatures are utilized for ligation to the vector, while the third, fourth, and any other signature elements are used to join FOI to FOI.

This creates a set of at least two modified first family vectors, each modified vector having one FOI substituted for the selectable marker gene.

In the next step of the method, at least one vector 1A of a second family of destination vectors is provided, along with a type IIS restriction enzyme that cleaves each vector in the first and second families of destination vectors at the first restriction enzyme site. The modified first family destination vectors are placed together with the at least one second family destination vector 1A, the type IIS restriction enzyme that cleaves the vectors at the first restriction enzyme site, and a DNA ligase, under conditions that allow release of the FOIs from the modified first destination vectors, ligation of the FOIs into the at least one second family destination vector, and ligation of the FOIs to each other within the second family destination vector in an ordered arrangement, thereby generating at least one modified second family vector with an ordered combination of a plurality of nucleic acid fragments of interest.

Ligation of the FOIs to the second family destination vector occurs as follows: a first FOI having a first signature element on its 5' end is ligated at its 5' end to the 3' end of the second family destination vector, the second family destination vector having a complementary first signature element; and a second FOI having a second signature element on its 3' end is ligated at its 3' end to the 5' end of the second family destination vector, said second family destination vector having a complementary second signature element. Ligation of the FOIs to each other occurs at at least a third signature element, with one FOI having the third signature element on its 3' end, and another FOI having the complementary third signature element on its 5' end, such that they join.

In a specific embodiment, the first FOI, which is or can be joined at its 5' end to the 3' end of the second family destination vector, has the third signature element on its 3' end, and the second FOI, which is or can be joined at its 3' end to the 5' end of the second family destination vector, has the complementary third signature element on its 5' end, such that the first and second fragments of interest are ligated to each other through the third signature element and are joined to the second family destination vector in the ordered combination of vector-first FOI-second FOI-vector.

In a further embodiment, there are three FOIs which are ligated to each other such that, from 5' to 3', the fragments are in the order of first FOI, third FOI, and second FOI, as follows. The first fragment of interest has the third signature element on its 3' end, and the third fragment of interest has the complementary third signature element on its 5' end, so that the first and third fragments of interest are ligated to each other through the third signature element. Further, the second fragment of interest has a fourth signature element on its 5' end, and the third fragment of interest has the complementary fourth signature element on its 3' end, so that the second and third fragments of interest are ligated to each other through the fourth signature element. The first FOI is joined at its 5' end to the vector, and the second FOI is joined at its 3' end to the vector. The ordered combination is thus vector-first FOI-third FOI-second FOI-vector.

The method can further include one or more additional first family destination vectors B and C, as disclosed elsewhere in this application. The method can, in addition, or alternatively, include at least one first family vector 1A-R, 2-R, B-R, and/or C-R, for antisense expression of an FOI. In embodiments of the methods utilizing 1A-R, 2-R, B-R, and/or C-R, the ordered combination of a plurality of nucleic acid fragments of interest includes at least one antisense nucleic acid fragment of interest.

The method can further include a second family destination vector 2 as disclosed elsewhere in this application. The method can, in addition, or alternatively, include one or both second family destination vectors B and/or C, as disclosed elsewhere in this application.

In one embodiment of the disclosed methods, the restriction enzyme sites are removed by restriction enzyme cleavage, and are restored on integration of the FOI into the destination vector.

In some embodiments of the disclosed methods, at least two modified second family destination vectors, each containing a distinct (from one another) ordered combination of a plurality of nucleic acid fragments of interest, are generated. In further embodiments, at least one new vector of the first family of destination vectors is provided, and the modified second destination vectors are combined with the at least one first family destination vector, a type IIS restriction enzyme that cleaves the vectors at the second restriction enzyme site, and a DNA ligase, under conditions that allow release of each distinct ordered combination of nucleic acid fragments of interest as a polynucleotide unit from the modified second destination vectors. In this embodiment, the fragments of interest remain bound to each other in order as a polynucleotide unit with one of a first, third, or fourth signature element at its 5' end and one of a second, third, or fourth signature element at its 3' end.

The polynucleotide units are ligated to each other and into a first family destination vector, just as the individual FOIs were ligated to each other and to the second family destination vectors, as follows. A first unit having a first signature element on its 5' end is ligated at its 5' end to the 3' end of a first family destination vector, the first family destination vector having a complementary first signature element. A second unit having a second signature element on its 3' end is ligated at its 3' end to the 5' end of the same first family destination vector, the first family destination vector having a complementary second signature element. The polynucleotide units are also (before, after, or during ligation to the vector) ligated to each other at at least a third signature element, one unit having the third signature element on its 3' end, and another unit having the complementary third signature element on its 5' end; thereby generating at least one modified first family vector which includes an ordered combination of at least four nucleic acid fragments of interest.

In some embodiment, the ligation reactions are performed in a ligation buffer with polypropylene glycol (PPG). The ligation buffer can further include 20-80 mM Tris-HCl, (pH 7-8); 0.1-4.0 mM, dithiothreitol (DTT); 1-20 mM MgCl$_2$; 0.1-2.0 mM ATP; and 0.1-4.0% PPG.

The disclosed methods can also involve transforming bacteria with the modified vectors. In some embodiments, the bacteria are genetically modified to express a DNA methyltransferase, such as *Therms aquaticus* DNA methyltransferase (M.taq I). Methylation of amino acids within the LguI restriction enzyme sites can mask the LguI binding site when using EarI as the restriction enzyme, thus avoiding EarI cleavage of the LguI site.

Fragment of Interest

The fragment of interest (FOI) can be any nucleic acid element of interest. Examples include, but are not limited to, a complete or partial sequence of a gene of interest, or a fragment thereof; a promoter sequence; an enhancer sequence; a repressor-binding sequence; an untranslated region; a terminator sequence; a signal sequence; a sequence encoding an antisense RNA; a tag or label sequence; a reporter gene; and so on.

The FOI can be in a vector prior to introduction into either a first or second family destination vector. In this embodiment, the polynucleotide containing the FOI is a vector. Thus, in one embodiment of the claimed methods, at least one of the polynucleotides containing the FOI is a vector with the FOI flanked by a first signature element on the 5' side of the forward strand, and a second signature element on the 3' side of the FOI. The vector further has a first and a second Type IIS restriction enzyme site on the 5' side of the FOI, and the same first and second Type IIS restriction enzyme site on the 3' side of the FOI. In a specific example, the vector is a pSTART vector, as outlined, for example, in FIG. 3. However, the polynucleotide can be any starting vector, including but not limited to a pSTART vector, or a first or second family destination vector; or other vectors known in the art.

In another embodiment of the claimed methods, the polynucleotide is a nucleic acid fragment that includes the FOI, the signature elements, and the Type IIS restriction enzyme sites, but is not a vector. In some embodiments, the polynucleotide is domesticated, that is, the sequence of the FOI is modified, for example in an amplification reaction, by Gibson assembly, or by other methods known in the art. In other embodiments, the polynucleotide containing the FOI is not domesticated, and instead, oligonucleotides ("oligos") that are complementary to the FOI are used to introduce signature elements and restriction enzymes sites flanking the FOI to create a modified polynucleotide sequence. In this embodiment, the polynucleotide can be a nucleic acid sequence that extends 5-50 nucleotides 5' and/or 3' of the FOI itself.

Digestion/Ligation Buffer

Further disclosed are buffers that can be used for either or both of the digestion and ligation reactions. The disclosed buffers contain at least a polyglycol polymer. Preferred formulations include 20-80 mM, 30-70 mM, 40-60 mM, or 50 mM Tris-HCl, (pH 6-9, 7-8, or preferably 7.5); 0.1-4.0 mM, 1-3 mM, or 2 mM dithiothreitol (DTT); 1-20 mM, 5-15 mM, 8-12 mM, or 10 mM MgCl$_2$; 0.1-2.0 mM, 0.5-2.0 mM, 0.8-1.2 mM, or 1 mM ATP; and 0.1-4.0%, 1-3%, 1.5-2.5%, or 2% polyglycol polymer. As used herein, reference to a "polyglycol polymer" includes polymers and block copolymers of poly(glycol) moieties such as poly(ethylene glycol) ("PEG"), poly(propylene glycol) ("PPG"), poly(butylene glycol), or methoxy-poly(ethylene glycol). In one example, a PEGylated PPG, such as poly(ethylene glycol)-block-poly(propylene glycol) (PEG-PPG), poly(propylene glycol)-block-poly(ethylene glycol) (PPG-PEG), poly(ethylene glycol)-block-poly(propylene glycol)-block-poly(ethylene glycol) (PEG-PPG-PEG), or a block copolymer PPG-PEG-PPG, is used. Generally speaking, polyglycol polymers suitable for use in the buffer have an average molecular weight in the range of 800 kD to 6000 kD, or 1000 kD to 5800 kD. Polyglycol polymers and block copolymers are available via various commercial sources (e.g., Sigmal Aldrich). In certain embodiments, the polyglycol polymer used in the buffer has an average molecular weight of about 1000 kD to 2800 kD, or about 1100 kD. In a specific embodiment, the polyglycol polymer is a block copolymer, poly(ethylene glycol)-block-poly(propylene glycol)-block-poly(ethylene glycol) ("PEG-PPG-PEG"), having an average molecular weight of about 1100 kD.

In order to ligate the destination vectors and FOIs, a DNA ligase is used, such as T4 DNA ligase or other suitable DNA ligase enzymes. In some embodiments, 20-60, 30-50, 35-45, or 40 units (U) of T4 DNA ligase is used in the reaction. In embodiments using EarI, 1-10, 3-7, or 5 U of EarI is used in a reaction, while if LguI is used, 0.1-1.0, 0.3-0.7, or 0.5 U of LguI is used. Preferred digestion/ligation reactions include incubation at 30-38° C., preferably about 34° C., for 40-50 seconds, preferably 45 seconds, and 12-18° C., preferably about 16° C. for 4-5 minutes, preferably 4.5 min, repeated for 10-90 cycles, 40-60, 45-55, or about 25 or 50 cycles.

EXAMPLES

TNT-Family of Vectors

All primers, genomic blocks (GBlocks) and gene cassettes are listed in Table II.

Nucleic acid manipulation followed the general guidelines described in Sambrook, J. & Russell, D. W., Cold Spring Harbor Laboratory Press, Cold Spring Harbor, N.Y., (2001). DNA preparation was performed by either traditional phenol:chloroform extraction or DNA extraction kit (5PRIME #2300010). The pSTART is a pUC19-backbone vector, which carries the ampicillin/carbenicillin resistance gene and was built domesticating EarI sites (5'CTCTTC3') by using Gibson assembly (Gibson, D. G. et al., Nature methods 6, 343-345 (2009)) to join the PCR products of primers 1) pUPD-FW1 and pUPD-RW1 (188 bp), 2) pUPD-FW2 and pUPD-RW2 (149 bp), 3) pUPD-FW3 and pUPD-RW3 (301 bp), 4) pUPD-FW4 and pUPD-RW4 (1838 bp) and 5) pUPD-FW5 and pUPD-RW5 (274 bp). The "ΔM15ω-peptide" was separately amplified from *E. coli* DH5a using the primers pUPD-RW3.1 and FW_adap and assembled into domesticated pSTART linearized by PCR using the primers pUPD-FW3.1 and pUPD-RW5. For the M.Test vector, used on M.TaqI assays in T7Express and T7X.MT, the pUPD-RW5-M_Test and pUPD_adap_met.test-FW were used instead of pUPD-RW5 and FW_adap, respectively (creating the M.TaqI site 5'TCGA3'). The backbone of the binary vector pPZP200 (Hajdukiewicz, P., et al., *Plant molecular biology* 25, 989-994 (1994)) (positions 1 to 6495 bp) plus a spectinomycin resistance cluster were domesticated at different 5'CTCTTC3' sites using the primers αΩvector-FW and EarI-RW1 (1132 bp), EarI-FW1 and EarI-RW2 (2699 bp), EarI-FW2 and EarI-RW3 (493 bp), EarI-FW3 and EarI-RW4 (2866 bp), EarI-FW4 and EarI-RW5 (234 bp) and, EarI-FW5 and αΩvector-RW (817 bp). PCR products were purified, mixed in equimolar ratio and re-amplified using the primers αΩvector-nested-FW and αΩvector-nested-RW (8080 bp band). The 8080-bp band was re-amplified with primers αΩvector-FW and αΩvector-RW to generate the α-backbone segment. The α version had the appropriate primer pairs α1A-Fw and α1A-Rw, α2-Fw and α2-Rw, αB-Fw and αB-Rw, αC-Fw and αC-Rw, α1R-Fw and α1R-Rw, α2R-Fw and α2R-Rw amplifying the reporter ΔM15ω from pSTART during a first PCR with each product followed by a secondary PCR with the primers PCR2_to_αVector-Fw and PCR2_to_αVector-Rw to create the 18-bp overlap needed for joining each segment by Gibson assembly to the α backbone.

First, vector α1A was built, and after sequencing of CDS present in this backbone plus the T-DNA borders, the remaining members α2, αB, αC, α1A-R, α2-R were assembled. Similarly, the appropriate primer pairs Ω1A-Fw and Ω1A-Rw, Ω2-Fw and Ω2-Rw, ΩB-Fw and ΩB-Rw, ΩC-Fw and ΩC-Rw, Ω1R-Fw and Ω1R-Rw and, Ω2R-Fw and Ω2R-Rw were used to amplify the reporter ΔM15ω from pSTART during a first PCR with each product followed by a secondary PCR with the primers PCR2_to_ΩVector-Fw and PCR2_to_ΩVector-Rw to create the 18-bp overlap needed for joining each segment, by Gibson assembly, to the α backbone creating the plasmids Ω1Aabb, Ω2abb, ΩBabb, ΩCabb, Ω1A-Rabb, Ω2-Rabb, where "abb" means a backbone. These Ω members then had the spectinomycin marker (aminoglycoside adenylyltransferase) switched to kanamycin (aminoglycoside phosphotransferase) by linearizing each member using the primers KStrat2_TNT-FW and KStrat2_TNT-RW (9351 bp) to be joined by Gibson assembly with fragment 1 amplified with Kan_to_O-FW2 and KStrat2_TOP-RW (1496 bp) and fragment 2 amplified with KStrat2_TOP-FW and Kan_to_O-RW1 (384 bp), both fragments from pENTR-D-TOPO.

Figure 2A:
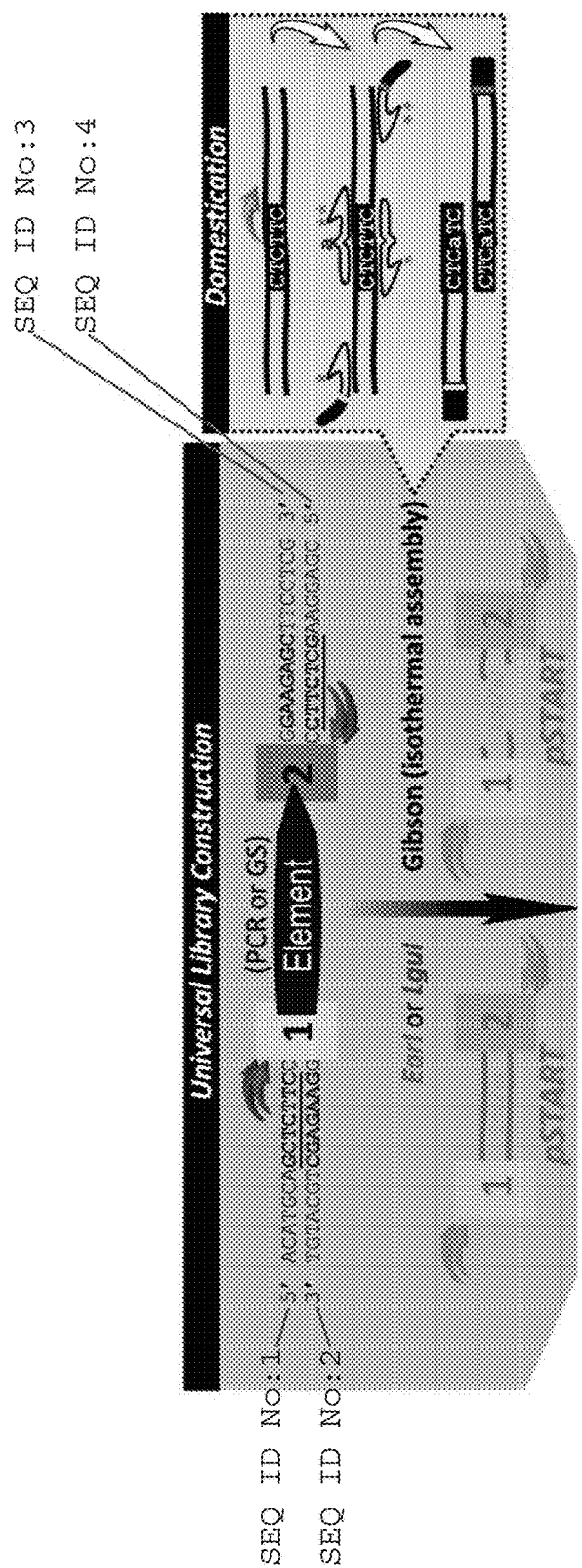
FIGS. 2A-2C. (A) Details of the library construction in the pSTART vector including the domestication process (top) along with the α family of vectors (purple, left) and Ω family of vectors (orange, right). Fragments of interest (element) can be produced by gene synthesis ("GS") or amplified by PCR using the sequence shown (plus the three nucleotide code for signatures 1 and 2) to be inserted in the pSTART vector by either restriction enzymes (EarI/LguI) or "Gibson" isothermal assembly (which requires previous linearization of pSTART, as shown for XmaI). If extrusion of 5'CTCTTC3' sites within the fragment is desired, overlapping oligos carrying a point mutation (e.g., T>A) can be used for amplification (asterisks denote paired primers, one set of primers with single asterisk, another set of primers with double asterisk) and directly used for Gibson assembly with the linearized pSTART (Domestication, top right). pSTART carries signatures 1 (yellow) and 2 (green) used to transfer the fragment from the library to any member of either α family (using EarI, green arrow) or Ω family (using LguI, red arrow). Versions "R" in both families were created to allow fragment reorientation (sense or anti-sense insertion). Signatures 3 (red) and 4 (blue) will be used to join two (only signature 3) or three (both signatures 3 and 4) fragments together (example given in FIG. 2C below). Elements are transferred from Ωs to αs using EarI and from αs to Ωs using LguI. The enzyme setup and the selection markers employed allow for one-pot reactions, which uses up to three plasmids carrying the "inserts" (entry) plus one destination (dest.) vector (either α or Ω member) and for multiple rounds of cloning alternating between α and Ω families (Assembly loop). As an example, a construct using the reporter gene LacZω allows for white/"blue" screening (using either 5-Bromo-4-chloro-3-indolyl β-D-galactopyranoside or 5-Bromo-3-indolyl β-D-galactopyranoside). The sequence presented above the α family (SEQ ID NO: 1) exemplifies LguI (red font) and EarI (green font) restriction sites on either side of signature sequence 1 (acc). Underlined sequence (TCGa) can be methylated by M.TaqI to prevent binding of EarI to the LguI site when using α vectors as entry vectors. This methylation sequence is absent in pSTART and Ω members. The sequence presented above the Ω members (SEQ ID NO: 2) exemplifies LguI (red font) and EarI (green font) restriction sites on either side of signature sequences 2 (gat) and 3 (agt). The GG point mutation created upstream of the EarI site to minimize LguI promiscuity is highlighted with pink background (see also FIG. 13B). (B) Detailed sequence of each signature shown from 5' to 3'. Note that signatures 1R and 2R are the antisense of signatures 1 and 2, respectively. Signatures were chosen based on GC content, adenine positioning to create an M.TaqI site and to avoid stop codons as well as internal starting codons in case multiple CDS are to be joined. (C) Exemplification of a three fragment assembly after cloning the elements Pro, CDS and term in the library (pSTART) as shown in A. Either α or Ω versions 1A, B and C are individually (point 1) used as destination vectors for Pro, CDS and term, respectively, generating the constructs Pro(α/Ω1A), CDS(α/ΩB) and term(α/ΩC) (point 2). All three constructs can now used as entry clones and combined with a new destination vector in one single tube (point 3; any Ω/any α, respectively). Alternatively, the destination vector can be the pSTART, in case a construct is desired as an element in the library. Depending on fragment size, the one-pot reaction (simultaneous restriction and ligation reaction) can be performed with both destination vector and pSTART simultaneously and plated on the appropriate antibiotic to select the destination vector. However, increased efficiency has been observed when entry vectors and pSTART are linearized in advance and ligated in a separate tube. After two rounds of cloning, all three elements were joined seamlessly without the need of adaptors/linkers or homology between sequences. If a fragment is desired to be inverted (anti-sense orientation), the "R" version of the respective destination vector is used (point 4), with no other adjustment needed. Single insert cloning can be done at either 1 h at 34° C. or 25 cycles of 34° C. 45 sec, 16° C. 4.5 min or a regular TNT-reaction (50 cycles of 34° C. 45 sec, 16° C. 4.5 min). If the destination vector is linearized in advance, the tertiary assembly can also be performed in as little as 1 h at 34° C., albeit with somewhat reduced efficiency compared to a regular TNT-reaction.
Figure 2A:
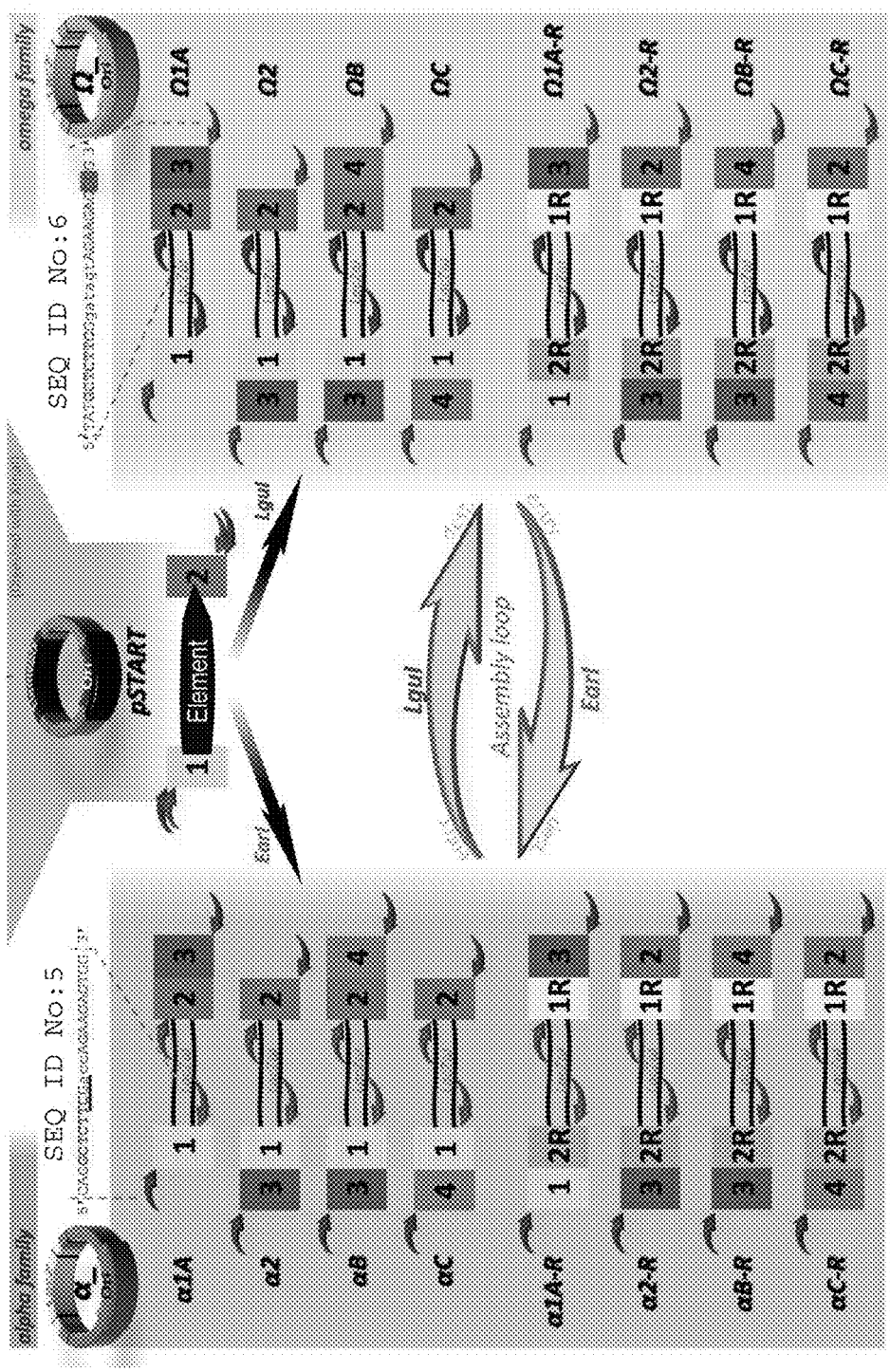
Figure 2B:
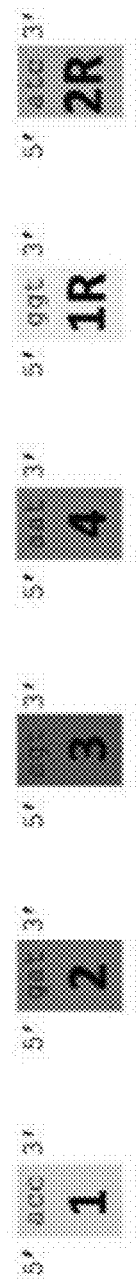
Figure 2C:
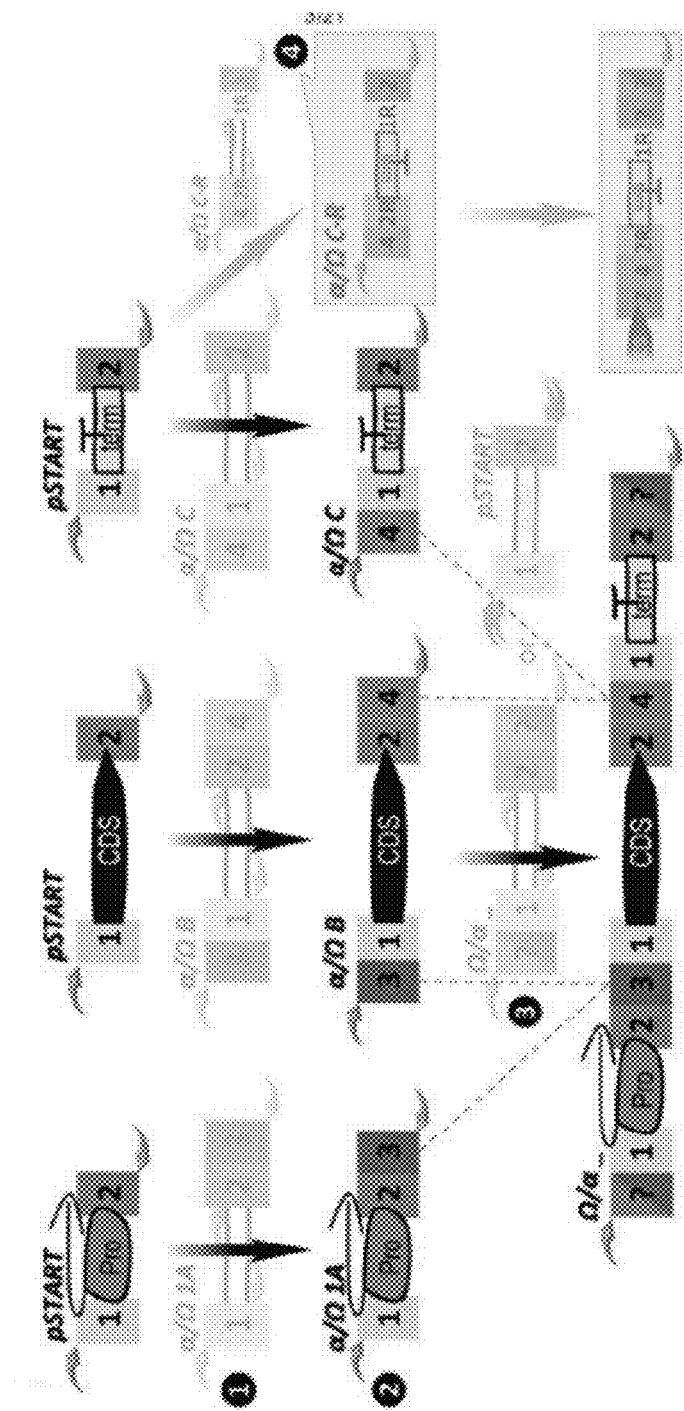
Figure 13A:
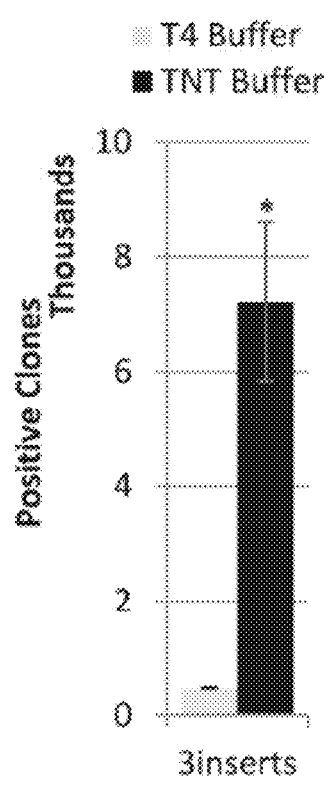
FIGS. 13A-13B. Cloning efficiency of T4DNA Ligase buffer, TNT-Buffer and two different versions of Ω vector with upstream point mutations. (A) Three fragments assembly from both ways reactions (α's to Ω's and vice-versa) using either T4 DNA ligase buffer (T4 Buffer) or TNT-Buffer (0.5-2% a PEG-PPG-PEG block copolymer). Error bars are from 3 independent cloning reactions (p=0.01, t-test). Number of clones shown are positive clones confirmed by colony PCR (16<n<32) and are a maximum number possible per reaction estimated from the small aliquot used for transformation and plate counting. Same lot of competent cells was used. The T4 Buffer and TNT Buffer results were performed using the GoldenBraid (6 h) and TNT-reaction (4.5 h) standard protocols, respectively. Ωs used here were version 5'aaCTCTTC3'. (B) Optimized nucleotide sequence upstream of EarI site to minimize unspecific cleavage by LguI. Previously, most clones obtained from tertiary assembly reactions were unspecific transfer of one fragment from α1A to Ω1A, which represents unspecific cleavage of LguI at the EarI site exposing the signature number 3 of Ω1A rather than signature number 2 for proper cloning of the final tertiary construct. Therefore, three new point mutations were tested at the 5' end of EarI site. The best result is shown here, for sequence 5'ccCTCTTC3' where more than 2000% increase in cloning efficiency were observed compared to the previous Ω version 5'aaCTCTTC3' (p=0.001, t-test, n=4). This sequence were implemented in all Ω members at sites that bear 2 signatures side by side and represent the final set of Ω plasmids.
Figure 13B:
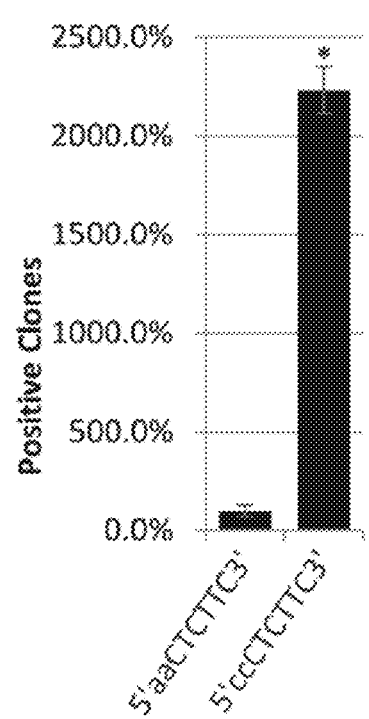

The Ω vectors had point mutations introduced, as reviewed in FIG. 13B. These vectors were adjusted by linearizing the vectors with PstI or PmeI, partially digesting with LguI for assembling with a double strand oligo (named leftCC-FW/RW or rightCC-FW/RW) covering the same sequence (positions 83-142 bp, when PstI was used, or 3328-3394 bp, when PmeI was used) with the point mutation from 5'aa to 5'cc being located at positions 108-109 bp and/or 3361-3362 bp (Ω1A versions 5'tt and 5'gt at the 3361-3362 bp positions were also created and tested, data not shown). Importantly, this change was performed on all versions, however, only at those sites that bear two signatures side-by-side (FIG. 2A).

Figure 3:
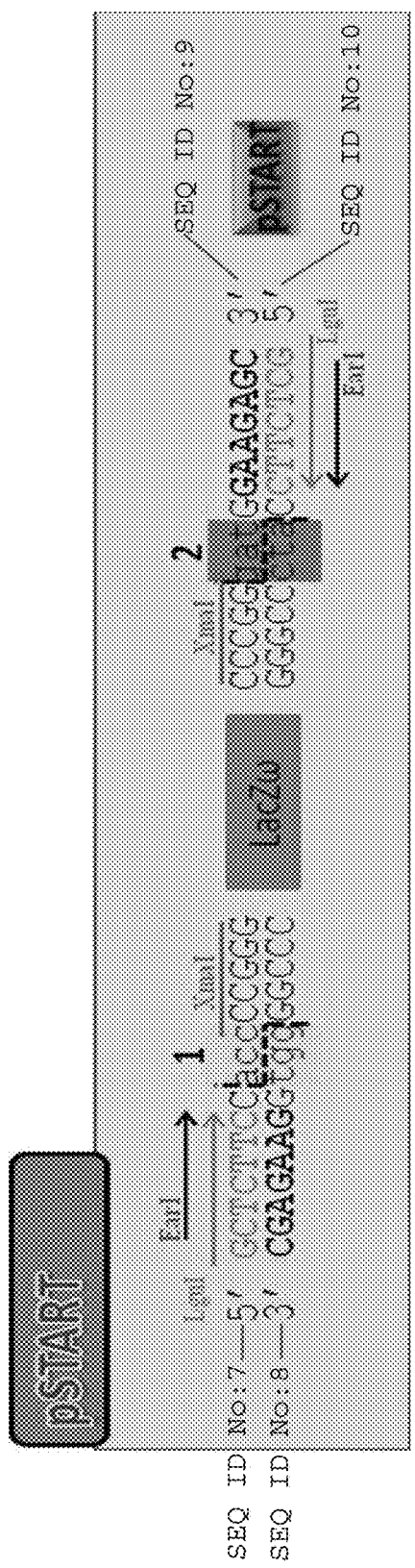
FIG. 3. pSTART vector design. LguI (GCTCTTC) and EarI (CTCTTC) binding sites are shown (arrows). Cleavage site is indicated by a dotted line (generates cohesive ends; not present at sites where two signatures are placed side-by-side). Note that the cohesive ends generated represent each signature used for joining DNA pieces and are restored upon fragment ligation. However, the enzyme binding site is discarded (stays in the unwanted vector backbone) allowing for future rounds of cloning using the same enzyme set.

The vectors αB-R, αC-R, ΩB-R and ΩC-R were implemented by digesting the α1A and Ω1A vectors at the PstI and PmeI sites and assembling the purified backbone to three GBlock fragments, having one in common (LacZω-central-gb) and the remaining specific for each vector created (alphaBR-gb left, alphaBR-gb right, alphaCR-gb left, alphaCR-gb right, omegaBR-gb left, omegaBR-gb right, omegaCR-gb left, omegaCR-gb right) by Gibson assembly. All vectors created without exceptions had the signatures confirmed by sequencing before undergoing tests. Primers pUPD-seqFW and pUPD-seqRW (for pSTART) or primers TNT-αΩ-seqFW and TNT-αΩ-seqFW (for any α and Ω members) were used to sequence inserts and diagnose constructs by colony PCR. Entry elements used for testing as shown in FIG. 3 were either amplified from general templates (green fluorescent protein, TNT-GFP-FW/RW; PIP2 fused to mCherry, TNT-PmCherry-FW/RW; 35S promoter, TNT-35SProm-FW/RW; and 35S terminator, TNT-35STerm-FW/RW) or dimerized (100 pmol in 50 µl of 1×PCR buffer for 95° C. 5 min and then 85° C. to 45° C. every 5° C., 5 min each) using FW and RW primers (Lumio_tag, NLS, P2A, T2A, F2A and Ibp) before being assembled (1 µl of dimerized oligos) in the pSTART by Gibson assembly. Primers used to clone other elements tested in our entry vector pSTART, but not used further in this work, are listed for reference (TNT-Cas9-FW/RW1-5, partial domestication; GUS reporter, rGUS-FW/RW; 35S:: hygromycin-F2A-CodA-Terminator, HCC selectable marker, Hig-CodA-FW/RW; Luciferase reporter, Luc+_pUPD_FW/RW; DNA 2.0 CPB-38-441 vector, CircRep-FW/RW).

Library Construction (pSTART) and Constructs Diagnosis

Primers to clone fragments by either restriction/digestion or Gibson assembly were designed as 5'ACATGCAGCTCT-TCC<u>ACC</u>N$_{(20)}$3' (SEQ ID NO: 273) where N is the fragment of interest sequence forward (signature 1 is underlined) and as 5'CGAGGAAGCTCTTCC<u>ATC</u>N$_{(20)}$ (SEQ ID NO: 274) for reverse strand (signature 2 is underlined), as long as TM of N$_{(20)}$>50° C. Otherwise, number of base pairs was increased over 20 nt until at least 50° C. of TM was reached (using analyzing calculator available online at idtdna website). Multiple PCR products were purified and combined by Gibson assembly. All PCR reactions were performed using Phusion DNA polymerase (Thermo Scientific) according to suggested protocol (DMSO was added accordingly if amplicon was longer than 1.5 kb). Qiagen TAQ DNA polymerase diluted 10 fold was used for diagnosis through colony PCR and the remaining settings were according to suggested protocol. Briefly, colonies were picked from the agar plate and diluted in 10 µl of water in 96 well plates and 1 µl was used for PCR in 10 µl final volume. TM used was always 56° C. for 20 sec and extension was always 72° C. for 1 min; always 40 cycles. Positive clones had the remaining 9 µl (5 µl if colony PCR was performed in parallel to culture growth) inoculated in appropriate media (LB+chemicals). Every insert in the library was sequenced. First levels of complex assemblies shown in FIG. 12 were fully sequenced. Clones also checked by restriction digestion are noted in the text.

Detailed Assembly Steps for Constructs Involved in the Proof-of-Concept

First, at the α-level, the GFP was transferred from the library (pSTART) to αB and the NLS to α1A and αC. These clones were joined in a tertiary assembly in Ω1A generating the NLS-GFP-NLS (Ω1A) construct. Secondly, at the Ω level, the 35S promoter (35S), the Lumio tag (Tag) (Invitrogen), the PIP2 fused to mCherry (PmCherry), different versions of the SS (SSP1, SSP2) and the 35S terminator (Term) were transferred to Ω1A, ΩB, ΩC, Ω1A/Ω2 and ΩC, respectively. Third, again at the α level, the 35S (Ω1A), Tag (ΩB) and PmCherry (ΩC) were joined in a tertiary assembly in α1A generating the construct 35S::tag-PmCherry (α1A); the SS1 (Ω1A) and SS2 (Ω2) were joined in a binary assembly in αB generating the construct SS1-SS2 (αB); the NLS-GFP-NLS (Ω1A), Tag (ΩB) and Term (ΩC) were joined in a tertiary assembly in αC to generate the construct NLS-GFP-NLS-tag-Term (αC). Finally, again at the Ω level, the 35S::tag-PmCherry (α1A), different combinations of the SS1-SS2 (αB) and the NLS-GFP-NLS-tag-Term (αC) were joined in a tertiary assembly in different Ωs generating the construct 35S::tag-PmCherry-SS1-SS2-NLS-GFP-NLS-tag-Term, where SS1-SS2 means P2AF2A (ΩB), P2AT2A (Ω1A) or IbpF2A (ΩC) (different peptide 2A; *Impatiens* *balsamina* peptide, cleaved in plants). In parallel, the 35S:: tag-PmCherry (α1A) and NLS-GFP-NLS-tag-Term (α2) were joined in a binary assembly in WA generating the 35S::tag-PmCherry-NLS-GFP-NLS-tag-Term (Fused control). Lastly, 35S (Ω1A), NLS-GFP-NLS (ΩB) and Term (ΩC) were joined in a tertiary assembly in α1A generating the 35S::NLS-GFP-NLS-Term (α1A) (GFP control); the 35S::tag-PmCherry (α1A) and Term (α2) were joined in a binary assembly in Ω1A generating the 35S::tag-PmCherry-Term (Ω1A) (PmCherry control).

GenBank Accessions for pSTART Entry Clones

Sequences were submitted to GenBank and a submission ID was generated by BankIt for the following pSTART vectors: d35S_h-h, PmCherry, Lumio, RGR gene, P2A, T2A, Cas9*, F2A, Ibp, GFP, 35SProm, 35STerm, NLS, NosProm, GUS, HCC (Hig-CodA, see methods), Kan-ORF, 8m1*, 7m1*, 5m2*, 4m1*, CircRep.

Methylation Tests

Type II cytosine-5 DNA methyltransferase protein sequence from *Streptomyces achromogenes*, which recognizes and modifies the sequence 5'GAGCTC3' (M.SacI; GenBank AAC97118.1), was reverse translated, synthesized (Table 1), cloned in pET28 (pET28-M.SacI) by Gibson assembly (NcoI-SalI sites), transformed in T7Express and induced according to vector/strain suggested protocol (4 h, 0.5 mM IPTG). Expression of the ≈43 kDa protein was confirmed by protein gel and a second fraction of the same culture had the pET28-M.SacI plasmid extracted, quantified and 1 µg was subject to incubation with BspQI, LguI, SapI or EarI in duplicates on manufacturer recommended buffer. Digestion ran for 1 h at 37° C. (except for BspQI, where 50° C. were used) using 5 U of each enzyme (except SapI, where 10 U was used) in 20 µl reaction volume. The reactions were stopped and loaded in agarose gel. Bands were quantified by ImageJ software (area tool after plotting lanes) and organized using Excel. A non-methylated control was always included, and for M.SacI and M.TaqI sites non-subjected to methylation inside each tube, were also used to guarantee full restriction enzyme activity. "Digestion inhibition" was a direct measurement of the digested bands divided by total band intensities (digested plus non-digested) and "Methylation efficiency" was calculated by 1 minus "Digestion inhibition".

Figure 11A:
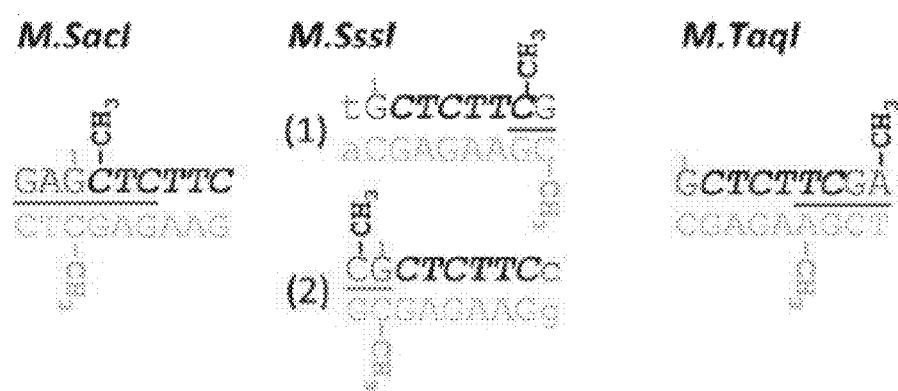
FIGS. 11A-11D. EarI sensitivity to methylation. (A) Methylases studied with their respective binding sites (underlined) and targeted residues (—CH$_3$) on forward (black) and reverse (gray) strands. The EarI recognition site is indicated in bold/italic and position number 1 of the 5'GCTCTTC3' site is indicated in gray numbering. (B) Agarose gel showing methylation-dependent inhibition of EarI activity. Left panel: M.SacI was expressed in *E. coli* T7Express (T7X) and the expression plasmid carrying the site shown in A (pET28-M.SacI) was subjected to EarI digestion. Sensitivity is expressed by accumulation of the 1557 bp band (1309 bp+248 bp). Middle and Right panels: distinct 1055 bp PCR products carrying each site shown in A (M.SssI-1 or M.TaqI, respectively) were methylated in vitro and subjected to EarI digestion. Sensitivity is expressed by accumulation of the 700 bp band (450 bp+250 bp). Images are representative of duplicated experiments. (C) Gel bands of each replicate described in B were quantified and expressed as percentage: 1-[digested/(digested+ linearized)] in each tube. Mock is average of non-methylated DNAs (n=6) and bars are standard error. Non methylated sites in the same molecule showed the digestion was >97% completed in each tube. (D) Methylation efficiency of 5,291 bp (M.Test) vector in vivo by T7X.MT (which carries the TaqI methyltransferase in the genome) compared to control (same vector in T7X) and in vitro data (M.TaqI; similar to C but new replicates). T7X.MT carrying the plasmids were selected on plates supplemented with 0.3 mM IPTG and grown overnight at 37° C. in liquid media+0.2 mM IPTG for 14-18 h before DNA extraction. Bars are standard error of four biological replicates and graph is a representative image of a duplicated experiment.
Figure 11B:
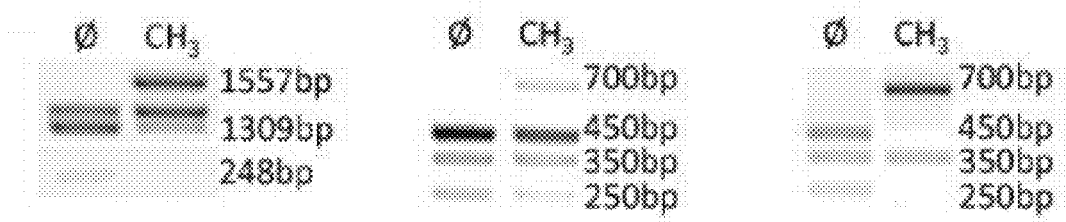
Figure 11C:
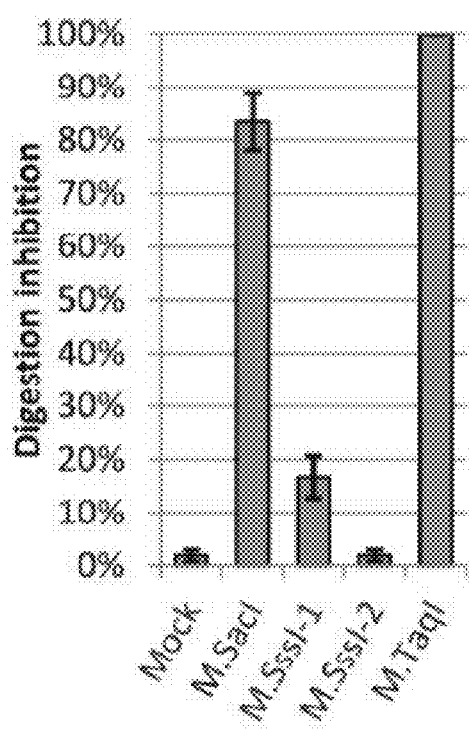
Figure 11D:
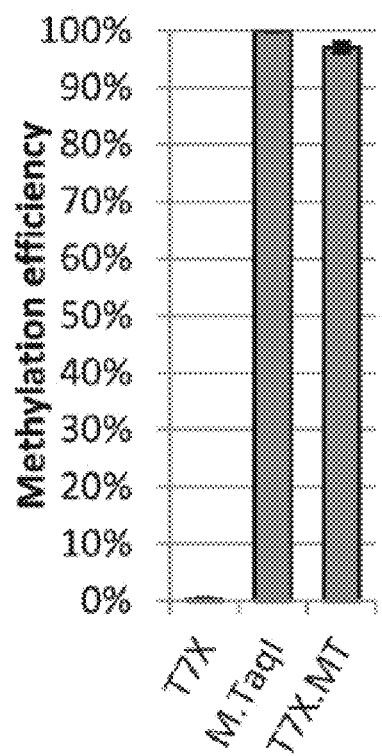

For M.SssI assays, a 1055-bp PCR product, using the pET28-M.SacI plasmid as template, was amplified (using the primers TaqI-Fw and TaqI-Rw), purified, quantified and incubated with methyltransferase as manufacturer instructions (NEB). In this case, there are 92 sites for M.SssI (5'CG3'), which counts for ≈25 µM of substrate in a 20 µl reaction if 1 µg of DNA, was used. In this case, to achieve complete methylation, 1 µl of enzyme (4 U) is recommended by the manufacturer to fully methylate 4 µg of such template in 20 µl reaction supplied with 640 µM SAM for at least 2 h at 37° C.; our reactions ran for 4 h under these conditions. Methylated DNA was purified and 400 ng used for type IIS assays in duplicates and "Digestion inhibition" and "Methylation efficiency" were addressed as described above. Both sites shown in FIG. 11A are present simultaneously in the fragment and could be addressed in the same reaction by selecting the appropriate bands for quantification. For M.TaqI assays, two PCR products using the pET28-M.SacI plasmid as template were obtained (using the primers TaqI-Fw and TaqI-Rw1.1 and TaqI-Fw1.1 and TaqI-Rw), purified, quantified, diluted at least 1000 fold and mixed together in an equimolar ratio for a secondary PCR (30 cycles) using only TaqI-Fw and TaqI-Rw to generate the 1055 bp fragment with an internal M.TaqI site as shown on FIG. 2. The 1055-bp secondary product was then purified, quantified and incubated with methyltransferase as manufacturer instructions (NEB; except we increased incubation time to 4 h). Methylated DNA was purified and 400 ng used for type IIS assays in duplicates and "Digestion inhibition" and "Methylation efficiency" as described above. After the screening in duplicates, the M.TaqI results were confirmed by other 4 biological replicates for EarI only (FIG. 11D).

For in vivo assays, using M.Test plasmid transformed in T7X.MT in liquid LB media, two separate colonies were plated for each of the following conditions: IPTG concentration during the liquid growth (0 mM, 0.2 mM or 0.5 mM); presence (0.3 mM) or absence of IPTG in the plate during transformation with M.Test plasmid; and presence or absence of a heat shock treatment for 1 h at 50° C. right before DNA extraction. The best condition was found to be cultures grown on plates with 0.3 mM IPTG right after original transformation and 0.2 mM of IPTG on liquid media overnight grown at 37° C. These conditions were reproduced for other 4 new colonies. Experiment was later reproduced once, with 3 biological replicates and M.Test DNA was then kept at −15° C. and re-accessed after 3 weeks and after 11 weeks, in which Eam1104I was also included.

TNT-Buffer and the Standard TNT-Reaction

Figure 12A:
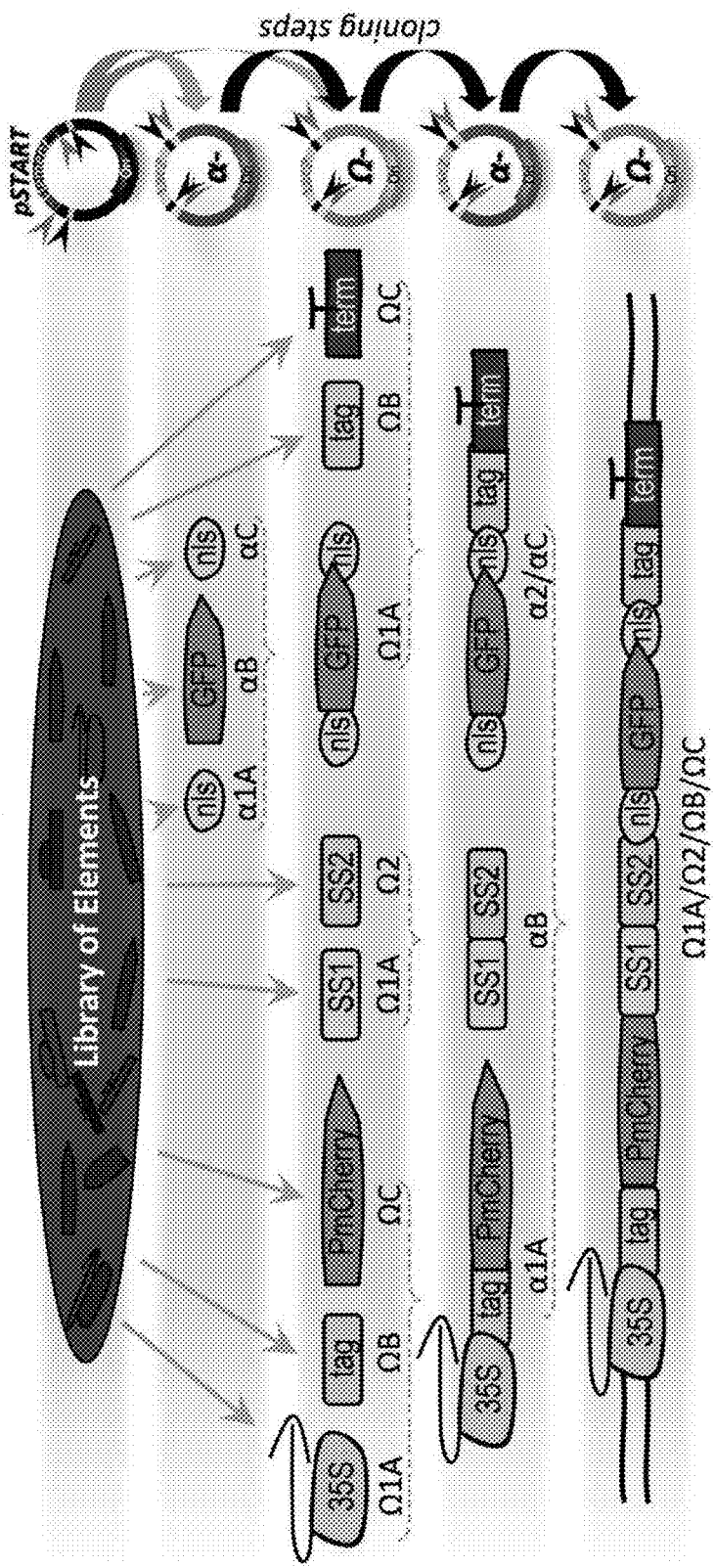
FIGS. 12A-12E. TNT-cloning system proof of concept. (A) Scheme of elements joined. Ten different fragments were joined by binary and tertiary assembling in different "α" and "Ω" vectors: 35SPromoter (35S), lumio tag (Tag), PIP2mCherry (PmChery), different 'self-splicing' protein (SS1 and SS2; to be different combinations of the viral proteins P2A, F2A and T2A and the plant protein Ibp), nuclear localization signal (NLS), GFP (GFP) and 35S terminator (Term). Each line represent one level of assembly with the respective vector used as scaffold (either α or Ω) shown underneath each fragment and in the right (black and pink arrows are enzymes biding and cleavage sites, respectively). Elements are first transferred from the library (pSTART) to either α or Ω vectors (gray arrows) before binary/tertiary assembly (black arrows). (B) Confocal image of constructs built. The final constructs without (Fused) or with different sets of SS proteins (P2AF2A, P2AT2A and IbpF2A) were infiltrated in tobacco leaves and a representative image is shown for each construct. The membrane localized PmCherry and nuclear GFP controls in separate vectors were co-infiltrated and represent a "maximum split" reference to normalize and evaluate the mCherry and GFP fluorescence from each SS construct. The fused proteins are localized in the nucleus, but efficient cleavage of different SS-dimers allow for proper protein localization. At least one hundred cells were visually scored for mCherry and GFP fluorescence separation in each construct. Scale bar in each panel is 10 μm. Signals were captured at a reduced window spectrum for GFP (493-556 nm) and mCherry (578-650 nm). (C) Representative breakdown of mCherry (red) and GFP (green) fluorescence across a nuclei section (10-18 μm) showing the separation range between both channels. P2AF2A (99.7% SE±1.2, n=11) and P2AT2A (94.2% SE±2.8, n=15) showed the best separation of non-overlapping signals, against the partial separation observed for IbpF2A (79.7% SE±8.4, n=11) and the Fused control (6.4% SE±1.2, n=8) (all related to the Non-Fused control taken as 100% SE±1.2, n=8). P2AF2A and P2AT2A are not significantly different from Non-Fused control while IbpF2A is different from both Fused control (p<0.001, t-test) and Non-Fused control (p=0.036, t-test). Double bars separate a 3 fold difference zone. (D) Agarose gel showing the EarI digestion (left panel) of panel B constructs: P2AF2A (4069 bp), P2AT2A (4009 bp), IbpF2A (4066 bp) and Fused control (3883 bp). Right panel (LguI digestion) shows two independent colonies randomly picked for a total of 28 fragments joined in a 12 kb (12036 bp) construct, product of tertiary assembly of Fused control, P2AF2A and IbpF2A in α1A. ND, non-digested; M, 24 kb Max DNA Ladder; asterisks indicate vector backbone for α (purple) and Ω (orange). Arrows are inserts released. (E) Cloning efficiency using TNT-buffer and other cloning methods available. Ability of TNT-cloning system to produce the desired clone was determined by comparing the transfer and joining of one insert to the ability of the T4 DNA ligase buffer to join the same fragments (size were between 0.25-2.4 kb) or the LR reactions from the gateway system and the isothermal (Gibson) assembly to join similar fragments (both require overlap/homology between sequences). In addition, joining of two and three inserts was measured by the isothermal (Gibson) assembly and TNT-buffer (fragment sizes were between 0.8-4 kb). Between 4 and 7 biological replicates were used in each condition representing both way reactions (from α towards Ω and vice-versa). For TNT-Buffer using 3 inserts, data include both Ω's (aaCTCTTC and ccCTCTTC) Number of clones shown represent positive clones confirmed by colony PCR (16<n<32) and are a maximum number possible per reaction estimated from the small aliquot used for transformation/plate counting. Same lot of competent cells was used (efficiency ≈10$^9$ cfu/μg of Puc19 plasmid). TNT Buffer results were performed using the one-pot standard TNT-reaction (50 cycles of 34° C. for 45 sec and 16° C. for 4.5 min) and the T4 Buffer results were performed using either the one-pot TNT-reaction or the one pot GoldenBraid standard 6 hours protocol (50 cycles of: 34-37° C. for 2 min and 16° C. for 5 min). Asterisk: t-test from T4 Buffer, *p=0.02, p=0.002, or from Gateway p=0.02.
Figure 12B:
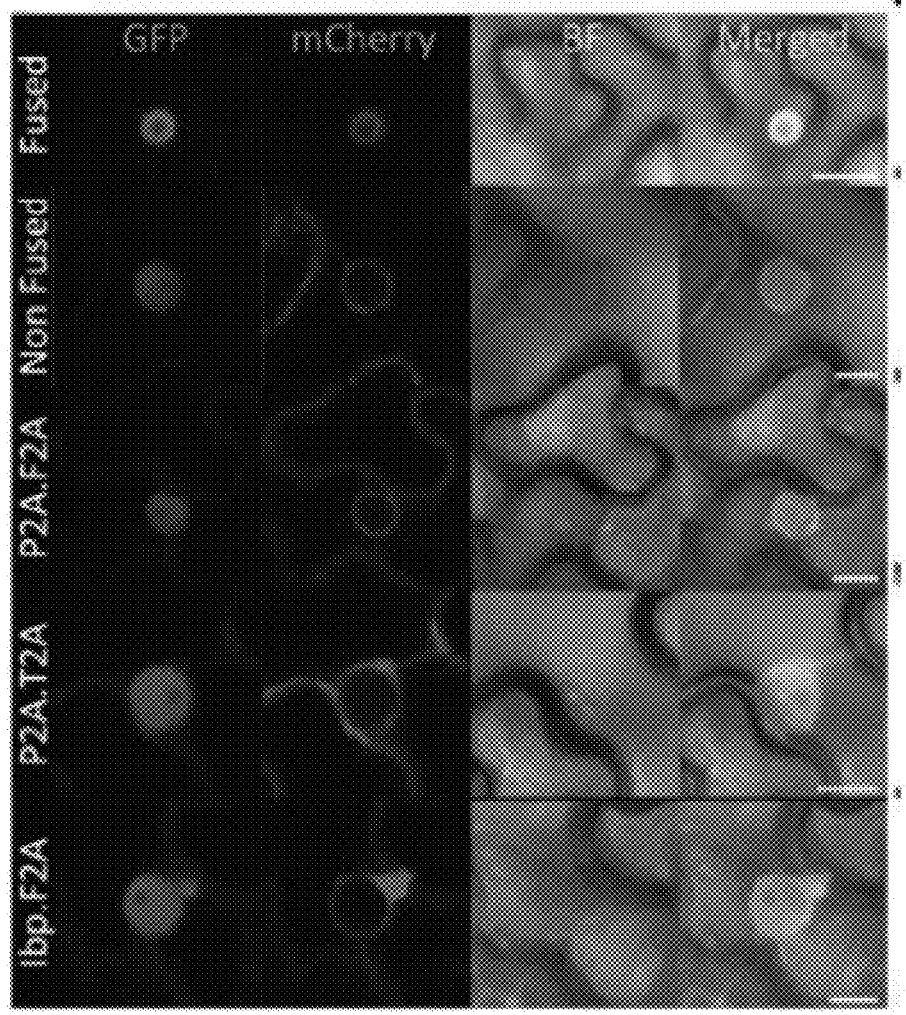
Figure 12C:
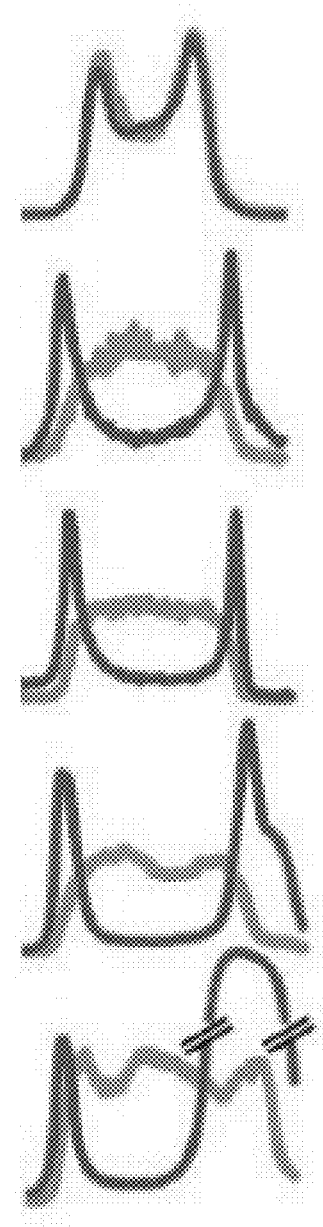
Figure 12D:
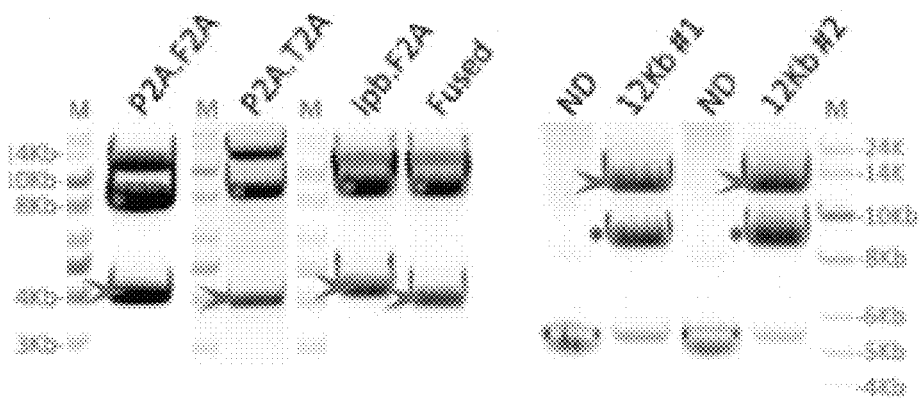
Figure 12E:
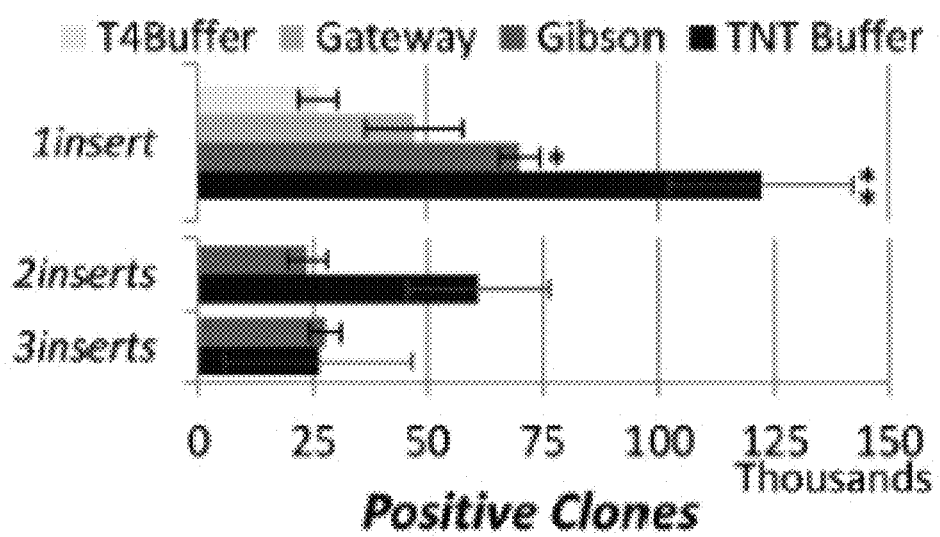

We tested several conditions for BspQI, EarI, LguI and SapI enzymes in order to tune our "one-pot" reaction conditions. We found the 10 mM DTT from T4 DNA ligase buffer sufficient to inhibit EarI activity and that excessive amounts of NaCl (>50 mM) inhibited LguI. BSA in a reaction increased the number of false positives (data not shown). We found the best DNA concentration to be ≈75 ng (75 ng each for three fragment assembling) insert plasmid(s) at the range of 0.25-2.5 kb and ≈50 ng of TNT-members α, Ω or pSTART. We found that inclusion of PEG-PPG-PEG [poly(ethylene glycol)-block-poly(propylene glycol)-block-poly(ethylene glycol)] (Sigma-Aldrich, Inc., catalogue #435406) increased the number of positive colonies and allowed us to reduce the incubation time for digestion/ligation while keeping higher efficiency than the T4 DNA ligase buffer (FIG. 12E). Preferred concentration of PEG-PPG-PEG is between 0.5% and 2%. This "TNT-Buffer" has the following formulation: 50 mM Tris-HCl (pH7.5), 2 mM DTT, 10 mM $MgCl_2$, 1 mM ATP and 2% PEG-PPG-PEG (which was added right before reaction setup from a 20% stock in water). We also found the enzyme concentration to be extremely important especially for accuracy (number of positive clones) and a standard TNT-reaction, set up on TNT-Buffer, includes 40 U of T4 DNA ligase and either 5 U of EarI or 0.5 U of LguI, followed by incubation of 34° C. for 45 sec and 16° C. for 4.5 min for 50 cycles. If only one fragment is being cloned (or linearized destination vector is used for tertiary assemblies) reaction can be performed at 34° C. for 1 h, albeit number of positive clones is reduced. All reactions were performed in 10 μl final volume and diluted 1-10 fold or 1-50 fold when α or Ω members were used as destination vectors, respectively, before taking 1 μl to transform electrocompetent cells.

BlindSpot Protocol for Cloning Non-Domesticated Fragments

For non-domesticated fragments, a regular TNT-reaction was used for single fragment cloning. For binary and tertiary assemblies involving non-domesticated fragments, we developed a protocol, which we call the BlindSpot protocol, as follows: fragments (≈150 ng each rather than ≈75 ng each) were first incubated with 50 μM oligo (design details below) for 1 h in each temperature 45° C. to 12° C. every 3° C., usually overnight, in an alternative buffer (50 mM Tris-HCl pH 5.8, 75 mM NaCl, 10 mM $MgCl_2$, 2 mM DTT) in 4 μl final volume. Following the addition of 6 μl of a second buffer (50 mM Tris-HCl pH 6.3, 10 mM $MgCl_2$, 2 mM DTT) and either 5 U of EarI (for 5 min, ≈60-65% digestion progress) or 1.5 U of LguI (for 15 min, 255-65% digestion progress) the reaction volume was incubated at 25° C. before being directly heated at 80° C. for 20 min. After cool down, 2 μl were used to set up a standard TNT-reaction using either T4 DNA ligase buffer or TNT-Buffer. For the initial screening and digestion curve (FIG. 14B), several incubation times for digestion were used and reactions were stopped with loading dye (NEB), loaded on agarose gel and analyzed similarly to what is described for the methylation assay. Since the control samples, which carry a non-domesticated fragment incubated without oligo, showed some positive clones (FIG. 14E, NoDom), a partial digestion in these conditions was determined to be sufficient to generate the desired construct, reducing the time frame from ≈12 h (if incubation with oligo is performed) to ≈1 h.

Figure 14A:
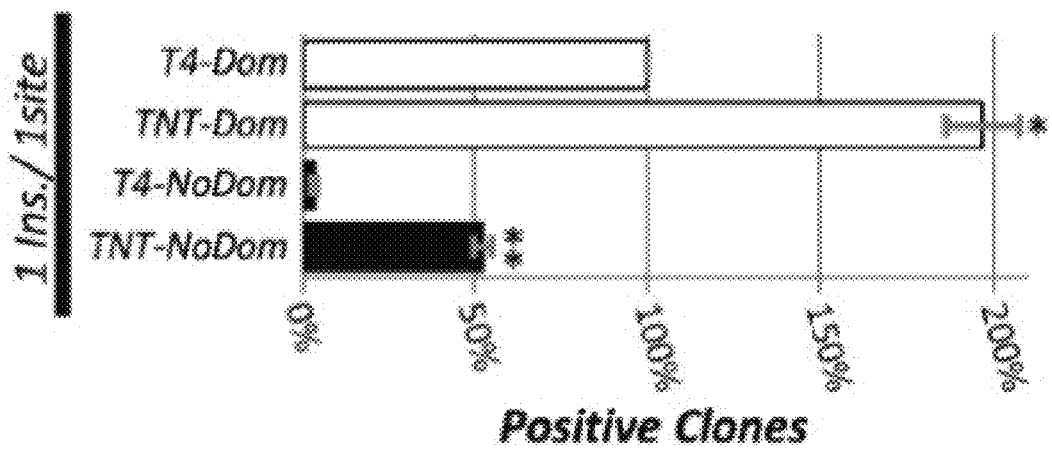
FIGS. 14A-14E. Strategies for overcoming the domestication step. (A) Ability of the T4-Buffer and TNT-Buffer to successfully clone fragments with no domestication (NoDom) and with domestication (Dom; 7m1 template) internal 5'GCTCTTC3' sites. One insert is shown and represents LguI-dependent reactions (from pUPD to Ωs). For Dom fragments (7m1 template), 100% of clones retrieved were positive in both buffers. For NoDom fragments with 1 internal site (8m1 template), T4-Buffer retrieved 62% (SE±8.8) of positive clones while TNT-Buffer retrieved 84% (SE±6.6) of positive clones. Number of positive clones is related to the T4-Dom considered as 100%. T4-NoDom bar corresponds to 3.3% (SE±0.7) and TNT-NoDom bar corresponds to 52.3% (SE±2.6) of the T4-Dom (100%). T-test is related to T4-Dom, p≤0.05(*), p≤0.01(**). Standard TNT-reactions were performed in both panels (50 cycles of 34° C. for 45 sec and 16° C. for 4.5 min) in triplicates (covering 0 members 1A, B and C) and graphs are a representative image of a duplicated experiment. (B) a. Scheme showing the DNA double helix carrying the 5'GCTCTTC3' site (green line) with the respective cleavage site (dotted line in forward strand) with the 26-nt DNA-oligonucleotide expected (orange), without oligo (no N.O.), or not expected (faint orange) to form the triple helix. The duplex 8m1 without oligo (black box), duplex 8m1+oligo (dark red box) or duplex 4m1+oligo (pink box) are indicated. Oligo represent a full match to the duplex 8m1 and a partial match to the duplex 4m1 (mismatches are represented by dotted line in the reverse strand). b. Graph showing the digestion progress over time, in the linear range, using the duplex 8m1 without oligo (black line), duplex 8m1+50-μM oligo (dark red line; potential triplex) or duplex 4m1+50-μM oligo (pink line). The oligo specifically delays the digestion of the desired 5'GCTCTTC3' sites. Lines are linear trend ($R^2$ value is shown) of ten (N.O.) and five (8m1 and 4m1) time points done in duplicates. (C) Gel image showing the digestion inhibition in the 8m1 (left; 45.4% SE±0.9) and 4m1 (right; 9.8% SE±0.5) duplexes (180 ng of a 675 bp PCR product) in the presence of the 26-nt oligo (50 μM), both at 64.3% (SE±1.1) digestion progress (shown in Bb). Inhibition keeps the 675 bp band intact. 50 μM represents the 4m1 template incubated with the 26 nt-Acr oligo (inhibition=48% SE±4.2). (D) Scheme of a "BlindSpot" protocol. Oligos were incubated with appropriate plasmid DNA carrying 8m1 (NoDom) fragments and subjected to partial digestion, ligation to linearized vector and transformation into E. coli. Colonies were then counted, confirmed for positive clones and recorded. (E) a. Results from a BlindSpot protocol showing the number of positive clones obtained upon cloning of the fragments 7m1 (Dom), 8m1 without oligo (NoDom) and 8m1 plus oligo (NoDom+Oligo). NoDom+Oligo is significantly different of NoDom, p=0.005, t-test. 100% refers to number of colonies (gray background bar) that retrieved positive clones. Oligos inhibit digestion at desired 5'GCTCTTC3' site while keeping vectors' 5'GCTCTTC3' accessible to enzyme. b. Results from a BlindSpot protocol showing the number of positive clones obtained for a tertiary assembling joining three different domesticated fragments (Dom) and one independent fragment plus two copies of 8m1 (which represents 4 internal 5'CTCTTC3' sites) without (NoDom) or with (NoDom+Oligo) the 26-nt oligo (100 μM). Percentages refer to number of colonies (gray background bar) that retrieved positive clones (NoDom+Oligo is significantly different from NoDom, p≤0.001, t-test). Ligation was performed using T4-Buffer in both panels. Error bars are from three biological replicates and graphs are a representative image of two independent experiments.
Figure 14B:
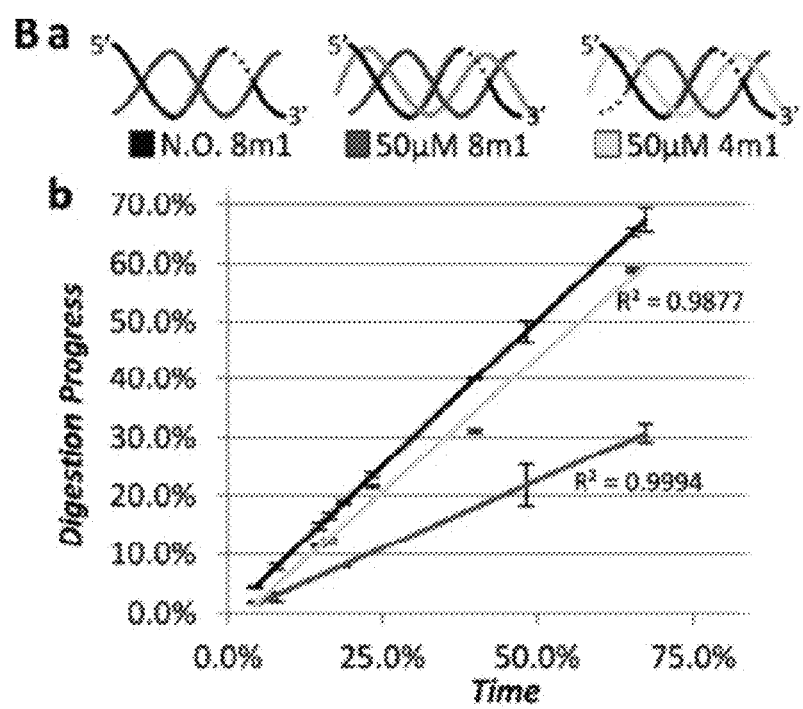
Figure 14C:
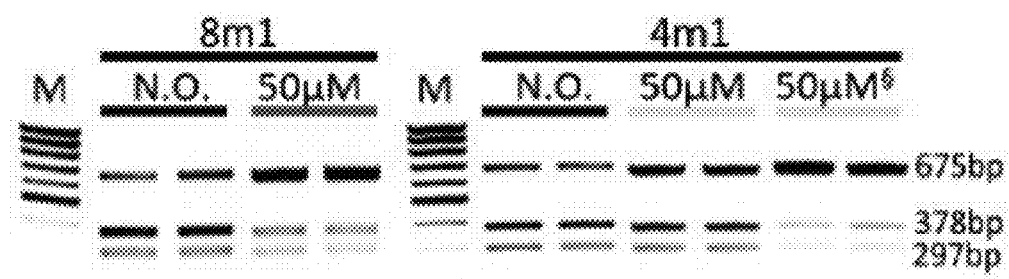
Figure 14D:
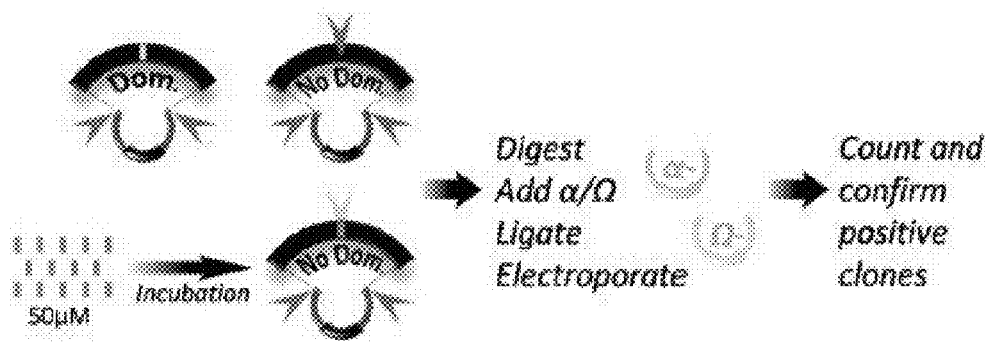
Figure 14E:
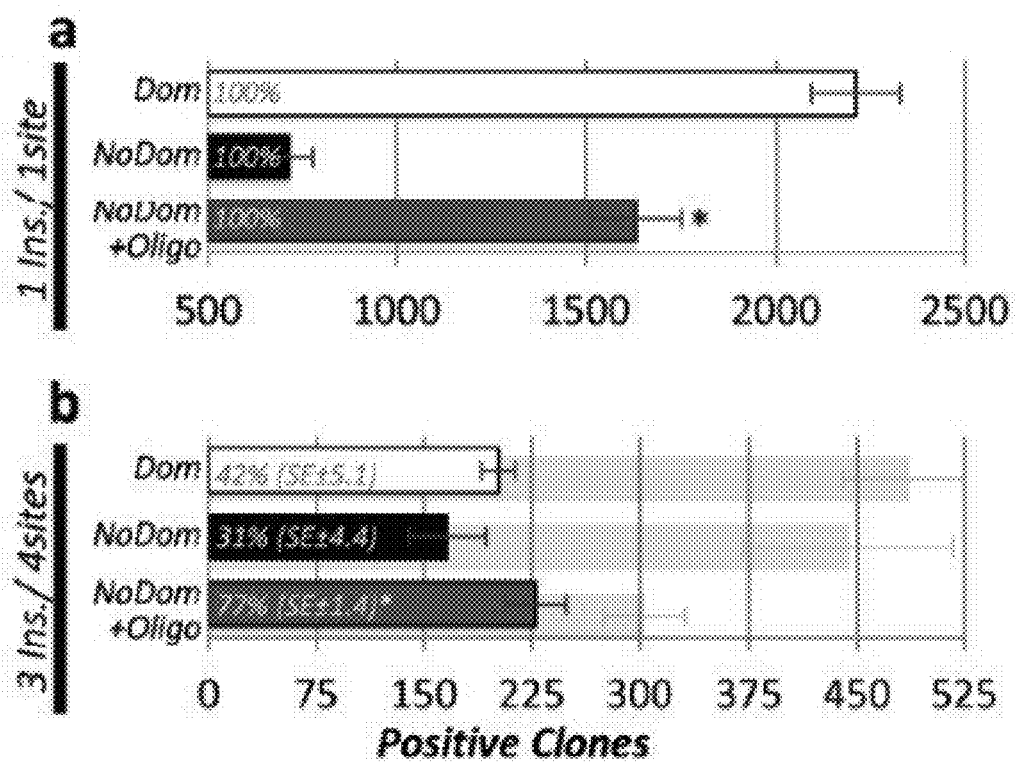

Efficient inhibition was not seen with 15 nt and 22 nt oligonucleotides designed in both directions (15 ntW-H.T-FOs1, 22 ntW-H.TFOs1, 15 ntRvH.TFOs1, 22 ntRvH.T-FOs1, 15 ntW-H.TFOs2, 22 ntW-H.TFOs2, 15 ntRvH.T-FOs2, 22 ntRvH.TFOs2, data not shown). However, we were able to show that an oligo designed to cover 11 nt upstream of LguI/EarI site and 8 nt downstream (which covers the cleavage site) in the same orientation as the 5'GCTCTTC3' site (if the sense sequence gives the 5'GAAGAGC3', use the anti-sense sequence for designing the oligo) inhibited both enzymes (FIG. 14E). The standard 14 nt Acridine-DNA/$BNA^{NC}$ oligo (Bio-Synthesis Inc., Lewisville, Tex.), with higher TM (82.5° C.) and 26RvH.DNAsyn8mDW-Acridine3', showed efficiency but not specificity during the inhibition. Our experiments were performed using 1 μl of 200 pmol oligo (50 μM in 4 μl reaction) or 2 (100 μM in 4 μl reaction) when 4 sites were tested (FIG. 14E). Clones were checked by colony PCR (16<n<32) for statistical analysis and different patterns in the gel were digested and sequenced to confirm gene structure.

Statistical Analysis

Statistical analysis were performed in Microsoft excel, first, running a F.TEST function that retrieve the two-tailed probability that the variances in Array1 and Array2 are not significantly different. Then, if F-test p≤0.05, two-tailed t-test function were ran as type 2 (equal variance); if F-test p>0.05, two-tailed t-test function were ran as type 3 (unequal variance). Only t-test p values are shown.

Calculating Need of Mutagenesis

Due to differences in the specificity of the inhibition for EarI and LguI during the BlindSpot protocol in different mismatches range, we considered a minimum mismatch of 35% and 15%, respectively, between the target site (intended to be protected) and the consensus sequence (11 nt upstream and 4 nt downstream) surrounding the 5'GCTCTTC3' site in our TNT-plasmids (FIG. 15B) to calculate the probability of randomly finding a site that would have less than such 35% or 15% mismatch. Therefore, considering such degeneracy, the chances of finding a site unsuitable for cloning were $(1/4)^{9.75}$ and $(1/4)^{12.75}$ when using EarI and LguI, respectively. However, we encourage users to individually compare their flanking regions of internal 5'CTCTTC3' (5'GAAGAG3') sites with the TNT vector sequences shown in FIGS. 15A-15B.

Results

The Framework of TNT-Cloning System

Figure 1A:
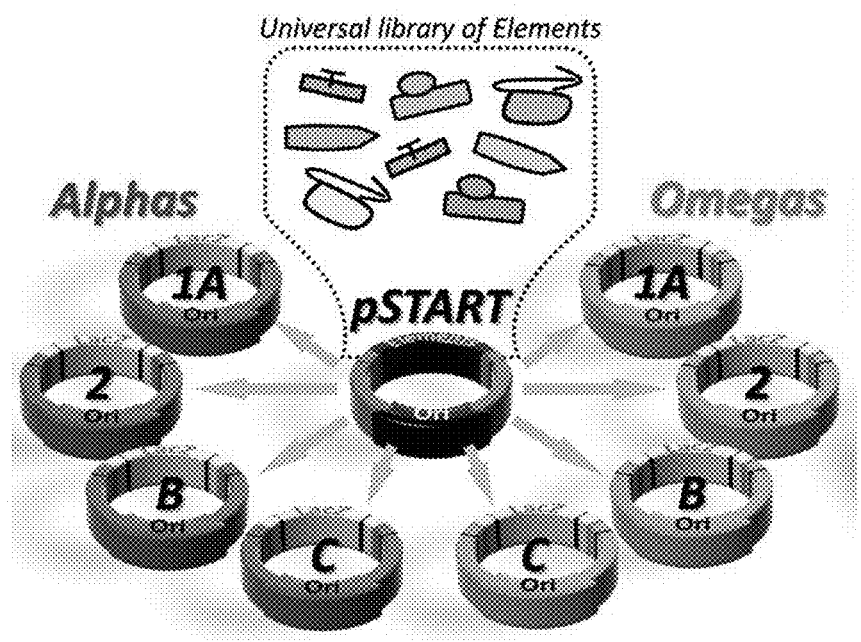
FIGS. 1A-1E. TNT-Cloning overview. (A) One universal library carrying the DNA fragments (elements; Synthetic Biology Open Language (SBOL) compliant) is built in the entry vector pSTART (which has a Carbenicillin resistance marker). Two different families of vectors, alpha (a; purple, Spectinomycin resistance marker) and omega (0; orange, Kanamycin resistance marker), comprised of 8 vectors each (1A, 2, B, C, 1A-R, 2-R, B-R and C-R, where "R" is the version for anti-sense insertion) can receive any element from the library at any time (arrows). Black lines in the vector backbone represent biding sites for type IIS enzymes that will cleave at the pink line. All vectors have the LacZw reporter for white/blue selection in *E. coli* T7Express. (B) Detailed enzyme binding site (black line) and cleavage site (pink) in the TNT vectors. Both enzymes, EarI (green) and LguI (red) will release the element from the library in the pSTART vector (top). However, enzyme sites are mirrored and flipped between α and Ω members (middle and bottom, respectively). This format support simultaneous digestion/ligation reactions (one-pot) and allow the assembly loop (see D for details). (C) Upon type IIS cleavage the desired fragments will be properly joined by different signatures (numbered 1 to 4) engineered to automatically keep both ORFs and the desired orientation of each fragment. Dotted lines point the ligation spot in leading strand of DNA. (D) Using versions 1A and 2 will join two fragments (binary assembly) and versions 1A, B and C will join three fragments (tertiary assembly; elements #1, #2 and #3). If α vectors are used as entry vectors, Ω vectors will be used as destination vectors and vice-versa. Each construct generated in a destination vector is ready to be used as entry vector in the next round of cloning. This set up creates an endless cloning loop (green arrows). Assemblies can also be done using pSTART as destination vector to build more library elements. (E) Transfer of 27 hypothetical elements from pSTART into either α or Ω family members using the "TNT-cloning loop". Elements are first transferred to a members (in this example) and combined, three at a time, to generate 9, 3 and finally 1 single insert after only 4 cloning steps.

To surpass one of the main limitations found on available cloning methodologies and to guarantee that our system will automatically join any element in a "coding sequence" (CDS) compatible manner, we choose the type IIS enzymes EarI and LguI that a) leave a tri-nucleotide (TNT) overhang and b) generate a particular overhang sequence downstream of their binding site. By using these enzymes, one truly "universal library" can be created in one entry vector (pSTART) that carries all the DNA segments to be joined in a pre-determined format by simply picking, matching and mixing them together. Therefore, regardless of the origin of the DNA sequence, multi-gene constructs can be created through sequential rounds of cloning requiring no adjustments to keep open reading frames (ORFs) functional (FIG. 1, FIG. 2). This strategy represents the first step toward several advantages found in the TNT-cloning system compared to previous methodologies. Virtually any regulatory regions (upstream regulatory region, URR; untranslated regions, UTRs; ribozymes; secondary regulatory sequences), CDSs (proteins; localization signals; affinity tags; functional domains), structural sequences (replication origins; repetitive DNA) or engineering scaffolds (interfering RNA, RNAi; artificial microRNA, amiR; guided RNA; recombination sites) can be introduced in the pSTART vector (FIG. 1A, FIG. 1B).

Figure 1B:
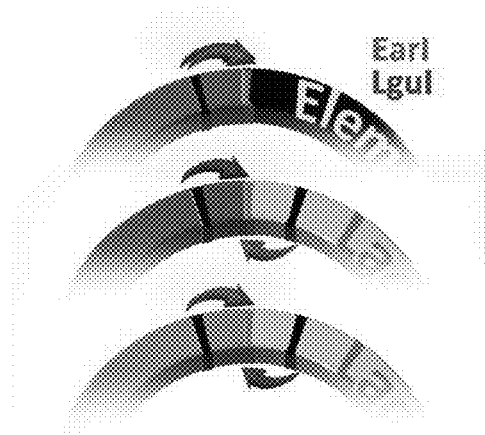
Figure 1C:
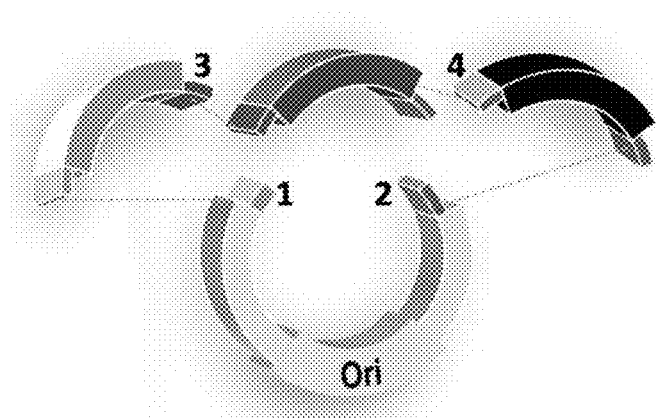
Figure 1D:
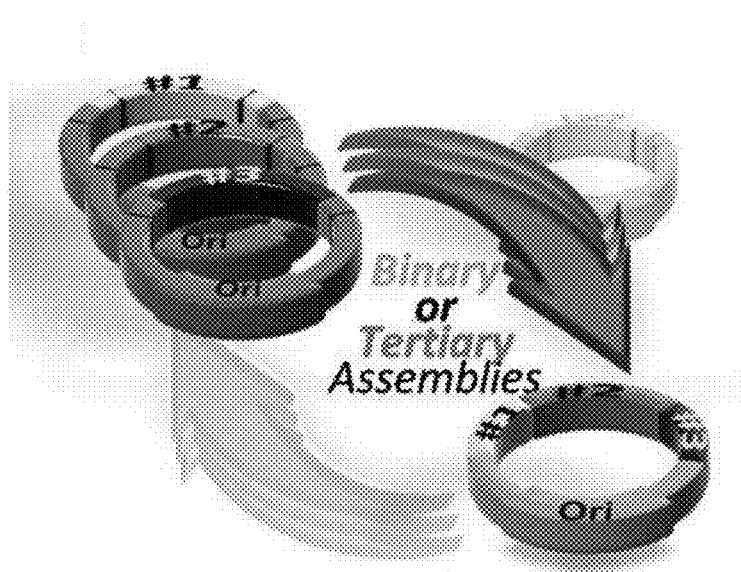
Figure 1E:
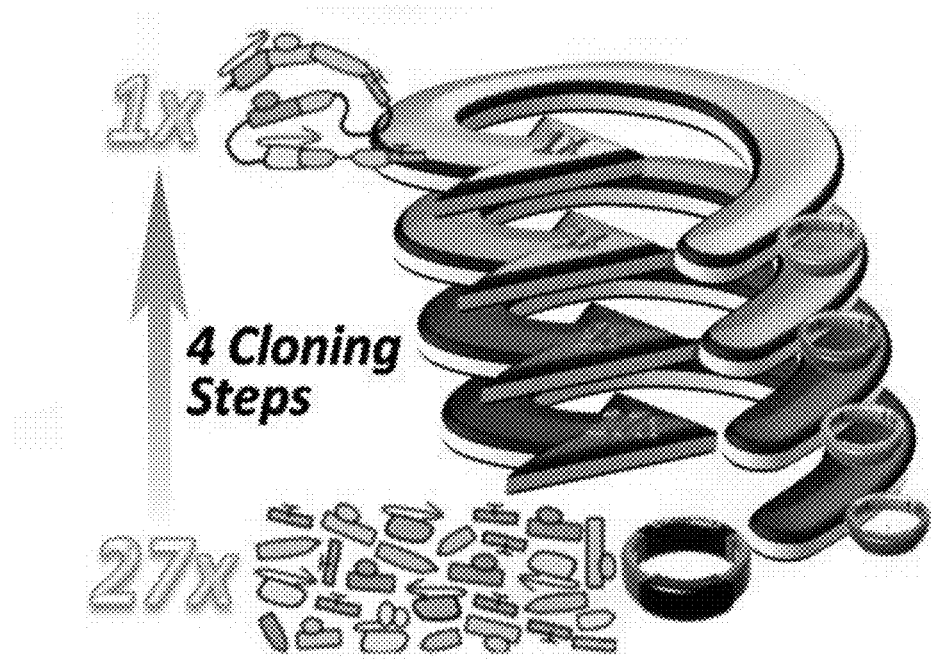

Once an element is cloned in pSTART, which receives and releases the desired fragments with either enzyme, it is transferred and further combined in either alpha (α) or omega (Ω) members, which receive fragments upon cleavage with EarI/LguI and release fragments upon cleavage with LguI/EarI, respectively (FIG. 1B). Upon digestion of each plasmid, a set of "signatures" that were specifically arranged to direct and orient the desired fragments are exposed (FIG. 1C). The signatures "1" and "2" are always flanking the inserts released from pSTART and are always used to join the final constructs into any α or Ω member. At the same time, the signatures "3" and "4" will be used by a specific member of each family (α and Ω) to join fragments between themselves, two fragments at once (binary assembly) using the members α1A and α2 (or Ω1A and Ω2) and three fragments at once (tertiary assembly) using the members α1A, αB and αC (or Ω1A, ΩB and ΩC) (FIG. 1D, FIG. 2A, FIGS. 4-7). To change the fragment orientation (sense or anti-sense) simply switch the chosen α or Ω version for its respective "R" version during the cloning step (FIG. 2A). The enzyme location and the signatures were designed to permit a pre-established cloning setup and to allow each final construct to be used as an insert in case a following round of cloning is needed, creating a cloning loop that can be repeated over and over to join multiple fragments into one larger construct (FIG. 1D, FIG. 1E). To exemplify, FIG. 1E shows how 27 hypothetical fragments from the universal library can be customized into one single insert through 4 cloning rounds. Importantly, the pSTART can also be used as destination vector to make the combined fragments an entry element in the library. The technical details for the library construction and the signatures/assembly setup are depicted in FIGS. 2A-2C and FIGS. 8-10.

Engineering Enzyme-Specific Sites

To date, all type IIS enzymes suitable for use in our TNT-cloning system recognize either 5'CTCT-TCN▼NNN▲3' (e.g., EarI) or 5'GCTCTTCN▼NNN▲3' (e.g., LguI) sequences (Roberts, R. J., et al., *Nucleic acids research* 43, D298-299 (2015)). The EarI recognition site is nested within the LguI site, leaving only one specific site capable of generating a 3 nt overhang upon restriction digestion. To overcome this limitation we assessed EarI sensitivity to different methyl groups added either within or nearby the 5'GCTCTTCN▼NNN▲3' sequence (EarI was chosen over Eam1104I due to previous reports on methylation sensitivity (Roberts, R. J., et al., *Nucleic acids research* 43, D298-299 (2015)). We used three methyltransferases (M), M.SacI, M.SssI (2 sites) and M.TaqI to methylate, respectively, the cytosines at the positions 2/1 (forward/reverse strand), 7/8 or −1/1 and the adenines at the positions 9/6 (FIG. 11A). For this purpose, we used a 6,435 bp plasmid (pET-28-M.SacI) and different 1055 bp PCR fragments carrying at least two sites for the restriction endonuclease where at least one site would not be subjected to methylation (except for M.SssI where both sites were addressed simultaneously). Sensitivity tests showed that M.SacI and M.TaqI inhibited the enzyme activity by 83.4% (SE±5.4) and 99.9% (SE±0.03), respectively (FIG. 11B, FIG. 11C). M.SssI generated two distinct methylation sites and had little (M.SssI-1) or no (M.SssI-2) effect in EarI ability to cut the modified DNA (FIG. 11B, FIG. 11C).

Because M.TaqI was highly capable of inhibiting the EarI activity, we adopted this modification in the TNT-cloning system, with the first nucleotide of each signature that flanks the restriction site starting with an adenine (Supplementary FIG. 1). We engineered the genome of the *E. coli* strain T7Express (T7X) to be capable of expressing the M.TaqI gene during its regular life cycle. Different conditions for growing the engineered strain (T7X.MT), while keeping maximum DNA methylation, were tested and the optimal practice is shown in FIG. 11D, where 97.1% (SE±0.8) of the plasmid DNA extracted from T7X.MT was unable to be cut by EarI. Our results show the use of this strain is comparable to the modification levels obtained for the in vitro methylation. Methylated DNA extracted from T7X.MT remains stable at −15° C. for at least 11 weeks without compromising EarI/Eam1104I inhibition. There is no methylation requirement for both the Ω members and downstream cloning steps in the α members, and therefore, any construct generated using the TNT-cloning system can be transformed in the strain of choice (T7Express can be used to allow for white/blue screening). As a consequence, it is not necessary to define LguI sensitivity to methylation; however, we report a sensitivity chart for three isoschizomers in this class: BspQI, LguI and SapI. Importantly, LguI is also sensitive to M.TaqI modification, yet this is irrelevant because M.TaqI site is not present at a critical position on Ω members and transformation of constructs carrying the joined fragment(s) in the α members is not required for T7X.MT. Consequently, the T7X.MT strain is useful for propagation of the original TNT-plasmids but problematic for downstream cloning purposes. Our results show that we successfully engineered two distinct sites to support the assembling loop presented, with LguI recognizing and cleaving at the sequence 5'GCTCT-TCN▼NNN▲3' and EarI recognizing and cleaving at the sequence 5'CTCTTCN▼NNN▲3' (but not at the sequence 5'GCTCTT*CN▼N*NN▲3', where T*/N* represent a methylation of the corresponding adenines). By using the engineered *E. coli* strain our required modification is simple to implement.

Validation of TNT-Cloning System

Once we defined the specificity of the restriction sites, we built all 17 TNT-vectors described in FIG. 1; pSTART (carbenicillin resistance), α members (α1A, α2, αB, αC, α1A-R, α2-R, αB-R, αC-R; spectinomycin resistance) and Ω members (Ω1A, Ω2, ΩB, ΩC, Ω1A-R, Ω2-R, ΩB-R, ΩC-R; kanamycin resistance—see Methods for details)

based on the use of M.TaqI. Several fragments were amplified by PCR or synthesized to be cloned into pSTART and became an "element" in our universal library. These fragments are listed in Table I. Importantly, we subjected some of our CDS to the domestication process, i.e., to screen and synonymously mutate 5'CTCTTC3' and 5'GAAGAG3' sites in order to avoid internal fragment cleavage during the cloning steps. However, to domesticate a fragment is not mandatory for our system.

To maintain maximum flexibility, the CDS have no 'stop codons', which are included in the Terminators/3'UTRs. As a proof-of-concept we used ten different DNA fragments from our library to design four final constructs expressing a set of two reporters, red (mCherry) and green fluorescent proteins (GFP), fused to PIP2 (plasma membrane intrinsic protein, Boavida, L. C., et al., *Plant physiology* 163, 696-712 (2013)) and the known subcellular domains NLS (nuclear localization signal: PKKKRKVEDP; Slootweg, E. et al. *The Plant cell* 22, 4195-4215 (2010)), with or without a "self-splicing" protein (SS) in between each reporter gene (Donnelly, M. L. et al., *The Journal of general virology* 82, 1013-1025 (2001), Francois, I. E. et al., *Plant physiology* 128, 1346-1358 (2002)) (FIG. 12A). Each construct, 35S:: NLS-GFP-NLS-Term (a/A) (GFP control), 35S::tag-PmCherry-Term (Ω1A) (PmCherry control), 35S::tag-PmCherry-NLS-GFP-NLS-tag-Term(Ω1A) (Fused control) and different 35S::tag-PmCherry-SS1-SS2-NLS-GFP-NLS-tag-Term were transformed in agrobacteria and infiltrated in tobacco leaves to confirm mCherry and GFP fluorescence (FIGS. 12B-12C). The combinations of SS1-SS2 were P2AF2A (ΩB), P2AT2A (Ω1A) or IbpF2A (ΩC) (different peptide 2A, Donnelly, M. L. et al., *The Journal of general virology* 82, 1013-1025 (2001); *Impatiens balsamina* peptide, cleaved in plants, Francois, I. E. et al., *Plant physiology* 128, 1346-1358 (2002)).

As expected, the Fused control had the same expression pattern as 35S::NLS-GFP-NLS-Term (α1A) and were nuclear localized (FIG. 3B). The constructs carrying the SS clusters should mimic the clean separation of signals observed when GFP control and PmCherry control are co-infiltrated (FIG. 12B; non-Fused control) indicating an effective split between both reporters. The most efficient split was observed when either P2AF2A (99.7% SE±1.2) or P2AT2A (94.2% SE±2.8) were used and less definitive cellular split efficiencies were observed when IbpF2A (79.7% SE±8.5) was used (FIGS. 12B-12C). These results demonstrate multiple coding sequences can be coupled into one mRNA to efficiently undergo independent translation, and indicate that this approach is an extremely useful strategy to overcome promoter shortage.

To evaluate the effect of fragment length on the efficacy and efficiency of our system we used the Fused control (≈4 kb), the P2AF2A cluster (≈4 kb) and the IbpF2A cluster (≈4 kb) in Ω1A, ΩB and ΩC, and used a tertiary assembly to generate a ≈12 kb fragment in α1A (FIG. 3D). Additionally, we developed an efficient protocol along with an improved buffer system (called TNT-Buffer) that allowed EarI and/or LguI enzymes to work well in combination with T4 DNA ligase in a "one-pot-reaction" (FIG. 12E). When a single insert is being transferred from the pSTART to α or Ω members, the number of positive clones generated when using the TNT-buffer were 2-5 fold higher than using the original T4 DNA ligase buffer under the same conditions (FIG. 12E, FIG. 14A). Similar constructs were tested using other cloning strategies following the manufacturer protocol and scored less efficient as our TNT-buffer (FIG. 12E).

The key component of our buffer is a branched polyethylene glycol that appears to allow efficient digestion/ligation while maintaining efficient exchange of inserts between vectors (see conflict of interest). Since the isothermal (Gibson) assembly also allows for multiple fragments cloning, we compared one, two and three inserts plus the vector using both methodologies—the 1 h Gibson assembling reaction (at 50° C.) or the one-pot-reaction in TNT-buffer (50 cycles of 34° C. for 45 sec and 16° C. for 4.5 min) (FIG. 12E). Both methods performed well, however, the isothermal assembly requires sequence homology, making repetitive sequences a hurdle and compromising flexibility for multiple combinations or shuffling of fragments. Importantly, the TNT-buffer was at least 12 times more capable of performing tertiary assemblies than the T4 DNA ligase buffer (FIG. 13B). Interestingly, regardless the buffer system, the LguI enzyme showed some promiscuity over the 5'aaCTCTTC3' EarI site originally included in the Ω vectors and four point mutations upstream of the biding site (from aa into tt, gt and cc) were tested and changed in order to improve the efficiency of the Ω members when used as destination vectors (FIG. 13B).

Our results show that the TNT-cloning system is a powerful tool for flexible, rapid and all-in-one assembling of various DNA fragments requiring no homology or linker/adaptors between fragments. The ≈12-kb proof-of-principle fragment noted above is an example of how 28 fragments from the library could be easily designed and joined into a single insert using 5 cloning steps. Because each construct generated is ready to be used as an entry clone for future assembling (and as an element in the library if cloned in the pSTART), our system is also versatile and convenient, requiring minimal to no re-cloning.

Overcoming the Domestication Step

One major limitation of cloning methods that rely on restriction nucleases is the fact that the restriction sites should be unique, to avoid cleavage within the fragment of interest. One solution already mentioned above is to domesticate a fragment by changing a 5'CTCTTC3' site(s) while maintaining its functionality. However, many fragments cloned are not CDS and therefore this strategy cannot be applied. Although the TNT-Buffer successfully joined non-domesticated fragments (with internal 5'CTCTTC3' sites) (FIG. 4A), tertiary assembling involving non-domesticated inserts were complex and positive clones from a regular TNT-reaction were rare (data not shown). Therefore, we utilized the ability of DNA to form triplexes between a double strand fragment and a oligonucleotide (Praseuth, D., et al., *Biochimica et biophysica acta* 1489, 181-206 (1999), Nikolova, E. N., et al., *Journal of the American Chemical Society* 135, 6766-6769 (2013), Brunet, E. et al., *Nucleic acids research* 33, 4223-4234 (2005)) in an effort to change the DNA-enzyme interactivity (Ward, B., *Nucleic acids research* 24, 2435-2440 (1996)) and inhibit the digestion progress by masking specific 5'GCTCTTC3' sites, while leaving the remaining (vectorial) 5'GCTCTTC3' sites available for the LguI/EarI to recognize and digest.

Figures 15A, 15B:
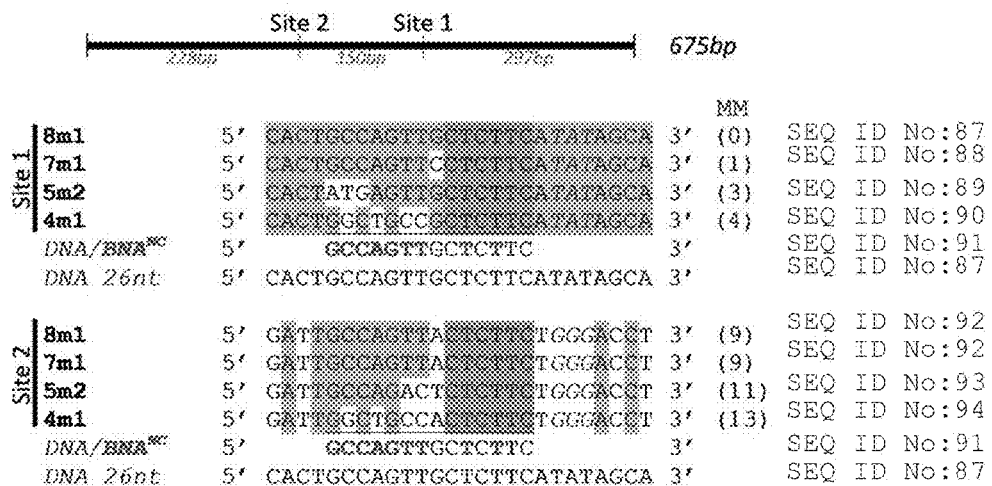
FIGS. 15A-15E. Oligo-dependent inhibition of digestion at 5'GCTCTTC3' and 5'CTCTTC3' sites. (A) DNA templates studied with nomenclature, sequence and number of mismatches (MM) related to the 14 nt DNA/BNA$^{NC}$ (purple) and 26-nt DNA oligonucleotides. PCR product (675 bp) was used here. Restriction sites for LguI and EarI as well as the distance between them are indicated at sites 1 and 2. 5'CTCTTC3' sequence and matches to the oligo are indicated in green and blue, respectively. (B) TNT-plasmids showing the 5'CTCTTC3' flanking sequences aligned to the 26-nt DNA oligo. All the α and Ω members (except Ω1A) share the same sequence within each family at the left (L) or at the right (R) side of the LacZω reporter, respectively. Number of mismatches is also indicated. V=A, C or G, M=A or C, Y=C or T, N=any. (C) Oligo-dependent inhibition of digestion at site 1 using the templates 8m1 (200 ng) and 5m2 (200 ng) during increasing amounts of 14-nt DNA/BNA$^{NC}$ linked to acridine (Acr-DNA/BNA$^{NC}$). Oligos were incubated for 6 h at 37° C. in Tris-Acetate buffer (50 mM pH 7.0, 20 mM NaCl, 10 mM MgCl$_2$) in 5 μl before being subjected to digestion (1 U LguI, 25 min at 34° C.) in 10 μl final volume. Reaction was stopped and gel bands quantified and plotted as percentage of the control without oligo (N.O.). Digestion progress is the ratio of digested/(digested+nondigested) bands in each tube. Values when present are expressed as percentage of N.O. tube. Digestion progress in these panels was 19.7% (SE±2.2). Oligo amount is indicated. (D) Digestion progression curve in the absence (N.O.) or presence of the 26-nt DNA oligo (50 μM) in two different templates: 8m1 (0 mismatch, 180 ng) and 4m1 (4 mismatches, 180 ng). Oligo and templates were incubated for 45° C.-12° C. (every 3° C., 1 h each) in 4 μl Tris-HCl buffer (50 mM pH 5.8, 75 mM NaCl, 10 mM MgCl$_2$, 2 mM DTT) before being subjected to digestion (1.5 U LguI, 2-30 min at 25° C.) in 10 μl final volume (completed with Tris-HCl 50 mM pH 6.3, 10 mM MgCl$_2$, 2 mM DTT); 5, 10 and 15 min in these conditions corresponds to 24.4% (SE±0.6), 40.3% (SE±0.6) and 62.0% (SE±2.1) digestion progression, respectively. Digestion is fairly linear in the N.O. tube in the range of 2 min (14.8% SE±0.6) to 20 min (76.6% SE±1.6) ($R^2$=0.9967), gray background. (E) Oligo-dependent inhibition of digestion at sites 1 (LguI and EarI) and 2 (EarI only)
Figure 15C:
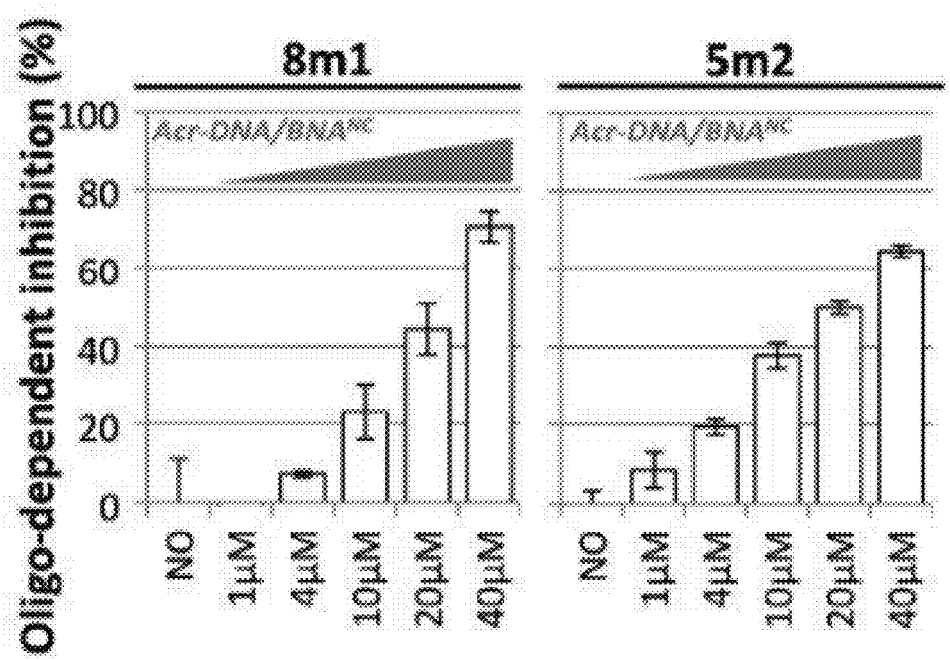
Figure 15D:
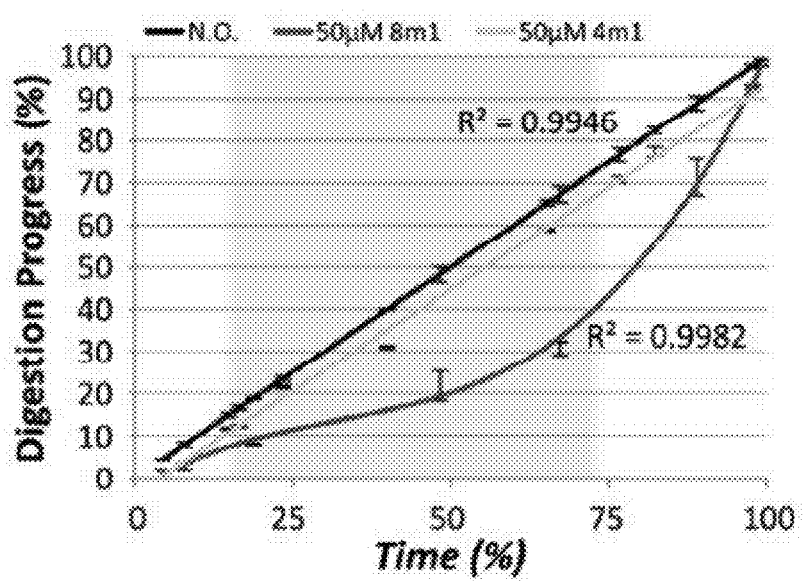
Figure 15E:
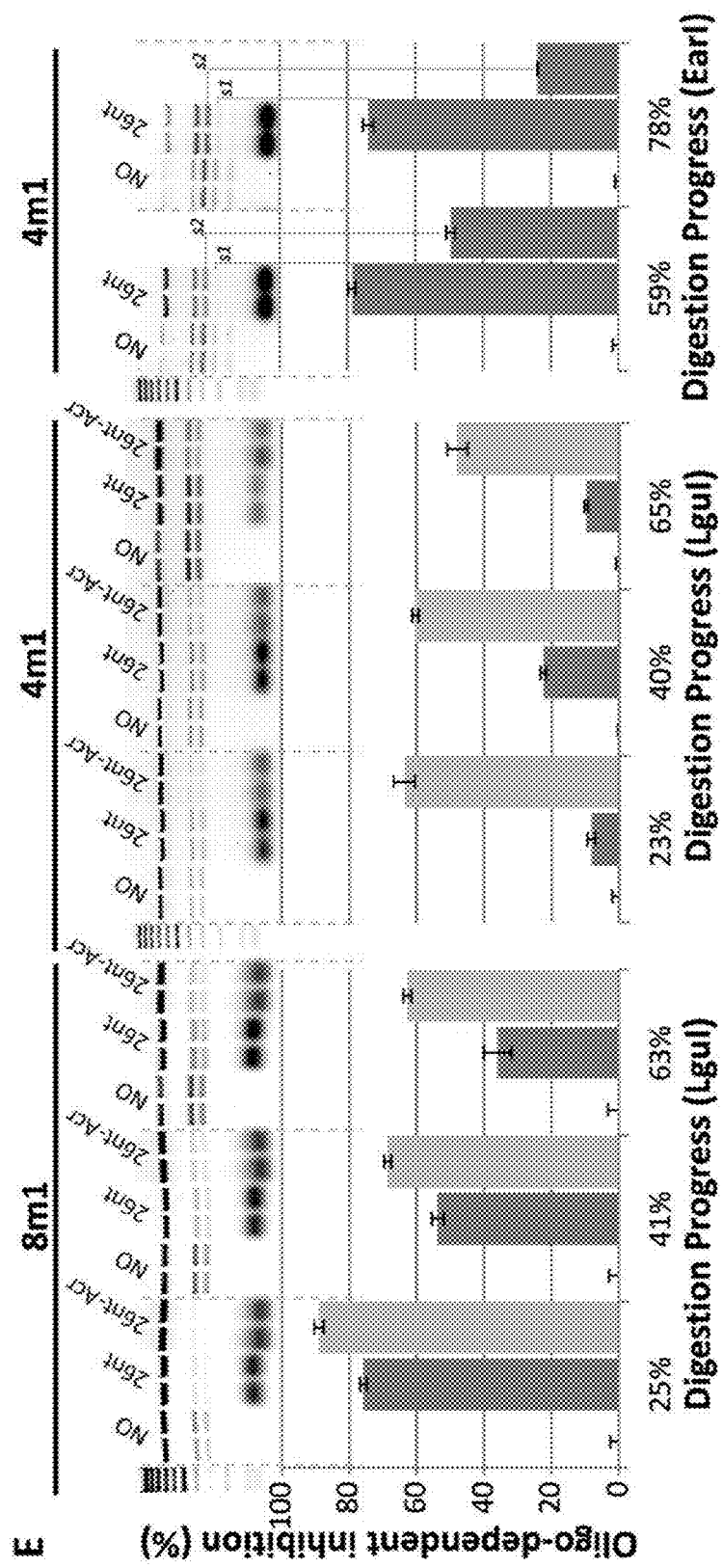

To design such oligos, we adopted the Reverse-Hoogsteen orientation (Praseuth, D., Guieysse, A. L. et al., *Biochimica et biophysica acta* 1489, 181-206 (1999)), which allows for all four nucleotides to be part of the triple helix. Initially, we combined the ability of the intercalating dye acridine (Acr) to stabilize triple helixes with the modified oligonucleotide DNA/BNA$^{NC}$ (2'-O,4'-C-aminomethylene bridged nucleic acid), which has stronger binding affinity than DNA oligos (14 bp DNA/BNA$^{NC}$ Tm=82.5° C.) and is more capable of forming triplexes at physiological pH (7.0-8.3) (Brunet, E. et al., *Nucleic acids research* 33, 4223-4234 (2005)). Increasing amounts of DNA/BNA$^{NC}$ oligo showed oligo-dependent inhibition of the digestion progress over the 675 bp PCR product template '8m1', suggesting inhibition of enzyme activity by a potential triplex formation (FIGS. 15C-15D). On the other hand, the DNA/BNA$^{NC}$ was not able to discriminate 5'mismatches (3 in total) as observed in template '5m2', showing this oligo does not differentiate small mismatch changes as those found between internal and vectorial 5'GCTCTTC3' sites.

Therefore, we decided to test two regular DNA oligonucleotides (26 nt and 26 nt-Acr) covering 11 nt upstream and 8 nt downstream of the 5'GCTCTTC3' site. A "digestion-progression curve" using LguI on the non-domesticated templates 8m1 (0 mismatches) and '4m1' (4 mismatches) in the absence or presence of 50 µM of the 26-nt DNA oligo were performed to understand the kinetics involved in the digestion inhibition (FIG. 14B, FIG. 15D). After 24.4% (SE±0.6) of digestion progress, the 26-nt DNA oligo inhibited the LguI cleavage in the 8m1 template by 75.9% (SE±0.9) and only 8.3% (SE±1.6) in the 4m1 template, indicating the strategy was efficient and specific (FIG. 4B). Interestingly, after 77.9% (SE±0.3) digestion, inhibition of templates in EarI-based reactions was still evident at 73.8% (SE±1.5) when 4 mismatches were present, but 23.9% (SE±0.2) when 13 mismatches were present, which slightly compromised specificity for EarI-based reactions (FIGS. 15C-15D). Expectedly, the 26-nt-Acr oligo showed stronger inhibition but intensely compromised specificity (FIG. 14C). These screening results show the 26-nt oligo created a manageable "blind-spot" for both LguI and EarI enzymes which prevents recognition of specific DNA sites.

We validated this strategy by performing single cloning from pSTART to Ωs (by LguI) and tertiary assembly from Ωs to αs (by EarI) using non-domesticated fragments (FIG. 4D). Compared to the 7m1 domesticated (Dom) fragment, the 8m1 (NoDom) non-domesticated fragment drastically reduce the number of positive clones, which was raised to 74.0% (SE±2) of the 7m1 level when the 26-nt oligo is incubated with the template plasmid (FIG. 4E). When a tertiary assembly is performed using two among three fragments with a total of four 5'CTCTTC3' sites (template 8m1), the previous incubation with the oligo somehow keeps the number of positive clones but raises the cloning accuracy from 31.2% (SE±4.4) to 77.1% (SE±1.4) (FIG. 14E). Combined, these results show the oligo incubation protects chosen 5'GCTCTTC3' sites during one and multiple fragments cloning while allowing LguI/EarI to reliably digest the sites that flank the insert in pSTART, α and Ω members (FIG. 15B). Thus, rather than screening for a 6 nt sequence (5'CTCTTC3' or 5'GAAGAG3', frequency ≈1 per 2048 bp) within the fragment of interest, a new sequence is used (frequency ≈1 per 7.4×10$^5$ by when assembly uses EarI and ≈1 per 4.7×10$^7$ by when assembly uses LguI) and the chances of requiring a fragment mutation is greatly reduced.

Discussion

Placing methyl groups in the type IIS enzymes binding site generated two recognition sites for two distinct enzymes that creates an innovative and flexible cloning platform, allowing for multiple fragments (up to 3 at once) to be combined from a single universal library in a one-pot reaction with high efficiency and high fidelity. The ability to keep ORFs in frame by using cloning signatures that bear three nucleotide tag allowed us to include all cloning fragments, as CDS pieces, into a single universal library and, therefore, simplify assembling by orderly 'picking and mixing' the fragments of interest. In this approach inversions were, and can be, easily performed by merely swapping the destination vector with its corresponding "R" version. Similarly, relocation of fragments was easily performed by rearranging intermediate cloning products rather than starting from the beginning of the process.

Such advantages are key for establishing a easily transferable platform for quick determination of qualitative and quantitative gene fragment interactions that will have to be performed in studies involving gene sets and gene networks. Currently, the validation of such networks and the reproducibility of data are limited by the inability of building various compatible multigene constructs from one flexible universal platform. The optimized TNT-cloning system and buffer, overcome these limitations by allowing several fragments from the universal library to be orderly combined into 1 insert after a minimal number of cloning steps in a matter of days.

Within the context of synthetic biology, an important aspect for studies in regulatory networks and pathway engineering is the need of numerous regulatory sequences that may be incompatible with current cloning systems and/or limited in numbers of assembled genes for multigene studies. Here, we were able to provide a protocol that is greatly capable of cloning fragments bearing internal 5'GCTCTTC3' sites. This approach is affordable and straightforward allowing for efficient cloning and assembling of fragments inapt for mutagenesis. Also, to extend the use of one regulatory sequence to multiple CDS, we clustered different peptide 2As to overcome flaws found when only one sequence is used (Donnelly, M. L. et al., *The Journal of general virology* 82, 1013-1025 (2001)) by assuming a simple probability test should be applicable (if one copy gives 20% flaw, for example, two copies should reduce such number to 4%, etc.). We showed that clustering of numerous gene fragments corroborates our predictions, as P2AT2A and P2AF2A constructs gave almost flawless split between two CDS while their sole use show imperfect split in several cellular backgrounds (Kim, J. H. et al., *PLoS One* 6, e18556 (2011)). The clustered P2A efficiency provide a similar output for polycistronic mRNA as if individual mRNAs were expressed in planta (FIG. 12B) and demonstrates the power of a methodology that allows an endless assembly with CDS compatibility.

TABLE I

| (Sequences In FIGS. And Detailed Description) | | |
|---|---|---|
| SEQUENCE | SEQ ID NO: | LOCATION OF SEQUENCE |
| ACATGCAGCTCTTCC | SEQ ID NO: 1 | FIG. 2A |
| GGAAGAGCTGCATGT | SEQ ID NO: 2 | FIG. 2A |
| GGAAGAGCTTCCTCG | SEQ ID NO: 3 | FIG. 2A |
| CGAGGAAGCTCTTCC | SEQ ID NO: 4 | FIG. 2A |

TABLE I-continued (Sequences In FIGS. And Detailed Description)

Figure 4:
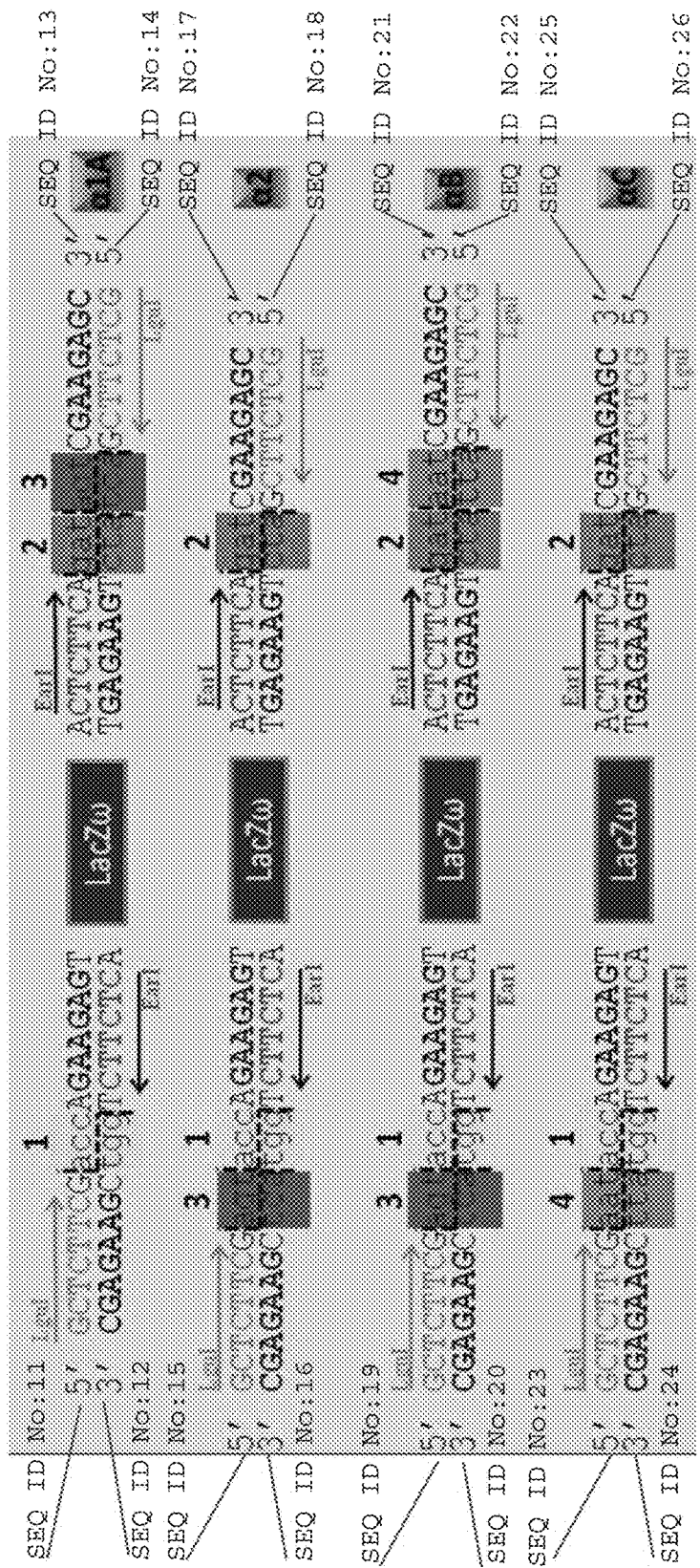
FIG. 4. Details of cloning site sequences of alpha (α) family of vectors (α1A, α2, αB, αC). All α vectors, purple font is *Enterobacter aerogenes* I (EarI) restriction enzyme binding site; orange font is *Lysobacter gummosus* RFLI (LguI) binding site; yellow highlight indicates signature element 1 (forward strand, acc; reverse strand, tgg); green highlight indicates signature element 2 (forward strand, gat; reverse strand, cta); red highlight indicates signature element 3 (forward strand, agt; reverse strand, tca); blue highlight indicates signature element 4 (forward strand, aat; reverse strand, tta); dotted lines indicate location of cleavage by restriction enzyme. (α1A) The α1A vector has a selectable marker (here, LacZω), type IIS restriction enzyme sites, and signature elements 1, 2, and 3. The forward strand upstream of the marker gene has an LguI restriction enzyme binding site, such that LguI enzyme cleaves across signature element 1, leaving a tgg cohesive end signature on the reverse strand (vector) and an acc cohesive end signature on the forward strand (insert). Downstream of the marker gene, the forward strand has an EarI restriction enzyme binding site, such that EarI enzyme cleaves across signature element 2, leaving a gat cohesive end signature on the forward strand (vector) and a cta cohesive end signature on the reverse strand (insert). The reverse strand of α1A has, from 3' to 5': signature element 1; an EarI binding site, such that EarI enzyme cleaves across signature element 1, leaving a tgg cohesive end signature on the reverse strand (vector) and an acc cohesive end signature on the forward strand (insert); the selectable marker; signature elements 2 and 3 which are adjacent to each other; and an LguI binding site, such that LguI enzyme cleaves across the 3' end of signature element 3, leaving a 5' agt cohesive end signature on the forward strand (vector) and an tca signature on the reverse strand (insert). (α2) The α2 vector has adjacent signature elements 3 and 1 upstream of the marker gene, and signature element 2 downstream of the marker; an LguI restriction enzyme site on the forward strand that leaves tgg/acc cohesive ends across signature element 3; an EarI restriction enzyme site on the reverse strand that leaves acc/tgg cohesive ends across signature element 1; and an EarI restriction enzyme site on the forward strand and an LguI restriction enzyme site on the reverse strand that each leave gat/cta cohesive ends across signature element 2. (αB) The αB vector has adjacent signature elements 3 and 1 upstream of the marker gene, and adjacent signature elements 2 and 4 downstream of the marker; an LguI restriction enzyme site on the forward strand that leaves tgg/acc cohesive ends across signature element 3; an EarI restriction enzyme site on the reverse strand that leaves acc/tgg cohesive ends across signature element 1; an EarI restriction enzyme site on the forward strand that generates gat/cta cohesive ends across signature element 2; and an LguI restriction enzyme site on the reverse strand that generates aat/tta cohesive ends across signature element 4. (αC) The αC vector has adjacent signature elements 4 and 1 upstream of the marker gene, and signature element 2 downstream of the marker; an LguI restriction enzyme site on the forward strand that generates aat/tta cohesive ends across signature element 4; an EarI restriction enzyme site on the reverse strand that leaves acc/tgg cohesive ends across signature element 1; and an EarI restriction enzyme site on the forward strand and an LguI restriction enzyme site on the reverse strand that each leave gat/cta cohesive ends across signature element 2.
Figure 5:
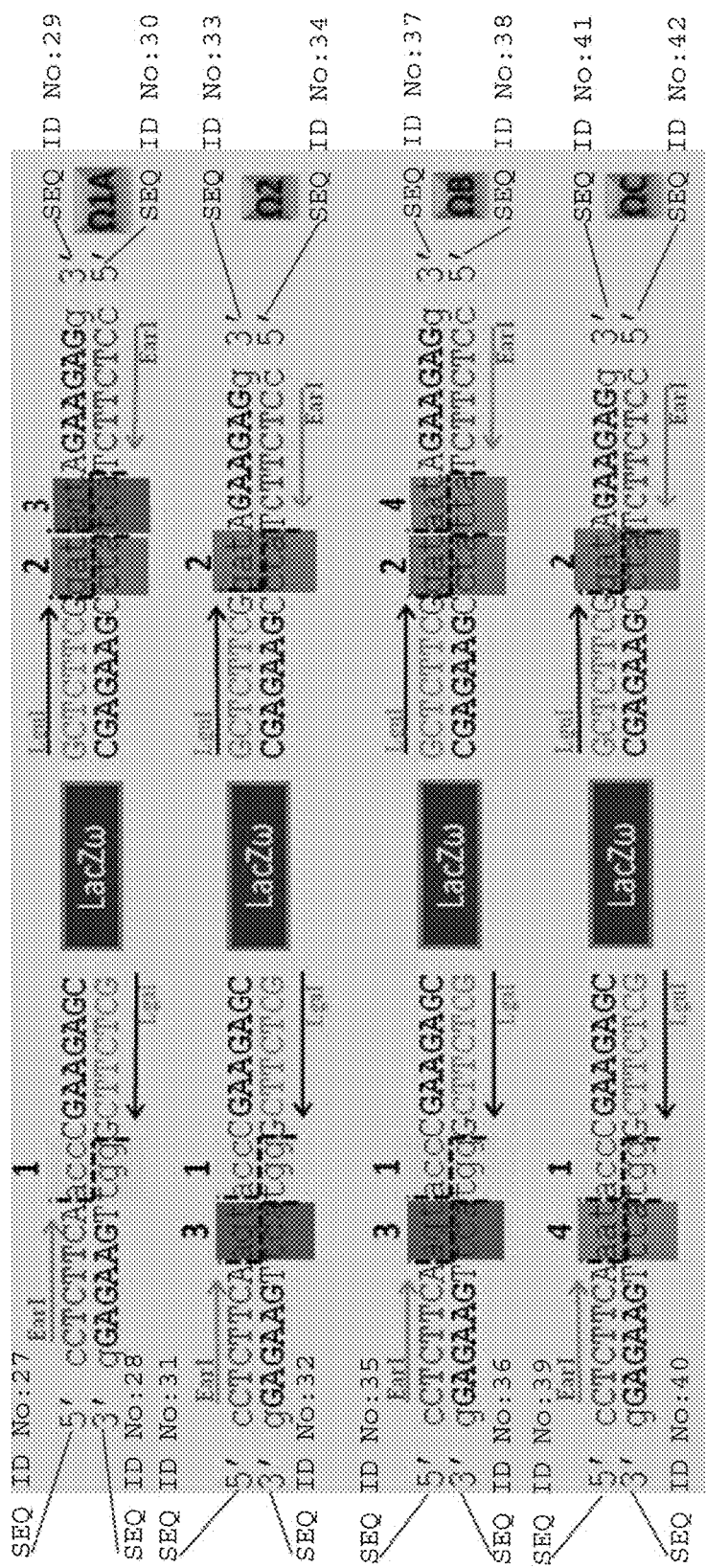
FIG. 5. Details of cloning site sequences of omega (Ω) family of vectors (Ω1A, Ω2, ΩB, ΩC). All Ω vectors, purple font is EarI restriction enzyme binding site; orange font is LguI binding site; yellow highlight indicates signature element 1 (forward strand, acc; reverse strand, tgg); green highlight indicates signature element 2 (forward strand, gat; reverse strand, cta); red highlight indicates signature element 3 (forward strand, agt; reverse strand, tca); blue highlight indicates signature element 4 (forward strand, aat; reverse strand, tta); dotted lines indicate location of cleavage by restriction enzyme. (Ω1A) The Ω1A vector has a selectable marker (here, LacZω), type IIS restriction enzyme sites, and signature elements 1, 2, and 3. The forward strand upstream of the marker gene has an EarI restriction enzyme binding site, such that EarI enzyme cleaves across signature element 1, leaving a tgg cohesive end signature on the reverse strand (vector) and an acc cohesive end signature on the forward strand (insert). Downstream of the marker gene, the forward strand has an LguI restriction enzyme binding site, such that LguI enzyme cleaves across signature element 2, leaving a gat cohesive end signature on the forward strand (vector) and a cta cohesive end signature on the reverse strand (insert). The reverse strand of Ω1A has, from 3' to 5': signature element 1; an LguI binding site, such that LguI enzyme cleaves across signature element 1, leaving a tgg cohesive end signature on the reverse strand (vector) and an acc cohesive end signature on the forward strand (insert); the selectable marker; signature elements 2 and 3 which are adjacent to each other; and an EarI binding site, such that EarI enzyme cleaves across the 3' end of signature element 3, leaving a 5' agt cohesive end signature on the forward strand (vector) and an tca signature on the reverse strand (insert). (Ω2) The Ω2 vector has adjacent signature elements 3 and 1 upstream of the marker gene, and signature element 2 downstream of the marker; an EarI restriction enzyme site on the forward strand that leaves tgg/acc cohesive ends across signature element 3; an LguI restriction enzyme site on the reverse strand that leaves acc/tgg cohesive ends across signature element 1; and an LguI restriction enzyme site on the forward strand and an EarI restriction enzyme site on the reverse strand that each leave gat/cta cohesive ends across signature element 2. (ΩB) The ΩB vector has adjacent signature elements 3 and 1 upstream of the marker gene, and adjacent signature elements 2 and 4 downstream of the marker; an EarI restriction enzyme site on the forward strand that leaves tgg/acc cohesive ends across signature element 3; an LguI restriction enzyme site on the reverse strand that leaves acc/tgg cohesive ends across signature element 1; an LguI restriction enzyme site on the forward strand that generates gat/cta cohesive ends across signature element 2; and an EarI restriction enzyme site on the reverse strand that generates aat/tta cohesive ends across signature element 4. (ΩC) The ΩC vector has adjacent signature elements 4 and 1 upstream of the marker gene, and signature element 2 downstream of the marker; an EarI restriction enzyme site on the forward strand that generates aat/tta cohesive ends across signature element 4; an LguI restriction enzyme site on the reverse strand that leaves acc/tgg cohesive ends across signature element 1; and an LguI restriction enzyme site on the forward strand and an EarI restriction enzyme site on the reverse strand that each leave gat/cta cohesive ends across signature element 2.

| SEQUENCE | SEQ ID NO: | LOCATION OF SEQUENCE |
| --- | --- | --- |
| CAGGCTCTTCGACCAGAAGAGTGG | SEQ ID NO: 5 | FIG. 2A |
| TATGCTCTTCGGATAGTAGAAGAGGGG | SEQ ID NO: 6 | FIG. 2A |
| GCTCTTCCACCCCGGG | SEQ ID NO: 7 | FIG. 3 |
| CCCGGGGTGGAAGAGC | SEQ ID NO: 8 | FIG. 3 |
| CCCGGGATGGAAGAGC | SEQ ID NO: 9 | FIG. 3 |
| GCTCTTCCATCCCGGG | SEQ ID NO: 10 | FIG. 3 |
| GCTCTTCGACCAGAAGAGT | SEQ ID NO: 11 | FIG. 4 |
| ACTCTTCTGGTCGAAGAGC | SEQ ID NO: 12 | FIG. 4 |
| ACTCTTCAGATAGTCGAAGAGC | SEQ ID NO: 13 | FIG. 4 |
| GCTCTTCGACTATCTGAAGAGT | SEQ ID NO: 14 | FIG. 4 |
| GCTCTTCGAGTACCAGAAGAGT | SEQ ID NO: 15 | FIG. 4 |
| ACTCTTCTGGTACTCGAAGAGC | SEQ ID NO: 16 | FIG. 4 |
| ACTCTTCAGATCGAAGAGC | SEQ ID NO: 17 | FIG. 4 |
| GCTCTTCGATCTGAAGAGT | SEQ ID NO: 18 | FIG. 4 |
| GCTCTTCGAGTACCAGAAGAGT | SEQ ID NO: 19 | FIG. 4 |
| ACTCTTCTGGTACTCGAAGAGC | SEQ ID NO: 20 | FIG. 4 |
| ACTCTTCAGATAATCGAAGAGC | SEQ ID NO: 21 | FIG. 4 |
| GCTCTTCGATTATCTGAAGAGT | SEQ ID NO: 22 | FIG. 4 |
| GCTCTTCGAATACCAGAAGAGT | SEQ ID NO: 23 | FIG. 4 |
| ACTCTTCTGGTATTCGAAGAGC | SEQ ID NO: 24 | FIG. 4 |
| ACTCTTCAGATCGAAGAGC | SEQ ID NO: 25 | FIG. 4 |
| GCTCTTCGATCTGAAGAGT | SEQ ID NO: 26 | FIG. 4 |
| CCTCTTCAACCCGAAGAGC | SEQ ID NO: 27 | FIG. 5 |
| GCTCTTCGGGTTGAAGAGG | SEQ ID NO: 28 | FIG. 5 |
| GCTCTTCGGATAGTAGAAGAGG | SEQ ID NO: 29 | FIG. 5 |
| CCTCTTCTACTACTCCGAAGAGC | SEQ ID NO: 30 | FIG. 5 |
| CCTCTTCAAGTACCCGAAGAGC | SEQ ID NO: 31 | FIG. 5 |
| GCTCTTCGGGTACTTGAAGAGG | SEQ ID NO: 32 | FIG. 5 |
| GCTCTTCGGATAGAAGAGG | SEQ ID NO: 33 | FIG. 5 |
| CCTCTTCTATCCGAAGAGC | SEQ ID NO: 34 | FIG. 5 |
| CCTCTTCAAGTACCCGAAGAGC | SEQ ID NO: 35 | FIG. 5 |
| GCTCTTCGGGTACTTGAAGAGG | SEQ ID NO: 36 | FIG. 5 |
| GCTCTTCGGATAATAGAAGAGG | SEQ ID NO: 37 | FIG. 5 |
| CCTCTTCTATTATCCGAAGAGC | SEQ ID NO: 38 | FIG. 5 |
| CCTCTTCAAATACCCGAAGAGC | SEQ ID NO: 39 | FIG. 5 |
| GCTCTTCGGGTATTTGAAGAGG | SEQ ID NO: 40 | FIG. 5 |
| GCTCTTCGGATAGAAGAGG | SEQ ID NO: 41 | FIG. 5 |
| CCTCTTCTATCCGAAGAGC | SEQ ID NO: 42 | FIG. 5 |

TABLE I-continued (Sequences In FIGS. And Detailed Description)

Figure 6:
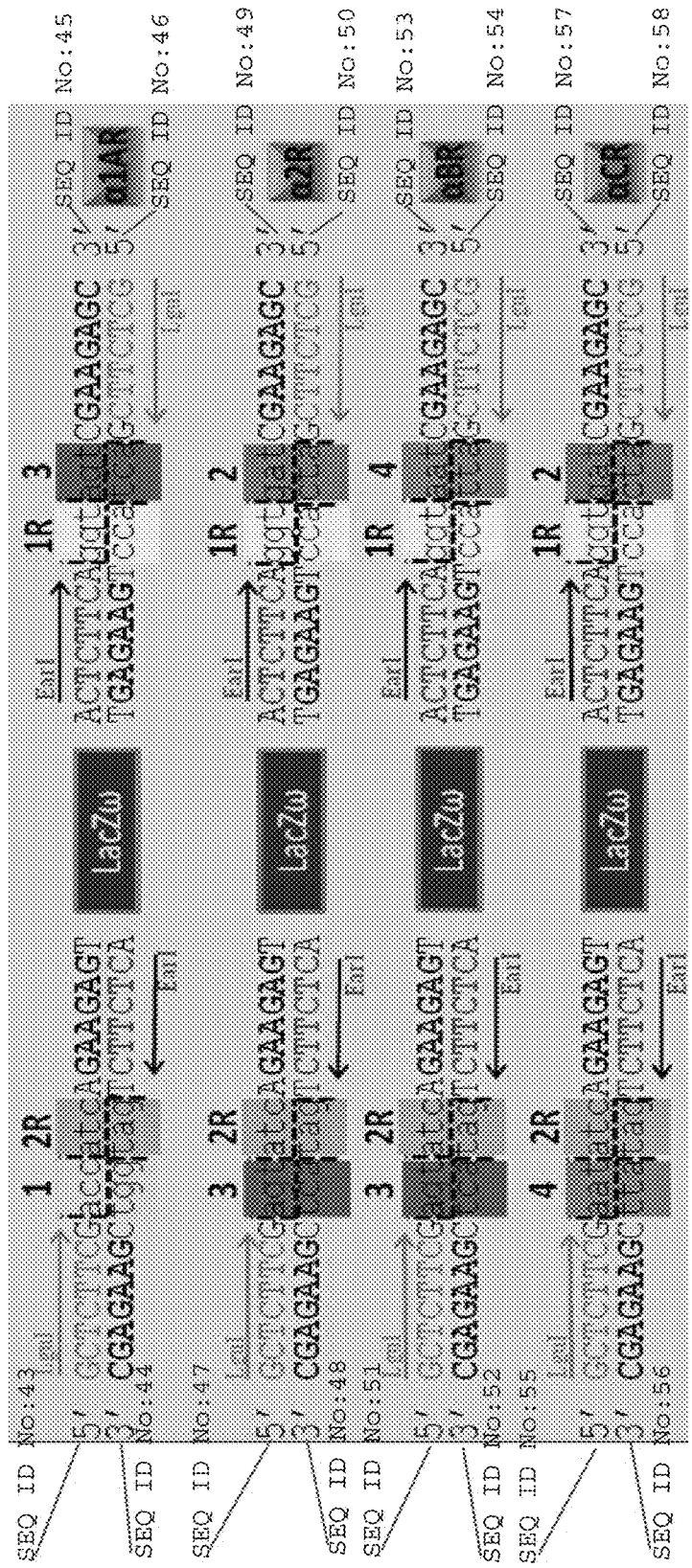
FIG. 6. Alpha antisense/reverse (αR) family of vectors (α1AR, α2R, αBR, αCR). All αR vectors, purple font is EarI restriction enzyme binding site; orange font is LguI binding site; yellow highlight indicates signature element 1 (forward strand, acc; reverse strand, tgg) or signature element 1R (forward strand, ggt; reverse strand, cca); green highlight indicates signature element 2 (forward strand, gat; reverse strand, cta) or signature element 2R (forward strand, acc; reverse strand, tgg); red highlight indicates signature element 3 (forward strand, atc; reverse strand, tag); blue highlight indicates signature element 4 (forward strand, aat; reverse strand, tta); dotted lines indicate location of cleavage by restriction enzyme. (α1AR) The α1AR vector has adjacent signature elements 1 and 2R upstream of the marker gene, and adjacent signature elements 1R and 3 downstream of the marker; an LguI restriction enzyme site on the forward strand that leaves acc/tgg cohesive ends across signature element 1; an EarI restriction enzyme site on the reverse strand that leaves atc/tag cohesive ends across signature element 2R; an EarI restriction enzyme site on the forward strand that generates ggt/cca cohesive ends across signature element 1R; and an LguI restriction enzyme site on the reverse strand that generates agt/tca cohesive ends across signature element 3. (α2R) The α2R vector has adjacent signature elements 3 and 2R upstream of the marker gene, and adjacent signature elements 1R and 2 downstream of the marker; an LguI restriction enzyme site on the forward strand that leaves agc/tcg cohesive ends across signature element 2; an EarI restriction enzyme site on the reverse strand that leaves atc/tag cohesive ends across signature element 2R; an EarI restriction enzyme site on the forward strand that generates ggt/cca cohesive ends across signature element 1R; and an LguI restriction enzyme site on the reverse strand that generates gat/cta cohesive ends across signature element 2. (αBR) The αBR vector has adjacent signature elements 3 and 2R upstream of the marker gene, and adjacent signature elements 1R and 4 downstream of the marker; an LguI restriction enzyme site on the forward strand that leaves agt/tca cohesive ends across signature element 3; an EarI restriction enzyme site on the reverse strand that leaves atc/tag cohesive ends across signature element 2R; an EarI restriction enzyme site on the forward strand that generates ggt/cca cohesive ends across signature element 1R; and an LguI restriction enzyme site on the reverse strand that generates aat/tta cohesive ends across signature element 4. (αCR) The αCR vector has adjacent signature elements 4 and 2R upstream of the marker gene, and adjacent signature elements 1R and 2 downstream of the marker; an LguI restriction enzyme site on the forward strand that leaves aat/tta cohesive ends across signature element 4; an EarI restriction enzyme site on the reverse strand that leaves atc/tag cohesive ends across signature element 2R; an EarI restriction enzyme site on the forward strand that generates ggt/cca cohesive ends across signature element 1R; and an LguI restriction enzyme site on the reverse strand that generates gat/cta cohesive ends across signature element 2.
Figure 7:
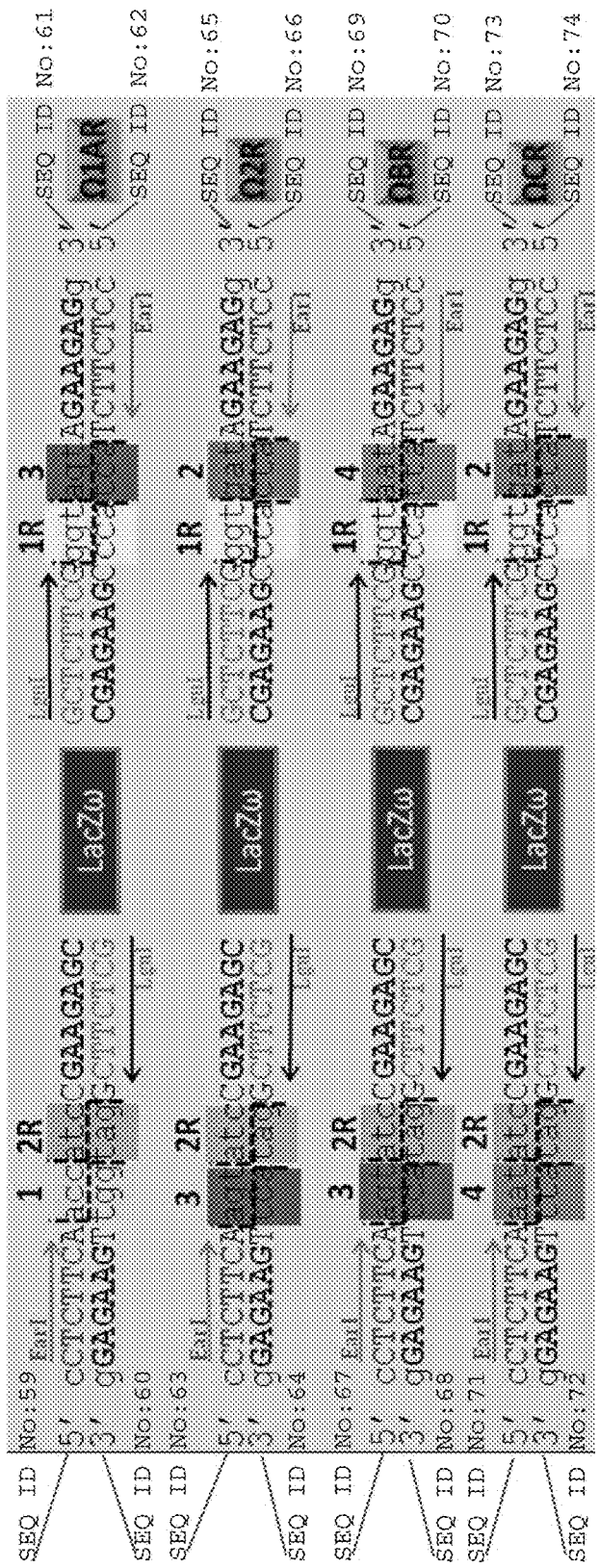
FIG. 7. Omega antisense/reverse (ΩR) family of vectors (Ω1AR, Ω2R, ΩBR, ΩCR). All ΩR vectors, purple font is EarI restriction enzyme binding site; orange font is LguI binding site; yellow highlight indicates signature element 1 (forward strand, acc; reverse strand, tgg) or signature element 1R (forward strand, ggt; reverse strand, cca); green highlight indicates signature element 2 (forward strand, gat; reverse strand, cta) or signature element 2R (forward strand, acc; reverse strand, tgg); red highlight indicates signature element 3 (forward strand, atc; reverse strand, tag); blue highlight indicates signature element 4 (forward strand, aat; reverse strand, tta); dotted lines indicate location of cleavage by restriction enzyme. (Ω1AR) The Ω1AR vector has adjacent signature elements 1 and 2R upstream of the marker gene, and adjacent signature elements 1R and 3 downstream of the marker; an EarI restriction enzyme site on the forward strand that leaves acc/tgg cohesive ends across signature element 1; an LguI restriction enzyme site on the reverse strand that leaves atc/tag cohesive ends across signature element 2R; an Lgu restriction enzyme site on the forward strand that generates ggt/cca cohesive ends across signature element 1R; and an EarI restriction enzyme site on the reverse strand that generates agt/tca cohesive ends across signature element 3. (Ω2R) The Ω2R vector has adjacent signature elements 3 and 2R upstream of the marker gene, and adjacent signature elements 1R and 2 downstream of the marker; an EarI restriction enzyme site on the forward strand that leaves agc/tcg cohesive ends across signature element 2; an LguI restriction enzyme site on the reverse strand that leaves atc/tag cohesive ends across signature element 2R; an LguI restriction enzyme site on the forward strand that generates ggt/cca cohesive ends across signature element 1R; and an EarI restriction enzyme site on the reverse strand that generates gat/cta cohesive ends across signature element 2. (ΩBR) The ΩBR vector has adjacent signature elements 3 and 2R upstream of the marker gene, and adjacent signature elements 1R and 4 downstream of the marker; an EarI restriction enzyme site on the forward strand that leaves agt/tca cohesive ends across signature element 3; an LguI restriction enzyme site on the reverse strand that leaves atc/tag cohesive ends across signature element 2R; an LguI restriction enzyme site on the forward strand that generates ggt/cca cohesive ends across signature element 1R; and an EarI restriction enzyme site on the reverse strand that generates aat/tta cohesive ends across signature element 4. (ΩCR) The ΩCR vector has adjacent signature elements 4 and 2R upstream of the marker gene, and adjacent signature elements 1R and 2 downstream of the marker; an EarI restriction enzyme site on the forward strand that leaves aat/tta cohesive ends across signature element 4; an LguI restriction enzyme site on the reverse strand that leaves atc/tag cohesive ends across signature element 2R; an LguI restriction enzyme site on the forward strand that generates ggt/cca cohesive ends across signature element 1R; and an EarI restriction enzyme site on the reverse strand that generates gat/cta cohesive ends across signature element 2.
Figure 8:
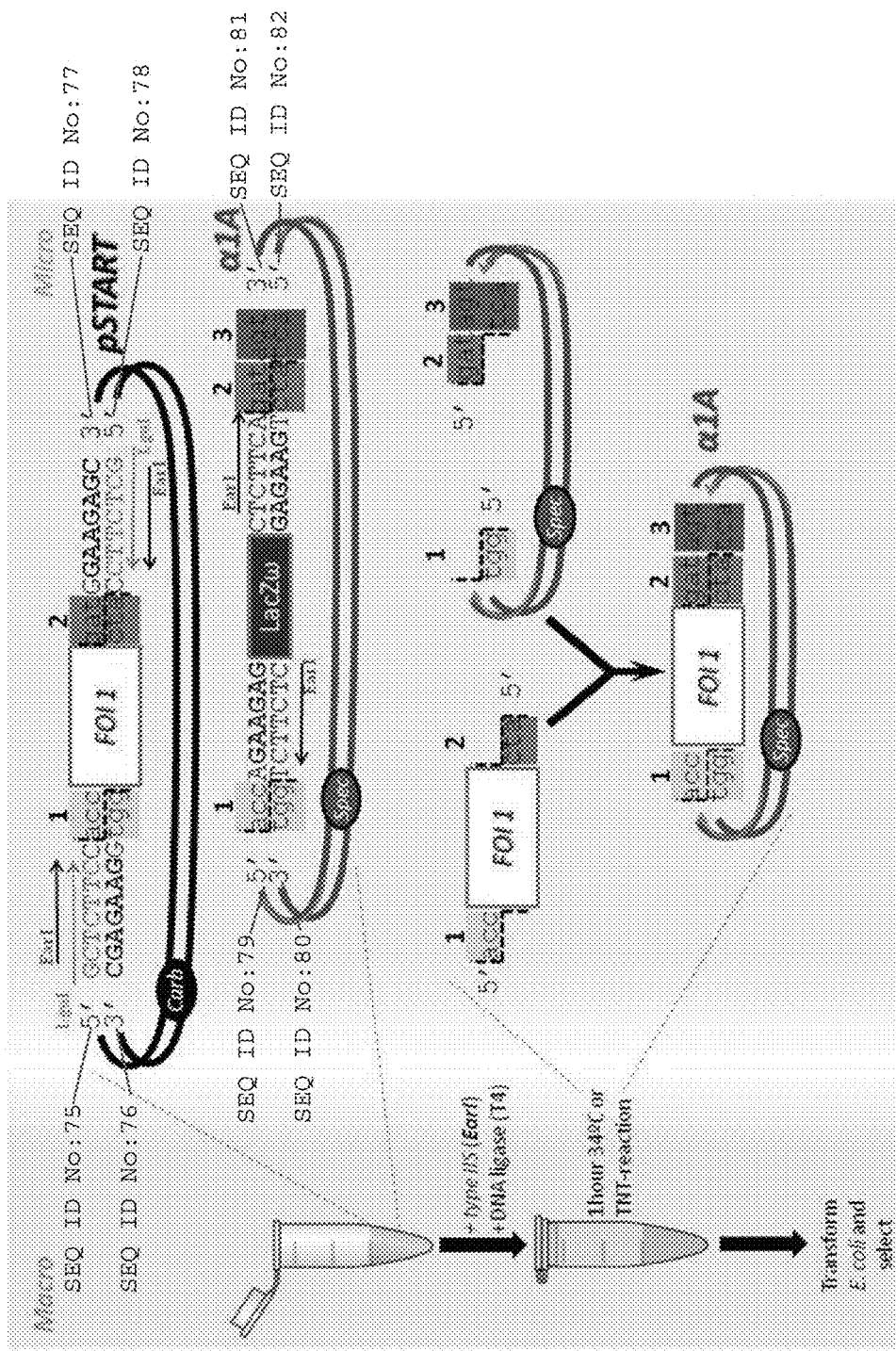
FIG. 8. Example of initial cloning of fragment of interest (FOI) into α1A vector. FOI in pSTART vector (carbenicillin (Carb) resistance) is combined with α1A vector (spectinomycin (Spec) resistance, LacZ+ selectable marker) in a reaction tube with EarI enzyme and T4 DNA ligase in a "one pot" restriction-ligation reaction. Cleavage of pSTART vector with EarI cleaves FOI from pSTART, generating signature element 1 (acc) cohesive end on the 5' end of the forward strand of FOI, and reverse complement of signature element 2 (cta) cohesive end on 5' of reverse strand carrying FOI. Cleavage of α1A vector leaves reverse complement of signature element 1 (tgg) cohesive end on 5' end of reverse strand of α1A vector, and signature element 2 (gat) cohesive end on 5' end of forward strand of α1A vector. Signature elements 1 and 2 join with their reverse complement sequences to join the FOI to the α1A vector. The resulting vector is transformed into a suitable host and selected by presence of spectinomycin resistance and loss of LacZ marker.

| SEQUENCE | SEQ ID NO: | LOCATION OF SEQUENCE |
|---|---|---|
| GCTCTTCGACCATCAGAAGAGT | SEQ ID NO: 43 | FIG. 6 |
| ACTCTTCTGATGGTCGAAGAGC | SEQ ID NO: 44 | FIG. 6 |
| ACTCTTCAGGTAGTCGAAGAGC | SEQ ID NO: 45 | FIG. 6 |
| GCTCTTCGACTACCTGAAGAGT | SEQ ID NO: 46 | FIG. 6 |
| GCTCTTCGAGTATCAGAAGAGT | SEQ ID NO: 47 | FIG. 6 |
| ACTCTTCTGATACTCGAAGAGC | SEQ ID NO: 48 | FIG. 6 |
| ACTCTTCAGGTGATCGAAGAGC | SEQ ID NO: 49 | FIG. 6 |
| TGAGAAGTCCACTAGCTTCTCG | SEQ ID NO: 50 | FIG. 6 |
| GCTCTTCGAGTATCAGAAGAGT | SEQ ID NO: 51 | FIG. 6 |
| CATCTTCTGATACTCGAAGAGC | SEQ ID NO: 52 | FIG. 6 |
| ACTCTTCAGGTAATCGAAGAGC | SEQ ID NO: 53 | FIG. 6 |
| GCTCTTCGATTACCTGAAGAGT | SEQ ID NO: 54 | FIG. 6 |
| GCTCTTCGAATATCAGAAGAGT | SEQ ID NO: 55 | FIG. 6 |
| ACTCTTCTGATATTCGAAGAGC | SEQ ID NO: 56 | FIG. 6 |
| ACTCTTCAGGTAATCGAAGAGC | SEQ ID NO: 57 | FIG. 6 |
| TGAGAAGTCCACTAGCTTCTCG | SEQ ID NO: 58 | FIG. 6 |
| CCTCTTCAACCATCCGAAGAGC | SEQ ID NO: 59 | FIG. 7 |
| GCTCTTCGGATGGTTGAAGAGG | SEQ ID NO: 60 | FIG. 7 |
| GCTCTTCGGGTAGTAGAAGAGG | SEQ ID NO: 61 | FIG. 7 |
| CCTCTTCTACTACCCGAAGAGC | SEQ ID NO: 62 | FIG. 7 |
| CCTCTTCAAGTATCCGAAGAGC | SEQ ID NO: 63 | FIG. 7 |
| GCTCTTCGGATACTTGAAGAGG | SEQ ID NO: 64 | FIG. 7 |
| GCTCTTCGGGTGATAGAAGAGG | SEQ ID NO: 65 | FIG. 7 |
| CCTCTTCTATCACCCGAAGAGC | SEQ ID NO: 66 | FIG. 7 |
| CCTCTTCAAGTATCCGAAGAGC | SEQ ID NO: 67 | FIG. 7 |
| GCTCTTCGGATACCTGAAGAGG | SEQ ID NO: 68 | FIG. 7 |
| GCTCTTCGGGTAATAGAAGAGG | SEQ ID NO: 69 | FIG. 7 |
| CCTCTTCTATTACCCGAAGAGC | SEQ ID NO: 70 | FIG. 7 |
| CCTCTTCAAATATCCGAAGAGC | SEQ ID NO: 71 | FIG. 7 |
| GCTCTTCGGATATTTGAAGAGG | SEQ ID NO: 72 | FIG. 7 |
| GCTCTTCGGGTGATAGAAGAGG | SEQ ID NO: 73 | FIG. 7 |
| CCTCTTCTATCACCCGAAGAGC | SEQ ID NO: 74 | FIG. 7 |
| GCTCTTCCACC | SEQ ID NO: 75 | FIG. 8 |
| GGTGGAAGAGC | SEQ ID NO: 76 | FIG. 8 |
| GATGGAAGAGC | SEQ ID NO: 77 | FIG. 8 |
| GCTCTTCCATC | SEQ ID NO: 78 | FIG. 8 |
| ACCAGAAGAG | SEQ ID NO: 79 | FIG. 8 |
| CTCTTCTGGT | SEQ ID NO: 80 | FIG. 8 |

TABLE I-continued (Sequences In FIGS. And Detailed Description)

Figure 9:
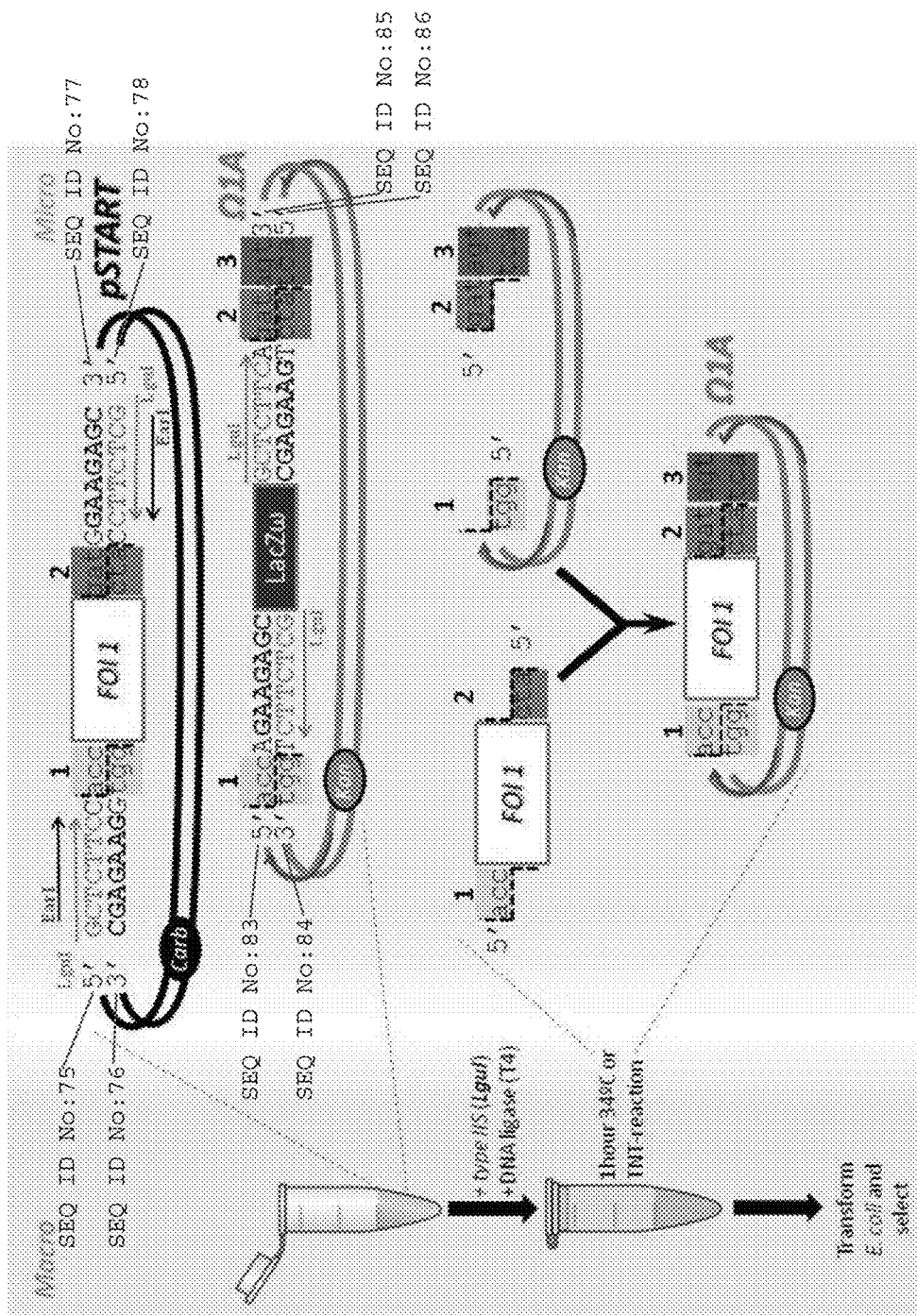
FIG. 9. Example of initial cloning of fragment of interest (FOI) into Ω1A vector. FOI in pSTART vector (carbenicillin (Carb) resistance) is combined with Ω1A vector (kanamycin (Kan) resistance, LacZ+ selectable marker) in a reaction tube with LguI enzyme and T4 DNA ligase in a "one pot" restriction-ligation reaction. Cleavage of pSTART vector with LguI cleaves FOI from pSTART, generating signature element 1 (acc) cohesive end on the 5' end of the forward strand of FOI, and reverse complement of signature element 2 (cta) cohesive end on 5' of reverse strand carrying FOI. Cleavage of Ω1A vector leaves reverse complement of signature element 1 (tgg) cohesive end on 5' end of reverse strand of Ω1A vector, and signature element 2 (gat) cohesive end on 5' end of forward strand of Ω1A vector. Signature elements 1 and 2 join with their reverse complement sequences to join the FOI to the Ω1A vector. The resulting vector is transformed into a suitable host and selected by presence of kanamycin resistance and loss of LacZ marker.
Figure 10:
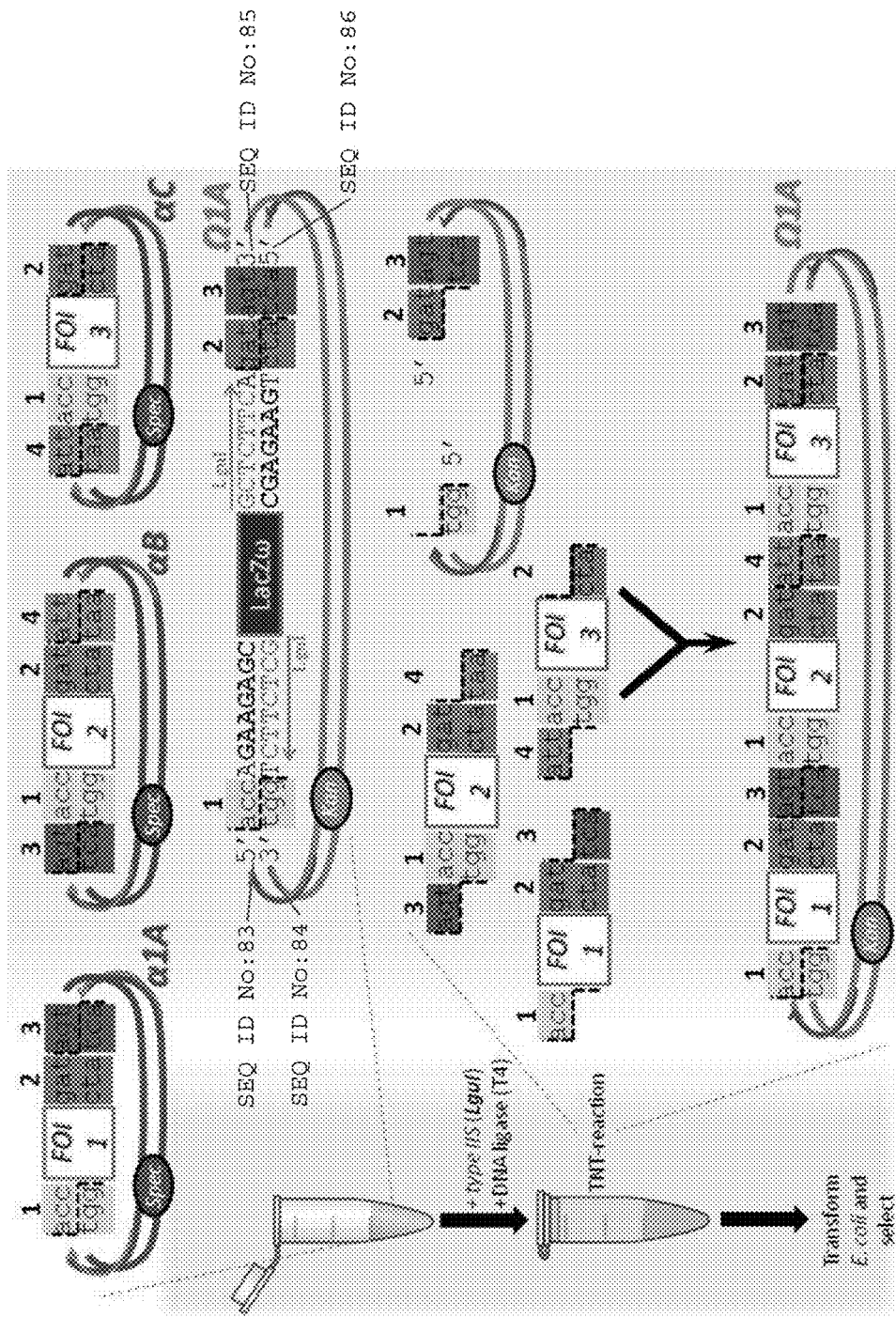
FIG. 10. Example of cloning loop from α vectors to Ω vectors. FOI 1 is cloned into α1A vector; FOI 2 is cloned into αB vector; FOI 3 is cloned into αC vector. These vectors are combined with Ω1A vector in one pot reaction with LguI and DNA ligase. Cleavage of α1A with LguI leaves cohesive end signature elements 1 (forward strand of FOI 1) and 3 (reverse strand of FOI 1); cleavage of αB leaves cohesive end signature elements 3 (forward strand of FOI 2) and 4 (reverse strand of FOI 2); cleavage of αC leaves cohesive end signature elements 4 (forward strand of FOI 3) and 2 (reverse strand of FOI 3). Cleavage of Ω1A vector leaves signature element 1 cohesive end on 5' end of reverse strand of Ω1A vector, and signature element 2 cohesive end on 5' end of forward strand of Ω1A vector. The fragments are joined with the vector in the following order: FOI 1 joins to the Ω1A vector at signature element 1, and to FOI 2 at signature element 3; FOI 2 joins to FOI 3 at signature element 4; FOI 3 joins to the Ω1A vector at signature element 2. Thus, FOI 1-3 are joined in correct order and orientation into the Ω1A vector. The expression cassette containing FOI 1-3 can then be cloned, as desired, into an α family vector, using the EarI restriction enzyme to cleave the Ω vector at signature elements 1 and 3.

| SEQUENCE | SEQ ID NO: | LOCATION OF SEQUENCE |
|---|---|---|
| CTCTTCAGATAGT | SEQ ID NO: 81 | FIG. 8 |
| ACTATCTGAAGAG | SEQ ID NO: 82 | FIG. 8 |
| ACCAGAAGAGC | SEQ ID NO: 83 | FIG. 9 |
| GCTCTTCTGGT | SEQ ID NO: 84 | FIG. 9 |
| GCTCTTCAGATAGT | SEQ ID NO: 85 | FIG. 9 |
| ACTATCTGAAGAGC | SEQ ID NO: 86 | FIG. 9 |
| CACTGCCAGTTGCTCTTCATATAGCA | SEQ ID NO: 87 | FIG. 15A |
| CACTGCCAGTTCCTCTTCATATAGCA | SEQ ID NO: 88 | FIG. 15A |
| CACTATGAGTTGCTCTTCATATAGCA | SEQ ID NO: 89 | FIG. 15A |
| CACTGGCTGCCGCTCTTCATATAGCA | SEQ ID NO: 90 | FIG. 15A |
| GCCAGTTGCTCTTC | SEQ ID NO: 91 | FIG. 15A |
| GATTGCCAGTTACTCTTCTGGGACCT | SEQ ID NO: 92 | FIG. 15A |
| GATTGCCAGACTCTCTTCTGGGACCT | SEQ ID NO: 93 | FIG. 15A |
| GATTGGCTGCCACTCTTCTGGGACCT | SEQ ID NO: 94 | FIG. 15A |
| TGACACATGCAGCTCTTCCACCNNNN | SEQ ID NO: 95 | FIG. 15B |
| TGAGCGAGGAAGCTCTTCCATCNNNN | SEQ ID NO: 96 | FIG. 15B |
| CATGCCTGCAGGCTCTTCGAVYAYCN | SEQ ID NO: 97 | FIG. 15B |
| AATCTGATCCAGCTCTTCGAYYAYCN | SEQ ID NO: 98 | FIG. 15B |
| CATGCCTGCAGACTCTTCAACCNNNN | SEQ ID NO: 99 | FIG. 15B |
| ATGCCTGCAGMCCTCTTCAAVYAYCN | SEQ ID NO: 100 | FIG. 15B |
| AATCTGATCCMMCTCTTCTAYYAYCN | SEQ ID NO: 101 | FIG. 15B |

See below      SEQ ID NO: 102 FIG. 16A
GATCCCGGGTCAATAGCATTCTCACCAATAAAAAACGCCCGGCGGCAACCGAGCGTTCTGAACA
AATCCAGATGGAGTTCTGAGGTCATTACTGTCAACAGGAGTCCAAGCGGCCGCTTTTTTTACCT
CCTAAAAGTTAAACAAAATTATTTCTAGAGGGAAACCGTTGTGGAATTGTGAGCGCTCACCATA
TTATAATTGTTATCCGCTCACAAAGCAAATAAATTTTTCATGATTTCACTGTGCATGAAGCTCG
TAATTGTTATCCGCTCACAATTaaactcatgagcccgaagtggcgagcccgatcttccccatcg
gtgatgtcggcgatataggcgccagcaaccgcacctgtggcgccggtgatgccggtgcgtccgg
cgtagaggatcgagatctcgatcccgcgaaatAATACGACTCACTATAGGGGAATTGTGAGCGG
ATAACAATTCCCCTCTAGAATTGTTTAACTTTAAGAAGGAGATATACCTGGGTCTGCCTCCGCT
GCTGAGCCTGCCGAGCAATAGCGCACCGCGTAGCCTGGGTCGTGTTGAACCGGAAGTTGTTGAT
TTTATGGTTAGCCTGGCCGAAGCACCGCGTGGTGGTCGTGTTCTGGAACCGGCATGTGCCCATG
GTCCGTTTCTGCGTGGTGAAGCACATGGCACCGGTTATCGTTTTGTTGGTGTTGAAATTGATCC
GAAAGCACTGGATCTGCCACCGTGGGCAGAAGGTATTCTGGCAGAGCTGTGGGAACCGGGTGAA
GCATTTGATCTGATTCTGGGTAATCCGCCTTATGGTATTGTTGGTGAAGCAAGCAAATATCCGA
TCCATGTTTTTGTGAAAGATCTGTACAAAAAAGCCTTTAGCACCTGGAAAGGCAAATATAACCT
GTATGGTGCCTTTCTGGAAAAAGCAGTTCGTCTGCTGAAACGTGTTCTGGTTTTTGTTGTTCCG
GCAACCTGGCTGGTGCTGGAAGATTTTGCACTGCTGCGTGAATTTCTGGCACGTGAAGGTAAAA
CCAGCGTTCTGGGTGAAGTTTTTCCGCAGAAAAAAGTTAGCGCAGTGGTTATTCGTTTTCAGAA
AAGCGGTAAAGGTCTGAGCCTGTGGGATACCCAAGAAGCGGTTTTACCCCGATTCTGTGGGCTG
AATATCCGCATTGGGAAGGTGAAATTATTCGCTTTGAAACCGAAGAAACCCGCAAACTGGAAAT
TTTGCCGCTGGGTGACCTGTTTCATATCCGTTTTGCAGCACGTAGTCCGGAATTCAAAAAACAT
CCGGCAGTTCGTAAAGAACCGGGTCCGGGTCTGGTTCTGACCGGTCGTAATCTGAAACCTGGTT
GGGTTGATTATGAAAAAAATCATAGCGGTCTGTGGATGCCGAAAGAACGTGCAAAAGAACTGTT
TTATGCAACACCGCATCTGGTTGTTGCACATACCAAAGGCACCCGTGTTGTTGCAGCATGGGAT
GAACGTGCATATCCGTGGCGTGAAGAATTGCTGCCTAAAGAAGGTGTTCGTCTGGATCCGAAAG
GCCTGGTTCAGTGGCTGAATAGCGAAGCAATGCAGAAACATGTTCGTACCCTGTATCGTGTTCC
GCATCTGACCCTGCGTATGCTGGAACGTCTGCCGGTTCGTCGTAATATGGTTTTCATACCAGT
CCGGAAAGCGCACGTAACTTTTAACCGAAAGGAAGCTGAGTTGGCTGCTGCCACCGCTGAGCAA
TAACTAGCATAACCCCTTGGGGCCTCTAAACGGGTCTTGAGGGGTTTTTTG GGCCACTCGAGC
ACCTAGGAG

TABLE II

| Name | Length | Sequence | SEQ ID NO: |
|---|---|---|---|
| Primers | | | |
| pUPD-FW1 | 32 | GCTCTTCCACCCCGGGGCTGGCTTAACTATGC | SEQ ID NO: 103 |
| pUPD-RW1 | 27 | TGGCGTAATAGCGAGGAGGCCCGCACC | SEQ ID NO: 104 |
| pUPD-FW2 | 27 | GGTGCGGGCCTCCTCGCTATTACGCCA | SEQ ID NO: 105 |
| pUPD-RW2 | 31 | CTCTAGAGGATCCCCTGGTACCGAGCTCGAA | SEQ ID NO: 106 |
| pUPD-FW3 | 31 | TTCGAGCTCGGTACCAGGGGATCCTCTAGAG | SEQ ID NO: 107 |
| pUPD-RW3 | 35 | GCTCTTCCATCCCGGGCGCCCAATACGCAAACCGC | SEQ ID NO: 108 |
| pUPD-FW4 | 34 | CCCGGGATGGAAGAGCTTCCTCGCTCACTGACTC | SEQ ID NO: 109 |
| pUPD-RW4 | 41 | GCTTCAATAATATTGAAAAAGGAGGAGTATGAGTATTCAAC | SEQ ID NO: 110 |
| pUPD-FW5 | 41 | GTTGAATACTCATACTCCTCCTTTTTCAATATTATTGAAGC | SEQ ID NO: 111 |
| pUPD-RW5 | 33 | GCCCCGGGGTGGAAGAGCTGCATGTGTCAGAGG | SEQ ID NO: 112 |
| pUPD-RW3.1 | 27 | CAGCTATGACCATGATTACGGATTCAC | SEQ ID NO: 113 |
| FW_adap | 67 | CTCTTCCACCCCGGGGCTGGCTTAACTATGCGGCATCAGAGCTTATTTTTGACACCAGACCAACTGG | SEQ ID NO: 114 |
| pUPD-FW3.1 | 31 | CGTAATCATGGTCATAGCTGTTTCCTGTGTG | SEQ ID NO: 115 |
| pUPD-RW5 | 33 | GCCCCGGGGTGGAAGAGCTGCATGTGTCAGAGG | SEQ ID NO: 116 |
| KStrat2_TNT-Fw | 26 | CATTACAGCTTACGAACCGAACGAGG | SEQ ID NO: 117 |
| KStrat2_TNT-Rw | 21 | GCAGCGAGTCAGTGAGCGAGG | SEQ ID NO: 118 |
| Kan_to_O-FW2 | 25 | GGAATTTATGCCGCTTCCGACCATC | SEQ ID NO: 119 |
| KStrat2_TOP-Rw | 21 | CCTCGCTCACTGACTCGCTGC | SEQ ID NO: 120 |
| KStrat2_TOP-FW | 37 | TCGGTTCGTAAGCTGTAATGTTCCTGGCAGCTCTGGC | SEQ ID NO: 121 |
| Kan_to_O-RW1 | 25 | GATGGTCGGAAGCGGCATAAATTCC | SEQ ID NO: 122 |
| αΩVector_FW | 24 | TGGATCAGATTGTCGTTTCCCGCC | SEQ ID NO: 123 |
| αΩVector_RW | 24 | CTGCAGGCATGCAGCTCGAATTAT | SEQ ID NO: 124 |
| aO_vector-nested-RW | 27 | GCTCGAATTATCGATCATGAGCGGAGA | SEQ ID NO: 125 |
| aO_vector-nested-FW | 30 | GTTTCCCGCCTTCAGTTTAAACTATCAGTG | SEQ ID NO: 126 |
| PCR2_to_αVector-Fw | 24 | GCTGCATGCCTGCAGGCTCTTCGA | SEQ ID NO: 127 |
| PCR2_to_αVector-Rw | 38 | GGG AAA CGA CAA TCT GATCCA GCT CTT CGA | SEQ ID NO: 128 |
| α1A-Fw | 55 | GCAGGCTCTTCGACCAGAAG AGT GGC TTA ACT ATG CGG CAT CAG AGC TCT GAA GAG | SEQ ID NO: 129 |
| α1A-Rw | 63 | GATCCA GCT CTT CGA CTA T ATA CGC AAA CCG CCT CTC CC | SEQ ID NO: 130 |
| α2-Fw | 58 | GCAGGCTCTTCGAGTACCAGA AGAGT GGC TTA ACT ATG CGG CAT CAG AGC | SEQ ID NO: 131 |
| α2-Rw | 58 | GATCCA GCT CTT CGA TCT GAA GAG T ATA CGC AAA CCG CCT CTC CC | SEQ ID NO: 132 |
| αB-Fw | 58 | GCAGGCTCTTCGAGTACCAGA AGAGT GGC TTA ACT ATG CGG CAT CAG AGC GATCCAGCT | SEQ ID NO: 133 |
| αB-Rw | 62 | CTT CGA TTA ATA CGC AAA CCG CCT CTC CC | SEQ ID NO: 134 |
| αC-Fw | 58 | GCAGGCTCTTCGAATACCAGA AGAGT GGC TTA ACT ATG CGG CAT CAG AGC | SEQ ID NO: 135 |
| αC-Rw | 58 | GATCCAGCT CTT CGA TCT GAA GAG T ATA CGC AAA CCG CCT CTC CC | SEQ ID NO: 136 |
| α1R-Fw | 58 | GCAGGCTCTTCGACCATCAGA AGAGT GGC TTA ACT ATG CGG CAT CAG AGC | SEQ ID NO: 137 |
| α1R-Rw | 62 | GATCCAGCT CTT CGA CTA CCT GAA GAG T ATA CGC AAA CCG CCT CTC CC | SEQ ID NO: 138 |
| α2R-Fw | 58 | GCAGGCTCTTCGAGTATCAGA AGAGT GGC TTA ACT ATG CGG CAT CAG AGC | SEQ ID NO: 139 |
| α2R-Rw | 62 | GATCCAGCT CTT CGA TCA CCT GAA GAG T ATA CGC AAA CCG CCT CTC CC | SEQ ID NO: 140 |
| PCR2_to_ΩVector-Fw | 22 | GCTGCATGCCTGCAGACTCTT C | SEQ ID NO: 141 |
| PCR2_to_ΩVector-Rw | 34 | GGG AAA CGA CAA TCT GATCCA ACTCTTC | SEQ ID NO: 142 |
| Ω1A-Fw | 56 | GCAG ACTCTTCAACCCGAAGAGC GGC TTA ACT ATG CGG CAT CAG AGC | SEQ ID NO: 143 |
| Ω1A-Rw | 63 | GATCCA ACT CTT CTA CTA TCC GAA GAG C ATA CGC AAA CCG CCT CTC CC | SEQ ID NO: 144 |
| Ω2-Fw | 59 | GCAG ACTCTTCAAGTACCCGAAGAG C GGC TTA ACT ATG CGG CAT CAG AGC | SEQ ID NO: 145 |
| Ω2-Rw | 59 | GATCCA ACT CTT CTA TCC GAA GAG C ATA CGC AAA CCG CCT CTC CC | SEQ ID NO: 146 |
| ΩB-Fw | 59 | GCAG ACTCTTCAAGTACCCGAAGAG C GGC TTA ACT ATG CGG CAT CAG AGC | SEQ ID NO: 147 |
| ΩB-Rw | 63 | GATCCA ACT CTT CTA TTA TCC GAA GAG C ATA CGC AAA CCG CCT CTC CC | SEQ ID NO: 148 |
| ΩC-Fw | 59 | GCAG ACTCTTCAAATACCCGAAGAG C GGC TTA ACT ATG CGG CAT CAG AGC | SEQ ID NO: 149 |
| ΩC-Rw | 59 | GATCCA ACT CTT CTA TCC GAA GAG C ATA CGC AAA CCG CCT CTC CC | SEQ ID NO: 150 |
| Ω1R-Fw | 59 | GCAG ACTCTTCAACCATCCGAAGAG C GGC TTA ACT ATG CGG CAT CAG AGC | SEQ ID NO: 151 |

TABLE II-continued

| Name | Length | Sequence | SEQ ID NO: |
|---|---|---|---|
| Ω1R-Rw | 63 | GATCCA ACT CTT CTA CTA CCC GAA GAG C ATA CGC AAA CCG CCT CTC CC | SEQ ID NO: 152 |
| Ω2R-Fw | 59 | GCAG ACTCTTCAAGTATCCGAAGAG C GGC TTA ACT ATG CGG CAT CAG AGC | SEQ ID NO: 153 |
| Ω2R-Rw | 63 | GATCCA ACT CTT CTA TCA CCC GAA GAG C ATA CGC AAA CCG CCT CTC CC | SEQ ID NO: 154 |
| EarI-FW1 | 31 | GTTTTTCATTACCGACGAGATCGAGGCGGAG | SEQ ID NO: 155 |
| EarI-FW2 | 31 | GCGCACAGCCGACGAGCTGCAAAAAG | SEQ ID NO: 156 |
| EarI-FW3 | 31 | CAGGCGCTCTTACGCTTCCTCGCTC | SEQ ID NO: 157 |
| EarI-FW4 | 31 | TTCGCCGCCAAGTTCTTCAGCAATATC | SEQ ID NO: 158 |
| EarI-FW5 | 31 | CGAGCCCCTGATGTTCTTCGTCCAG | SEQ ID NO: 159 |
| EarI-RW1 | 31 | CTCCGCCTCGATCTCGTCGGTAATGAAAAAC | SEQ ID NO: 160 |
| EarI-RW2 | 31 | CTTTTTGCAGCTCGTCGGCTGTGCGC | SEQ ID NO: 161 |
| EarI-RW3 | 31 | GAGCGAGGAAGCGTAAGAGCGCCTG | SEQ ID NO: 162 |
| EarI-RW4 | 31 | GATATTGCTGAAGAACTTGGCGGCGAA | SEQ ID NO: 163 |
| EarI-RW5 | 31 | CTGGACGAAGAACATCAGGGGCTCG | SEQ ID NO: 164 |
| TNT-αΩ-seqRW | 22 | CTCTTAGGTTTACCCGCCAATA | SEQ ID NO: 165 |
| TNT-αΩ-seqFW | 22 | AACGTGACTCCCTTAATTCTCC | SEQ ID NO: 166 |
| pUPD_adap_met.test-FW | 43 | CTCTTCGACCCCGGGGCTGGCTTAACTATGCGGC ATCAGAGC | SEQ ID NO: 167 |
| pUPD-RW5-M_Test | 33 | GCCCCGGGGTCGAAGAGCTGCATGTGTCAGAGG | SEQ ID NO: 168 |
| pUPD-seqFW | 20 | GCCACCTGACGTCTAAGAAA | SEQ ID NO: 169 |
| pUPD-seqRW | 25 | CCTGATTCTGTGATAACCGTATTA | SEQ ID NO: 170 |
| TNT-Lumio_FW | 72 | ACATGCAGCTCTTCCACCGGTGCTGGTGGTTGCTG CCCTGGTTGCTGCGGTGGTGATGGAAGAGCTTCCT CG | SEQ ID NO: 171 |
| TNT-Lumio_RW | 72 | CGAGGAAGCTCTTCCATCACCACCGCAGCAACCAG GGCAGCAACCACCAGCACCGGTGGAAGAGCTGCAT GT | SEQ ID NO: 172 |
| TNT-GFP_FW | 35 | ACATGCAGCTCTTCCACCGTGAGCAAGGGCGAGGA | SEQ ID NO: 173 |
| TNT-GFP_RW | 38 | CGAGGAAGCTCTTCCATCCTTGTACAGCTCGTCCA TGC | SEQ ID NO: 174 |
| TNT-NLS_FW | 66 | ACATGCAGCTCTTCCACCCCTAAGAAGAAGCGTAA GGTCGAGGACCCTGATGGAAGAGCTTCCTCG | SEQ ID NO: 175 |
| TNT-NLS_RW | 66 | CGAGGAAGCTCTTCCATCAGGGTCCTCGACCTTAC GCTTCTTCTTAGGGGTGGAAGAGCTGCATGT | SEQ ID NO: 176 |
| TNT-P2A_FW | 93 | ACATGCAGCTCTTCCACCGCTACCAACTTCTCTCT CCTCAAGCAGGCTGGTGACGTCGAGGAGAACCCTG GTCCTGATGGAAGAGCTTCCTCG | SEQ ID NO: 177 |
| TNT-P2A_RW | 93 | CGAGGAAGCTCTTCCATCAGGACCAGGGTTCTCCT CGACGTCACCAGCCTGCTTGAGGAGAGAAGTTG GTAGCGGTGGAAGAGCTGCATGT | SEQ ID NO: 178 |
| TNT-T2A_FW | 96 | ACATGCAGCTCTTCCACCCGTGCTGAGGGTCGTGG TTCTCTCCTCACCTGCGGTGACGTCGAGGAGAACC CTGGTCCTGATGGAAGAGCTTCCTCG | SEQ ID NO: 179 |
| TNT-T2A_RW | 96 | CGAGGAAGCTCTTCCATCAGGACCAGGGTTCTCCT CGACGTCACCGCAGGTGAGGAGAGAACCACGACCC TCAGCACGGGTGGAAGAGCTGCATGT | SEQ ID NO: 180 |
| TNT-IbP_FW | 90 | ACATGCAGCTCTTCCACCCCTTGCTCTAACGCTGC TGACGAGGTCGCTACCCCTGAGGACGTCGAGCCTG GTGATGGAAGAGCTTCCTCG | SEQ ID NO: 181 |
| TNT-IbP_RW | 90 | CGAGGAAGCTCTTCCATCACCAGGCTCGACGTCCT CAGGGGTAGCGACCTCGTCAGCAGCGTTAGAGCAA GGGGTGGAAGAGCTGCATGT | SEQ ID NO: 182 |
| TNT-PmCherry_FW1 | 37 | ACATGCAGCTCTTCCACCATGGCAAAGGATGTGGA AG | SEQ ID NO: 183 |
| TNT-PmCherry_RW1 | 31 | GATGTATAAGAATAGGAGAGTGGCTACGAAC | SEQ ID NO: 184 |
| TNT-PmCherry_FW2 | 31 | GTTCGTAGCCACTCTCCTATTCTTATACATC | SEQ ID NO: 185 |
| TNT-PmCherry_RW2 | 37 | CGAGGAAGCTCTTCCATCAGATCTGTACAGCTCGT CC | SEQ ID NO: 186 |
| TNT-35SPro_FW | 40 | ACATGCAGCTCTTCCACCCACAACATACGAGCCGG AAGCA | SEQ ID NO: 187 |
| TNT-35SPro_RW | 42 | CGAGGAAGCTCTTCCATCCATGGCTATCGTTCGTA AATGGTG | SEQ ID NO: 188 |
| TNT-35STerm_FW | 45 | ACATGCAGCTCTTCCACCTAAGTAGCTGAATCCCG CGGCCATGCT | SEQ ID NO: 189 |
| TNT-35STerm_RW | 37 | CGAGGAAGCTCTTCCATCTCGGGCTAGGCCCGACG TC | SEQ ID NO: 190 |
| TNT-F2A_FW | 156 | ACATGCAGCTCTTCCACCCTCCTCGCTATCCACCC TACCGAGGCTCGTCACAAGCAGAAGATCGTCGCTC CTGTCAAGCAGACCCTCAACTTCGACCTCCTCAAG CTCGCTGGTGACGTCGAGTCTAACCCTGGTCCTGA TGGAAGAGCTTCCTCG | SEQ ID NO: 191 |
| TNT-F2A_RW | 156 | CGAGGAAGCTCTTCCATCAGGACCAGGGTTAGACT CGACGTCACCAGCGAGCTTGAGGAGGTCGAAGTTG AGGGTCTGCTTGACAGGAGCGACGATCTTCTGCTT GTGACGAGCCTCGGTAGGGTGGATAGCGAGGAGGG TGGAAGAGCTGCATGT | SEQ ID NO: 192 |

TABLE II-continued

| Name | Length | Sequence | SEQ ID NO: |
|---|---|---|---|
| TNT-Cas9-FW1 | 42 | ACATGCAGCTCTTCCACCATGGATTACAAGGATGATGATGAT | SEQ ID NO: 193 |
| TNT-Cas9-RW1 | 35 | GAA TCG AAA AGA AGT GCA CCG ATA AGG | SEQ ID NO: 194 |
| TNT-Cas9-FW2 | 27 | CCTTATCGGTGCACTTCTTTTC GATTC | SEQ ID NO: 195 |
| TNT-Cas9-RW2 | 33 | ACT CGT AAA GAA GTG AGT GCT TTG G | SEQ ID NO: 196 |
| TNT-Cas9-FW3 | 25 | CCAAAGCACTCACTTCTTTACGAGT | SEQ ID NO: 197 |
| TNT-Cas9-RW3 | 30 | TGC TCG TGA AGT GAA TCT CCC TG | SEQ ID NO: 198 |
| TNT-Cas9-FW4 | 23 | CAGGGAGATTCACTTCACAGCA | SEQ ID NO: 199 |
| TNT-Cas9-RW4 | 31 | CTT AGA TGG AAG TGC AAG CTC GTT | SEQ ID NO: 200 |
| TNT-Cas9-FW5 | 24 | AACGAGCTTGCACTTCCATCTAAG | SEQ ID NO: 201 |
| TNT-Cas9-RW5 | 45 | CGAGGAAGCTCTTCCATCTTT ATG CCT GCA GGT CGC GAG | SEQ ID NO: 202 |
| Ω2-lefCC-FW | 51 | CGAGCTGCATGCCTGCAGCCCTCTTCAAGTACCCG AAGAGCGGCTTAACTA | SEQ ID NO: 203 |
| Ω2-lefCC-RW | 51 | TAGTTAAGCCGCTCTTCGGGTACTTGAAGAGGGCT GCAGGCATGCAGCTCG | SEQ ID NO: 204 |
| ΩC-lefCC-FW | 51 | CGAGCTGCATGCCTGCAGCCCTCTTCAAATACCCG AAGAGCGGCTTAACTA | SEQ ID NO: 205 |
| ΩC-lefCC-RW | 51 | TAGTTAAGCCGCTCTTCGGGTATTTGAAGAGGGCT GCAGGCATGCAGCTCG | SEQ ID NO: 206 |
| Ω1R-lefCC-FW | 51 | CGAGCTGCATGCCTGCAGCCCTCTTCAACCATCCG AAGAGCGGCTTAACTA | SEQ ID NO: 207 |
| Ω1R-lefCC-RW | 51 | TAGTTAAGCCGCTCTTCGGATGGTTGAAGAGGGCT GCAGGCATGCAGCTCG | SEQ ID NO: 208 |
| Ω2R-lefCC-FW | 51 | CGAGCTGCATGCCTGCAGCCCTCTTCAAGTATCCG AAGAGCGGCTTAACTA | SEQ ID NO: 209 |
| Ω2R-lefCC-RW | 51 | TAGTTAAGCCGCTCTTCGGATACTTGAAGAGGGCT GCAGGCATGCAGCTCG | SEQ ID NO: 210 |
| ΩB-rigCC-FW | 84 | GTTTGCGTATGCTCTTCGGATAATAGAAGAGGGGG ATCAGATTGTCGTTTCCCGCCTTCAGTTTAAACTA TCAGTGTTTGACAG | SEQ ID NO: 211 |
| ΩB-rigCC-RW | 84 | CTGTCAAACACTGATAGTTTAAACTGAAGGCGGGA AACGACAATCTGATCCCCCTCTTCTATTATCCGAA GAGCATACGCAAAC | SEQ ID NO: 212 |
| Ω1R-rigCC-FW | 84 | GTTTGCGTATGCTCTTCGGGTAGTAGAAGAGGGGG ATCAGATTGTCGTTTCCCGCCTTCAGTTTAAACTA TCAGTGTTTGACAG | SEQ ID NO: 213 |
| Ω1R-rigCC-RW | 84 | CTGTCAAACACTGATAGTTTAAACTGAAGGCGGGA AACGACAATCTGATCCCCCTCTTCTACTACCCGAA GAGCATACGCAAAC | SEQ ID NO: 214 |
| Ω2R-rigCC-FW | 84 | GTTTGCGTATGCTCTTCGGGTGATAGAAGAGGGGG ATCAGATTGTCGTTTCCCGCCTTCAGTTTAAACTA TCAGTGTTTGACAG | SEQ ID NO: 215 |
| Ω2R-rigCC-RW | 84 | CTGTCAAACACTGATAGTTTAAACTGAAGGCGGGA AACGACAATCTGATCCCCCTCTTCTATCACCCGAA GAGCATACGCAAAC | SEQ ID NO: 216 |
| rGUS-FW1 | 39 | ACATGCAGCTCTTCCACCATGTTACGTCCTGTAGA AACC | SEQ ID NO: 217 |
| rGUS-RW1 | 29 | CGA GCA TCT CCT CAG CGT AAG G | SEQ ID NO: 218 |
| rGUS-FW2 | 29 | CCT TAC GCT GAG GAG ATG CTC G | SEQ ID NO: 219 |
| rGUS-RW2 | 29 | TGA CTG CCT CCT CGC TGT ACA G | SEQ ID NO: 220 |
| rGUS-FW3 | 29 | CTG TAC AGC GAG GAG GCA GTC A | SEQ ID NO: 221 |
| rGUS-RW3 | 30 | ACA CTG ATA CTC CTC ACT CCA CA | SEQ ID NO: 222 |
| rGUS-FW4 | 30 | TGT GGA GTG AGG AGT ATC AGT GT | SEQ ID NO: 223 |
| rGUS-RW4 | 47 | CGAGGAAGCTCTTCCATCTTG TTT GCC TCC CTG CTG CGG T | SEQ ID NO: 224 |
| Hig-CodA-FW1 | 39 | ACATGCAGCTCTTCCACCATGAAAAAGCCTGAACT CACC | SEQ ID NO: 225 |
| Hig-CodA-RW1 | 29 | CAC AGC CCC TCC TCG CCT GGT A | SEQ ID NO: 226 |
| Hig-CodA-FW2 | 29 | TAC CAG GCG AGG AGG GGC TGT G | SEQ ID NO: 227 |
| Hig-CodA-RW2 | 29 | CGT AAC GCC TCC TCC AGC AAC G | SEQ ID NO: 228 |
| Hig-CodA-Fw3 | 29 | CGT TGC TGG AGG AGG CGT TAC G | SEQ ID NO: 229 |
| Hig-CodA-RW3 | 42 | CGAGGAAGCTCTTCCATCACGTTTGTAATCGATGG CTTCTGG | SEQ ID NO: 230 |
| Luc+_pUPD_FW1 | 42 | ACATGCAGCTCTTCCACCATGGAAGATGCCAAAAA CATAAAG | SEQ ID NO: 231 |
| Luc+_pUPD_RW1 | 27 | GGG CGT ATC TTT TCA TAG CCT | SEQ ID NO: 232 |
| Luc+_pUPD_FW2 | 27 | AGG CTA TGA AAA GAT ACG CCC | SEQ ID NO: 233 |
| Luc+_pUPD_RW2 | 33 | AAG AAT TGA AGT GAG TTT TCA CTG C | SEQ ID NO: 234 |
| Luc+_pUPD_FW3 | 33 | GCA GTG AAA ACT CAC TTC AAT TCT T | SEQ ID NO: 235 |
| Luc+_pUPD_RW3 | 34 | CCT CAG AAA CAG TTC TTC TTC AAA TC | SEQ ID NO: 236 |
| Luc+_pUPD_FW4 | 34 | GAT TTG AAG AAG AAC TGT TTC TGA GG | SEQ ID NO: 237 |
| CircRep-FW | 39 | ACATGCAGCTCTTCCACCGAGGGCGGTCCGCTGCC TTTT | SEQ ID NO: 238 |
| CircRep-RW | 39 | CGAGGAAGCTCTTCCATCCCTTGTTTGCCTGGCGG CAGT | SEQ ID NO: 239 |
| TaqI-Fw | 29 | AAC CGT CTA TCA GGG CGA TGG C | SEQ ID NO: 240 |
| TaqI-Rw | 29 | GGC TTT CCA CTT CCC CGA AAC C | SEQ ID NO: 241 |

TABLE II-continued

| Name | Length | Sequence | SEQ ID NO: |
|---|---|---|---|
| TaqI-Fw1.1 | 27 | CGCAAGCTTGGATCGAAGAGCTCTTAG | SEQ ID NO: 242 |
| TaqI-Rw1.1 | 27 | CTAAGAGCTCTTCGATCCAAGCTTGCG | SEQ ID NO: 243 |
| 15ntW-H.TFOs1 | 15 | AATTTGTCGCTTCTC | SEQ ID NO: 244 |
| 22ntW-H.TFOs1 | 21 | AGCCAGAATTTGTCGCTTCTC | SEQ ID NO: 245 |
| 15ntRvH.TFOs1 | 15 | CTCTTCGCTGTTTAA | SEQ ID NO: 246 |
| 22ntRvH.TFOs1 | 22 | CTCTTCGCTGTTTAAGACCGAT | SEQ ID NO: 247 |
| 15ntW-H.TFOs2 | 15 | GTTCACTGTCTTCTC | SEQ ID NO: 248 |
| 22ntW-H.TFOs2 | 22 | CCGGCGTGTTCACTGTCTTCTC | SEQ ID NO: 249 |
| 15ntRvH.TFOs2 | 15 | CTCTTCTGTCACTTG | SEQ ID NO: 250 |
| 22ntRvH.TFOs2 | 22 | CTCTTCTGTCACTTGTGCGGCC | SEQ ID NO: 251 |
| 26RvH.DNAsyn8m DW | 26 | CACTGCCAGTTGCTCTTCATATAGCA | SEQ ID NO: 252 |
| 26RvH.DNAsyn8m DW-Acridine 3' | 26 | CACTGCCAGTTGCTCTTCATA TAGCA-Acridine | SEQ ID NO: 253 |
| 5'-Acridine-DNA$_{(n)}$/BNA$^{NC}$$_{(n+)}$ | 14 | Acridine-G+C+C+A+G+T+T+GCT+CT+TC | SEQ ID NO: 254 |
| GBlocks | | | |
| TFOsynt_Uni5' | 225 | ACATGCAGCTCTTCCACCAAACTCATAACAGGGAA CTATAATTAGGACTAAAGAAGATTCAACGTACATT GATCTGACACAGTAGATTTAGTTGTCTCTTGTACA TACACAGTATCTAGGATTATTCAACGAAAACAATA TCAATTGTCTCTACAGAAACCAACGGCCAGTACTC TTTTGCCCTAAAAAGACCGTAACCCTAATTGTCAC ACTGAGAATCTAACG | SEQ ID NO: 255 |
| TFOsynt_Uni3' | 316 | TAGCAGATGCTACGATCTGTCAGCAACTGAGAAGT CTATTTGCTTTTGTGATTCAGGAATATGCTGAATT CCTGCACGAATTCATGTGCGCTGTAAAGCAGAACT ATGGAGAGAAAGTGTTGGTTCAGGTGAGCCATAGG ATACTCTCTTAAGAACTATGATTGTTGTCAGAACT ACGATAAAAGATGTCCGGAATTAATATCATACACT CATCTTTTCAGTTTGAAGATTTTGCAAACCACAAT GCGTTTGACCTTTTGTCTAAGTACAGTGATAGCTT TCTGCCACTTGTTGTATCGATGGAAGAGCTTCCTC G | SEQ ID NO: 256 |
| TFOsynt_8m1 | 210 | GTCACACTGAGAATCTAACGATTGCCAGTTACTCT TCTGGGACCTACGACGAAGGATGACTCCGTCCACG TTCTTCTTCACTGTTTGACAATAAGCTCCAATTTT CAGACTTTTCATTTCAAACTTGTGGGTCTCATTTT CCTCTGGCCTATATAAATCCACTATCCTCCACTGC CAGTTGCTCTTCATATAGCAGATGCTACGATCTGT | SEQ ID NO: 257 |
| TFOsynt_8m2 | 210 | GTCACACTGAGAATCTAACGATTAGGTCCCGCTCT TCTGGGACCTACGACGAAGGATGACTCCGTCCACG TTCTTCTTCACTGTTTGACAATAAGCTCCAATTTT CAGACTTTTCATTTCAAACTTGTGGGTCTCATTTT CCTCTGGCCTATATAAATCCACTATCCTCCACTGC CAGTTGCTCTTCATATAGCAGATGCTACGATCTGT | SEQ ID NO: 258 |
| TFOsynt_7m1 | 210 | GTCACACTGAGAATCTAACGATTGCCAGTTACTCT TCTGGGACCTACGACGAAGGATGACTCCGTCCACG TTCTTCTTCACTGTTTGACAATAAGCTCCAATTTT CAGACTTTTCATTTCAAACTTGTGGGTCTCATTTT CCTCTGGCCTATATAAATCCACTATCCTCCACTGC CAGTTCCTCTTCATATAGCAGATGCTACGATCTGT | SEQ ID NO: 259 |
| TFOsynt_5m2 | 210 | GTCACACTGAGAATCTAACGATTGCCAGACTCTCT TCTGGGACCTACGACGAAGGATGACTCCGTCCACG TTCTTCTTCACTGTTTGACAATAAGCTCCAATTTT CAGACTTTTCATTTCAAACTTGTGGGTCTCATTTT CCTCTGGCCTATATAAATCCACTATCCTCCACTAT GAGTTGCTCTTCATATAGCAGATGCTACGATCTGT | SEQ ID NO: 260 |
| TFOsynt_4m1 | 210 | GTCACACTGAGAATCTAACGATTGGCTGCCACTCT TCTGGGACCTACGACGAAGGATGACTCCGTCCACG TTCTTCTTCACTGTTTGACAATAAGCTCCAATTTT CAGACTTTTCATTTCAAACTTGTGGGTCTCATTTT CCTCTGGCCTATATAAATCCACTATCCTCCACTGG CTGCCGCTCTTCATATAGCAGATGCTACGATCTGT | SEQ ID NO: 261 |
| LacZw-central-gb | 1960 | AACGCTGCTTCGGCCTGGTAATGGCCCGCCGCCTT CCAGCGTTCGACCCAGGCGTTAGGGTCAATGCGGG TCGCTTCACTTACGCCAATGTCGTTATCCAGCGGT GCACGGGTGAACTGATCGCGCAGCGGCGTCAGCAG TTGTTTTTTATCGCCAATCCACATCTGTGAAAGAA AGCCTGACTGGCGGTTAAATTGCCAACGCTTATTA CCCAGCTCGATGCAAAAATCCATTTCGCTGGTGGT CAGATGCGGGATGCGTGGGACGCGGCGGGGAGCG TCACACTGAGGTTTTCCGCCAGACGCCACTGCTGC CAGGCGCTGATGTGCCCGGCTTCTGACCATGCGGT CGCGTTCGGTTGCACTACGCGTACTGTGAGCCAGA GTTGCCCGGCGCTCTCCGGCTGCGGTAGTTCAGGC AGTTCAATCAACTGTTTACCTTGTGGAGCGACATC | SEQ ID NO: 262 |

TABLE II-continued

| Name | Length | Sequence | SEQ ID NO: |
|---|---|---|---|
| | | CAGAGGCACTTCACCGCTTGCCAGCGGCTTACCAT<br>CCAGCGCCACCATCCAGTGCAGGAGCTCGTTATCG<br>CTATGACGGAACAGGTATTCGCTGGTCACTTCGAT<br>GGTTTGCCCGGATAAACGGAACTGGAAAAACTGCT<br>GCTGGTGTTTTGCTTCCGTCAGCGCTGGATGCGGC<br>GTGCGGTCGGCAAAGACCAGACCGTTCATACAGAA<br>CTGGCGATCGTTCGGCGTATCGCCAAAATCACCGC<br>CGTAAGCCGACCACGGGTTGCCGTTTTCATCATAT<br>TTAATCAGCGACTGATCCACCCAGTCCCAGACGAA<br>GCCGCCCTGTAAACGGGGATACTGACGAAACGCCT<br>GCCAGTATTTAGCGAAACCGCCAAGACTGTTACCC<br>ATCGCGTGGGCGTATTCGCAAAGGATCAGCGGGCG<br>CGTCTCTCCAGGTAGCGAAAGCCATTTTTTTGATGG<br>ACCATTTCGGCACAGCCGGGAAGGGCTGGTCTTCA<br>TCCACGCGCGCGTACATCGGGCAAATAATATCGGT<br>GGCCGTGGTGTCGGCTCCGCCGCCTTCATACTGCA<br>CCGGGCGGGAAGGATCGACAGATTTGATCCAGCGA<br>TACAGCGCGTCGTGATTAGCGCCGTGGCCTGATTC<br>ATTCCCCAGCGACCAGATGATCACACTCGGGTGAT<br>TACGATCGCGCTGCACCATTCGCGTTACGCGTTCG<br>CTCATCGCCGGTAGCCAGCGCGGATCATCGGTCAG<br>ACGATTCATTGGCACCATGCCGTGGGTTTCAATAT<br>TGGCTTCATCCACCCATACAGGCCGTAGCGGTCG<br>CACAGCGTGTACCACAGCGGATGGTTCGGATAATG<br>CGAACAGCGCACGGCGTTAAAGTTGTTCTGCTTCA<br>TCAGCAGGATATCCTGCACCATCGTCTGCTCATCC<br>ATGACCTGACCATGCAGAGGATGATGCTCGTGACG<br>GTTAACGCCTCGAATCAGCAACGGCTTGCCGTTCA<br>GCAGCAGCAGACCATTTTCAATCCGCACCTCGCGG<br>AAACCGACATCGCAGGCTTCTGCTTCAATCAGCGT<br>GCCGTCGGCGGTGTGCAGTTCAACCACCGCACGAT<br>AGAGATTCGGGATTTCGGCGCTCCACAGTTTCGGG<br>TTTTCGACGTTCAGACGTAGTGTGACGCGATCGGC<br>ATAACCACCACGCTCATCGATAATTTCACCGCCGA<br>AAGGCGCGGTGCCGCTGGCGACCTGCGTTTCACCC<br>TGCCATAAAGAAACTGTTACCCGTAGGTAGTCACG<br>CAACTCGCCGCACATCTGAACTTCAGCCTCCAGTA<br>CAGCGCGGCTGAAATCATCATTAAAGCGAGTGGCA<br>ACATGGAAATCGCTGATTTGTGTAGTCGGTTTATG<br>CAGCAACGAGACGTCACGGAAAATGCCGCTCATCC<br>GCCACATATCCTGATCTTCCAGATAACTGCCGTCA<br>CTCCAGCGCAGCACCATCACCGCGAGGCGGTTTTC<br>TCCGGCGCGTAAAAATGCGCTCAGGTCAAATTCAG | |
| alphaBR-gb left | 696 | ATTCGAGCTGCATGCCTGCAGGCTCTTCGAGTATC<br>AGAAGAGTGGCTTAACTATGCGGCATCAGAGCTTA<br>TTTTTGACACCAGACCAACTGGTAATGGTAGCGAC<br>CGGCGCTCAGCTGGAATTCCGCCGATACTGACGGG<br>CTCCAGGAGTCGTCGCCACCAATCCCCATATGGAA<br>ACCGTCGATATTCAGCCATGTGCCTTCTTCCGCGT<br>GCAGCAGATGGCGATGGCTGGTTTCCATCAGTTGC<br>TGTTGACTGTAGCGGCTGATGTTGAACTGGAAGTC<br>GCCGCGCCACTGGTGTGGGCCATAATTCAATTCGC<br>GCGTCCCGCAGCGCAGACCGTTTTCGCTCGGGAAG<br>ACGTACGGGGTATACATGTCTGACAATGGCAGATC<br>CCAGCGGTCAAAACAGGCGGCAGTAAGGCGGTCGG<br>GATAGTTTTCTTGCGGCCCTAATCCGAGCCAGTTT<br>ACCCGCTCTGCTACCTGCGCCAGCTGGCAGTTCAG<br>GCCAATCCGCGCCGGATGCGGTGTATCGCTCGCCA<br>CTTCAACATCAACGGTAATCGCCATTTGACCACTA<br>CCATCAATCCGGTAGGTTTTCCGGCTGATAAATAA<br>GGTTTTCCCCTGATGCTGCCACGCGTGAGCGGTCG<br>TAATCAGCACCGCATCAGCAAGTGTATCTGCCGTG<br>CACTGCAACAACGCTGCTTCGGCCTGGTAAT | SEQ ID NO: 263 |
| alphaBR-gb right | 718 | AATGCGCTCAGGTCAAATTCAGACGGCAAACGACT<br>GTCCTGGCCGTAACCGACCCAGCGCCCGTTGCACC<br>ACAGATGAAACGCCGAGTTAACGCCATCAAAAATA<br>ATTCGCGTCTGGCCTTCCTGTAGCCAGCTTTCATC<br>AACATTAAATGTGAGCGAGTAACAACCCGTCGGAT<br>TCTCCGTGGGAACAAACGGCGGATTGACCGTAATG<br>GGATAGGTCACGTTGGTGTAGATGGGCGCATCGTA<br>ACCGTGCATCTGCCAGTTTGAGGGGACGACGACAG<br>TATCGGCCTCAGGAAGATCGCACTCCAGCCAGCTT<br>TCCGGCACCGCTTCTGGTGCCGGAAACCAGGCAAA<br>GCGCCATTCGCCATTCAGGCTGCGCAACTGTTGGG<br>AAGGGCGATCGGTGCGGGCCTCGACGGCCAGTGAA<br>TCCGTAATCATGGTCATAGCTGTTTCTGTGTGAAA<br>TTGTTATCGCTCACAATTCCACACAACATACGAG<br>CCGGAAGCATAAAGTGTAAAGCCTGGGGTGCCTAA | SEQ ID NO: 264 |

TABLE II-continued

| Name | Length | Sequence | SEQ ID NO: |
|---|---|---|---|
| | | TGAGTGAGCTAACTCACATTAATTGCGTTGCGCTC<br>ACTGCCCGCTTTCCAGTCGGGAAACCTGTCGTGCC<br>AGCTGCATTAATGAATCGGCCAACGCGCGGGGAGA<br>GGCGGTTTGCGTATACTCTTCAGGTAATCGAAGAG<br>CTGGATCAGATTGTCGTTTCCCGCCTTCAGTTTAA<br>ACTATCAGTGTTTGACAG | |
| alphaCR-gb left | 696 | ATTCGAGCTGCATGCCTGCAGGCTCTTCGAATATC<br>AGAAGAGTGGCTTAACTATGCGGCATCAGAGCTTA<br>TTTTTGACACCAGACCAACTGGTAATGGTAGCGAC<br>CGGCGCTCAGCTGGAATTCCGCCGATACTGACGGG<br>CTCCAGGAGTCGTCGCCACCAATCCCCATATGGAA<br>ACCGTCGATATTCAGCCATGTGCCTTCTTCCGCGT<br>GCAGCAGATGGCGATGGCTGGTTTCCATCAGTTGC<br>TGTTGACTGTAGCGGCTGATGTTGAACTGGAAGTC<br>GCCGCGCCACTGGTGTGGGCCATAATTCAATTCGC<br>GCGTCCCGCAGCGCAGACCGTTTTCGCTCGGGAAG<br>ACGTACGGGGTATACATGTCTGACAATGGCAGATC<br>CCAGCGGTCAAAACAGGCGGCAGTAAGGCGGTCGG<br>GATAGTTTTCTTGCGGCCCTAATCCGAGCCAGTTT<br>ACCCGCTCTGCTACCTGCGCCAGCTGGCAGTTCAG<br>GCCAATCCGCGCCGGATGCGGTGTATCGCTCGCCA<br>CTTCAACATCAACGGTAATCGCCATTTGACCACTA<br>CCATCAATCCGGTAGGTTTTCCGGCTGATAAATAA<br>GGTTTTCCCCTGATGCTGCCACGCGTGAGCGGTCG<br>TAATCAGCACCGCATCAGCAAGTGTATCTGCCGTG<br>CACTGCAACAACGCTGCTTCGGCCTGGTAAT | SEQ ID NO: 265 |
| alphaCR-gb right | 718 | AATGCGCTCAGGTCAAATTCAGACGGCAAACGACT<br>GTCCTGGCCGTAACCGACCCAGCGCCCGTTGCACC<br>ACAGATGAAACGCCGAGTTAACGCCATCAAAAATA<br>ATTCGCGTCTGGCCTTCCTGTAGCCAGCTTTCATC<br>AACATTAAATGTGAGCGAGTAACAACCCGTCGGAT<br>TCTCCGTGGGAACAAACGGCGGATTGACCGTAATG<br>GGATAGGTCACGTTGGTGTAGATGGGCGCATCGTA<br>ACCGTGCATCTGCCAGTTTGAGGGGACGACGACAG<br>TATCGGCCTCAGGAAGATCGCACTCCAGCCAGCTT<br>TCCGGCACCGCTTCTGGTGCCGGAAACCAGGCAAA<br>GCGCCATTCGCCATTCAGGCTGCGCAACTGTTGGG<br>AAGGGCGATCGGTGCGGGCCTCGACGGCCAGTGAA<br>TCCGTAATCATGGTCATAGCTGTTTCTGTGTGAAA<br>TTGTTATCCGCTCACAATTCCACACAACATACGAG<br>CCGGAAGCATAAAGTGTAAAGCCTGGGGTGCCTAA<br>TGAGTGAGCTAACTCACATTAATTGCGTTGCGCTC<br>ACTGCCCGCTTTCCAGTCGGGAAACCTGTCGTGCC<br>AGCTGCATTAATGAATCGGCCAACGCGCGGGGAGA<br>GGCGGTTTGCGTATACTCTTCAGGTGATCGAAGAG<br>CTGGATCAGATTGTCGTTTCCCGCCTTCAGTTTAA<br>ACTATCAGTGTTTGACAG | SEQ ID NO: 266 |
| omegaBR-gb left | 697 | ATTCGAGCTGCATGCCTGCAGCCCTCTTCAAGTAT<br>CCGAAGAGCGGCTTAACTATGCGGCATCAGAGCTT<br>ATTTTTGACACCAGACCAACTGGTAATGGTAGCGA<br>CCGGCGCTCAGCTGGAATTCCGCCGATACTGACGG<br>GCTCCAGGAGTCGTCGCCACCAATCCCCATATGGA<br>AACCGTCGATATTCAGCCATGTGCCTTCTTCCGCG<br>TGCAGCAGATGGCGATGGCTGGTTTCCATCAGTTG<br>CTGTTGACTGTAGCGGCTGATGTTGAACTGGAAGT<br>CGCCGCGCCACTGGTGTGGGCCATAATTCAATTCG<br>CGCGTCCCGCAGCGCAGACCGTTTTCGCTCGGGAA<br>GACGTACGGGGTATACATGTCTGACAATGGCAGAT<br>CCCAGCGGTCAAAACAGGCGGCAGTAAGGCGGTCG<br>GGATAGTTTTCTTGCGGCCCTAATCCGAGCCAGTT<br>TACCCGCTCTGCTACCTGCGCCAGCTGGCAGTTCA<br>GGCCAATCCGCGCCGGATGCGGTGTATCGCTCGCC<br>ACTTCAACATCAACGGTAATCGCCATTTGACCACT<br>ACCATCAATCCGGTAGGTTTTCCGGCTGATAAATA<br>AGGTTTTCCCCTGATGCTGCCACGCGTGAGCGGTC<br>GTAATCAGCACCGCATCAGCAAGTGTATCTGCCGT<br>GCACTGCAACAACGCTGCTTCGGCCTGGTAAT | SEQ ID NO: 267 |
| omegaBR-gb right | 718 | AATGCGCTCAGGTCAAATTCAGACGGCAAACGACT<br>GTCCTGGCCGTAACCGACCAGCGCCCGTTGCACCA<br>CAGATGAAACGCCGAGTTAACGCCATCAAAAATAA<br>TTCGCGTCTGGCCTTCCTGTAGCCAGCTTTCATCA<br>ACATTAAATGTGAGCGAGTAACAACCCGTCGGATT<br>CTCCGTGGGAACAAACGGCGGATTGACCGTAATGG<br>GATAGGTCACGTTGGTGTAGATGGGCGCATCGTAA<br>CCGTGCATCTGCCAGTTTGAGGGGACGACGACAGT<br>ATCGGCCTCAGGAAGATCGCACTCCAGCCAGCTTT<br>CCGGCACCGCTTCTGGTGCCGGAAACCAGGCAAAG<br>CGCCATTCGCCATTCAGGCTGCGCAACTGTTGGGA | SEQ ID NO: 268 |

TABLE II-continued

| Name | Length | Sequence | SEQ ID NO: |
|---|---|---|---|
| | | AGGGCGATCGGTGCGGGCCTCGACGGCCAGTGAAT<br>CCGTAATCATGGTCATAGCTGTTTCTGTGTGAAAT<br>TGTTATCCGCTCACAATTCCACACAACATACGAGC<br>CGGAAGCATAAAGTGTAAAGCCTGGGGTGCCTAAT<br>GAGTGAGCTAACTCACATTAATTGCGTTGCGCTCA<br>CTGCCCGCTTTCCAGTCGGGAAACCTGTCGTGCCA<br>GCTGCATTAATGAATCGGCCAACGCGCGGGGAGAG<br>GCGGTTTGCGTATGCTCTTCGGGTAATAGAAGAGG<br>GGGATCAGATTGTCGTTTCCCGCCTTCAGTTTAAA<br>CTATCAGTGTTTGACAG | |
| omegaCR-gb left | 697 | ATTCGAGCTGCATGCCTGCAGCCCTCTTCAAATAT<br>CCGAAGAGCGGCTTAACTATGCGGCATCAGAGCTT<br>ATTTTTGACACCAGACCAACTGGTAATGGTAGCGA<br>CCGGCGCTCAGCTGGAATTCCGCCGATACTGACGG<br>GCTCCAGGAGTCGTCGCCACCAATCCCCATATGGA<br>AACCGTCGATATTCAGCCATGTGCCTTCTTTCCGC<br>GTGCAGCAGATGGCGATGGCTGGTTTCCATCAGTT<br>GCTGTTGACTGTAGCGGCTGATGTTGAACTGGAAG<br>TCGCCGCGCCACTGGTGTGGGCCATAATTCAATTC<br>GCGCGTCCCGCAGCGCAGACCGTTTTCGCTCGGGA<br>GACGTACGGGTATACATGTCTGACAATGGCAGATC<br>CCAGCGGTCAAAACAGGCGGCAGTAAGGCGGTCGG<br>GATAGTTTTCTTGCGGCCCTAATCCGAGCCAGTTT<br>ACCCGCTCTGCTACCTGCGCCAGCTGGCAGTTCAG<br>GCCAATCCGCGCCGGATGCGGTGTATCGCTCGCCA<br>CTTCAACATCAACGGTAATCGCCATTTGACCACTA<br>CCATCAATCCGGTAGGTTTTCCGGCTGATAAATAA<br>GGTTTTCCCCTGATGCTGCCACGCGTGAGCGGTCG<br>TAATCAGCACCGCATCAGCAAGTGTATCTGCCGTG<br>CACTGCAACAACGCTGCTTCGGCCTGGTAAG | SEQ ID NO: 269 |
| omegaCR-gb right | 718 | AATGCGCTCAGGTCAAATTCAGACGGCAAACGACT<br>GTCCTGGCCGTAACCGACCCAGCGCCCGTTGCACC<br>ACAGATGAAACGCCGAGTTAACGCCATCAAAAATA<br>ATTCGCGTCTGGCCTTCCTGTAGCCAGCTTTCATC<br>AACATTAAATGTGAGCGAGTAACAACCCGTCGGAT<br>TCTCCGTGGGAACAAACGGCGGATTGACCGTAATG<br>GGATAGGTCACGTTGGTGTAGATGGGCGCATCGTA<br>ACCGTGCATCTGCCAGTTTGAGGGGACGACGACAG<br>TATCGGCCTCAGGAAGATCGCACTCCAGCCAGCTT<br>TCCGGCACCGCTTCTGGTGCCGGAAACCAGGCAAA<br>GCGCCATTCGCCATTCAGGCTGCGCAACTGTTGGG<br>AAGGGCGATCGGTGCGGGCCTCGACGGCCAGTGAA<br>TCCGTAATCATGGTCATAGCTGTTTCTGTGTGAAA<br>TTGTTATCCGCTCACAATTCCACACAACATACGAG<br>CCGGAAGCATAAAGTGTAAAGCCTGGGGTGCCTAA<br>TGAGTGAGCTAACTCACATTAATTGCGTTGCGCTC<br>ACTGCCCGCTTTCCAGTCGGGAAACCTGTCGTGCC<br>AGCTGCATTAATGAATCGGCCAACGCGCGGGGAGA<br>GGCGGTTTGCGTATGCTCTTCGGGTGATAGAAGAG<br>GGGGATCAGATTGTCGTTTCCCGCCTTCAGTTTAA<br>ACTATCAGTGTTTGACAG | SEQ ID NO: 270 |
| RGR gene | 247 | ACATGCAGCTCTTCCaccGGGTTACTGATGAGTCC<br>GTGAGGACGAAACGAGTAAGCTCGTCTAACCCAAG<br>GGGTGACAAGCGTTTTAGAGCTAGAAATAGCAAGT<br>TAAAATAAGGCTAGTCCGTTATCAACTTGAAAAAG<br>TGGCACCGAGTCGGTGCTTTTGGCCGGCATGGTCC<br>CAGCCTCCTCGCTGGCGCCGGCTGGGCAACATGCT<br>TCGGCATGGCGAATGGGACgatGGAAGAGCTTCCT<br>CG | SEQ ID NO: 271 |
| GeneSynthesis | | | |
| M.SacI cluster | 1924 | TCAGATCCCGGGTCAATAGCATTCTCACCAATAAA<br>AAACGCCCGGCGGCAACCGAGCGTTCTGAACAAAT<br>CCAGATGGAGTTCTGAGGTCATTACTGGATCTATC<br>AACAGGAGTCCAAGCGGCCGCTTTTTTTACCTCCT<br>AAAAGTTAAACAAAATTATTTCTAGAGGGAAACCG<br>TTGTGGAATTGTGAGCGCTCACAATTCCACATATT<br>ATAATTGTTATCCGCTCACAAAGCAAATAAATTTT<br>TCATGATTTCACTGTGCATGAAGCTCGTAATTGTT<br>ATCCGCTCACAATTAAACAAGCGCTCATGAGCCCG<br>AAGTGGCGAGCCCGATCTTCCCCATCGGTGATGTC<br>GGCGATATAGGCGCCAGCAACGCACCTGTGGCGC<br>CGGTGATGCCGGCCACAGATGCGTCCGGCGTAGAG<br>GATCGAGATCTCGATCCCGCGAAATTAATACGACT<br>CACTATAGGGGAATTGTGAGCGGATAACAATTCCC<br>CTCTAGAAATAATTTTGTTTAACTTTAAGAAGGAG<br>ATATACCATGGGTCTGCCTCCGCTGCTGAGCCTGC | SEQ ID NO: 272 |

TABLE II-continued

| Name | Length | Sequence | SEQ ID NO: |
|------|--------|----------|------------|
| | | CGAGCAATAGCGCACCGCGTAGCCTGGGTCGTGTT | |
| | | GAAACCCCTCCGGAAGTTGTTGATTTTATGGTTAG | |
| | | CCTGGCCGAAGCACCGCGTGGTGGTCGTGTTCTGG | |
| | | AACCGGCATGTGCCCATGGTCCGTTTCTGCGTGCA | |
| | | TTTCGTGAAGCACATGGCACCGGTTATCGTTTTGT | |
| | | TGGTGTTGAAATTGATCCGAAAGCACTGGATCTGC | |
| | | CACCGTGGGCAGAAGGTATTCTGGCAGATTTTCTG | |
| | | CTGTGGGAACCGGGTGAAGCATTTGATCTGATTCT | |
| | | GGGTAATCCGCCTTATGGTATTGTTGGTGAAGCAA | |
| | | GCAAATATCCGATCCATGTTTTTAAAGCCGTGAAA | |
| | | GATCTGTACAAAAAAGCCTTTAGCACCTGGAAAGG | |
| | | CAAATATAACCTGTATGGTGCCTTTCTGGAAAAAG | |
| | | CAGTTCGTCTGCTGAAACCGGGTGGTGTTCTGGTT | |
| | | TTTGTTGTTCCGGCAACCTGGCTGGTGCTGGAAGA | |
| | | TTTTGCACTGCTGCGTGAATTTCTGGCACGTGAAG | |
| | | GTAAAACCAGCGTTTATTATCTGGGTGAAGTTTTT | |
| | | CCGCAGAAAAAAGTTAGCGCAGTGGTTATTCGTTT | |
| | | TCAGAAAAGCGGTAAAGGTCTGAGCCTGTGGGATA | |
| | | CCCAAGAAAGCGAAAGCGGTTTTACCCCGATTCTG | |
| | | TGGGCTGAATATCCGCATTGGGAAGGTGAAATTAT | |
| | | TCGCTTTGAAACCGAAGAAACCCGCAAACTGGAAA | |
| | | TTTCAGGTATGCCGCTGGGTGACCTGTTTCATATC | |
| | | CGTTTTGCAGCACGTAGTCCGGAATTCAAAAAACA | |
| | | TCCGGCAGTTCGTAAAGAACCGGGTCCGGGTCTGG | |
| | | TTCCGGTTCTGACCGGTCGTAATCTGAAACCTGGT | |
| | | TGGGTTGATTATGAAAAAAATCATAGCGGTCTGTG | |
| | | GATGCCGAAAGAACGTGCAAAAGAACTGCGTGATT | |
| | | TTTATGCAACACCGCATCTGGTTGTTGCACATACC | |
| | | AAAGGCACCCGTGTTGTTGCAGCATGGGATGAACG | |
| | | TGCATATCCGTGGCGTGAAGAATTTCATCTGCTGC | |
| | | CTAAAGAAGGTGTTCGTCTGGATCCGAGCAGCCTG | |
| | | GTTCAGTGGCTGAATAGCGAAGCAATGCAGAAACA | |
| | | TGTTCGTACCCTGTATCGTGATTTTGTTCCGCATC | |
| | | TGACCCTGCGTATGCTGGAACGTCTGCCGGTTCGT | |
| | | CGTGAATATGGTTTTCATACCAGTCCGGAAAGCGC | |
| | | ACGTAACTTTTAACAAAGCCCGAAAGGAAGCTGAG | |
| | | TTGGCTGCTGCCACCGCTGAGCAATAACTAGCATA | |
| | | ACCCCTTGGGGCCTCTAAACGGGTCTTGAGGGGTT | |
| | | TTTTGCTGAAAGGAGGCCACTCGAGCACCTAGGAG | |

---

What is claimed is:

1. A cloning system, comprising:

I. a first family of double-stranded destination vectors comprising at least two first family destination vectors 1A and 2, wherein each of the destination vectors in the first family comprises the same first type IIS restriction enzyme site, the same second type IIS restriction enzyme site, and a selectable marker gene, wherein each destination vector comprises at least three signature elements, wherein said three signature elements are different from one another, wherein each of said three signature elements consists of 3-nucleotides, and wherein each first family destination vector comprises, from 5' to 3' in the sense strand:

a. the forward sequence of the first type IIS restriction enzyme site;
b. the forward sequence of a first signature element;
c. the reverse complement sequence of the second type IIS restriction enzyme site;
d. the selectable marker gene;
e. the forward sequence of the second type IIS restriction enzyme site;
f. the forward sequence of a second signature element; and g. the reverse complement sequence of the first type IIS restriction enzyme site;
wherein said first family destination vectors 1A and 2 are further organized as follows:
  i. said first family destination vector 1A further comprises, from 5' to 3' on the sense strand, the forward sequence of a third signature element between (f) the forward sequence of the second signature element and (g) the reverse complement sequence of the first type IIS restriction enzyme site; and
  ii. said first family destination vector 2 further comprises, from 5' to 3' on the sense strand, the forward sequence of said third signature element between (a) the forward sequence of the first type IIS restriction enzyme site and (b) the forward sequence of the first signature element;
II. a second family of double-stranded destination vectors comprising at least one second family destination vector 1A, each vector in said second family comprising the same first and second type IIS restriction enzyme sites as in the first family of destination vectors, and at least three signature elements which are the same signature elements as in the first family of destination vectors, and further comprising a selectable marker gene that can be the same or different from the selectable marker gene of said first family destination vectors, and wherein each second family destination vector comprises, from 5' to 3' in the sense strand:
  a. the forward sequence of the second type IIS restriction enzyme site;
  b. the forward sequence of the first signature element;
  c. the reverse complement sequence of the first type IIS restriction enzyme site;
  d. the selectable marker gene;
  e. the forward sequence of the first type IIS restriction enzyme site;
  f. the forward sequence of said second signature element; and
  g. the reverse complement sequence of the second type IIS restriction enzyme site;
wherein said second family destination vector 1A further comprises, from 5' to 3' on the sense strand, the forward sequence of the third signature element between (f) the forward sequence of the second signature element and (g) the reverse complement sequence of the second type IIS restriction enzyme site;
III. a destination vector B which further comprises, from 5' to 3' on the sense strand, the forward sequence of said third signature element between (a) the forward sequence of the first type IIS restriction enzyme site and (b) the forward sequence of the first signature element; and the forward sequence of a fourth signature element between (f) the forward sequence of the second signature element and (g) the reverse complement sequence of the first type IIS restriction enzyme site, wherein the fourth signature element consists of 3-nucleotides and wherein the fourth signature element is different from the first, second, and third signature elements; and
IV. a destination vector C which further comprises, from 5' to 3' on the sense strand, the forward sequence of said fourth signature element between (a) the forward sequence of the first type IIS restriction enzyme site and (b) the forward sequence of the first signature element.

2. The cloning system of claim 1, wherein said second family of destination vectors further comprises a second family destination vector 2 which further comprises, from 5' to 3' on the sense strand, the forward sequence of said third signature element between (a) the forward sequence of the second type IIS restriction enzyme site and (b) the forward sequence of the first signature element.

3. The cloning system of claim 1, wherein said second family of destination vectors further comprises the following second family destination vectors:
  V. a destination vector B which further comprises, from 5' to 3' on the sense strand, the forward sequence of said third signature element between (a) the forward sequence of the second type IIS restriction enzyme site and (b) the forward sequence of the first signature element; and the forward sequence of said fourth signature element between (f) the forward sequence of the second signature element and (g) the reverse complement sequence of the second type IIS restriction enzyme site; and
  VI. a destination vector C which further comprises, from 5' to 3' on the sense strand, the forward sequence of said fourth signature element between (a) the forward sequence of the second type IIS restriction enzyme site and (b) the forward sequence of the first signature element.

4. The cloning system of claim 1, wherein each member of said first and second families of destination vectors further comprises a second selectable marker which is the same within each family, but which differs between the first and second families.

5. The cloning system of claim 4, wherein said second selectable markers for said first and second families are antibiotic resistance genes.

6. The cloning system of claim 1, wherein the first and second type IIS restriction enzyme sites are selected from restriction enzyme recognition sites for *Enterobacter aerogenes* I (EarI), *Lysobacter gummosus* RFLI (LguI), *Bacillus coagulans* 5I (Bco5I), *Bacillus coagulans* 116I (Bco116I), *Bacillus coagulans* KI (BcoKI), *Bacillus stearothermophilus* XI (BsaXI), *Bacillus stearothermophilus* ZI (BseZI), *Bacillus stearothermophilus* 6I (Bst6I), *Bacillus stearothermophilus* IMI (BssIMI), *Bacillus sphaericus* QI (BspQI), *Bacillus stearothermophilus* IMI (BssIMI), *Bacillus subtilis* 6I (Bsu6I), *Bacillus atrophaeus* HI (BatHI), *Enterobacter amnigenus* RFL1104 (Eam1104I), *Klebsiella pneumoniae* NIH30III (KpnNIH30III), *Planococcus citreus* SI (PciSI), *Rhizobium leguminosarum* AI (RleAI), *Saccharopolyspora* species I (SapI), *Staphylococcus intermedius* I (SimI), and *Vibrio parahaemolyticus* K32I (VpaK32I).

7. The cloning system of claim 6, wherein the first and second type IIS restriction enzyme sites are selected from *Enterobacter aerogenes* I (EarI) and *Lysobacter gummosus* RFLI (LguI).

8. The cloning system of claim 1, further comprising a ligation buffer comprising a polyglycol polymer.

9. The cloning system of claim 8, wherein said ligation buffer further comprises 20-80 mM Tris-HCl, (pH 7-8); 0.1-4.0 mM dithiothreitol (DTT); 1-20 mM $MgCl_2$; 0.1-2.0 mM ATP; and 0.1-4.0% poly(propylene glycol) (PPG).

10. The cloning system of claim 1, wherein said first family of destination vectors further comprises at least one vector for antisense expression of a nucleic acid, wherein said at least one vector for antisense expression is selected from:
  VII. a first family destination vector 1A-R comprising, from 5' to 3' in the sense strand:

the forward sequence of the first type IIS restriction enzyme site, with a restriction enzyme cleavage site at the 5' end of the first signature element;

the forward sequence of said first signature element;

the reverse complement sequence of the second signature element;

the reverse complement sequence of the second type IIS restriction enzyme site, with a restriction enzyme cleavage site at the 3' end of the reverse complement sequence of said second signature element;

the selectable marker gene;

the forward sequence of the second type IIS restriction enzyme site, with a restriction enzyme cleavage site at the 5' end of the first reverse complement sequence of the first signature element;

the reverse complement sequence of the first signature element;

the forward sequence of the third signature element; and the reverse complement sequence of the first type IIS restriction enzyme site, with a restriction enzyme cleavage site at the 3' end of a fourth signature element;

VIII. a first family destination vector 2-R which comprises, from 5' to 3' in the sense strand:

the forward sequence of the first type IIS restriction enzyme site, with a restriction enzyme cleavage site at the 5' end of the third signature element;

the forward sequence of said third signature element;

the reverse complement sequence of the second signature element;

the reverse complement sequence of the second type IIS restriction enzyme site, with a restriction enzyme cleavage site at the 3' end of the reverse complement sequence of said second signature element;

the selectable marker gene;

the forward sequence of the second type IIS restriction enzyme site, with a restriction enzyme cleavage site at the 5' end of the first reverse complement sequence of the first signature element;

the reverse complement sequence of the first signature element;

the forward sequence of the second signature element; and the reverse complement sequence of the first type IIS restriction enzyme site, with a restriction enzyme cleavage site at the 3' end of the second signature element;

IX. a first family destination vector B-R which comprises, from 5' to 3' in the sense strand:

the forward sequence of the first type IIS restriction enzyme site, with a restriction enzyme cleavage site at the 5' end of the third signature element;

the forward sequence of said third signature element;

the reverse complement sequence of the second signature element;

the reverse complement sequence of the second type IIS restriction enzyme site, with a restriction enzyme cleavage site at the 3' end of the reverse complement sequence of said second signature element;

the selectable marker gene;

the forward sequence of the second type IIS restriction enzyme site, with a restriction enzyme cleavage site at the 5' end of the first reverse complement sequence of the first signature element;

the reverse complement sequence of the first signature element;

the forward sequence of the fourth signature element; and the reverse complement sequence of the first type IIS restriction enzyme site, with a restriction enzyme cleavage site at the 3' end of the fourth signature element; and X. a first family destination vector C-R which comprises, from 5' to 3' in the sense strand:

the forward sequence of the first type IIS restriction enzyme site, with a restriction enzyme cleavage site at the 5' end of the fourth signature element;

the forward sequence of said fourth signature element;

the reverse complement sequence of the second signature element;

the reverse complement sequence of the second type IIS restriction enzyme site, with a restriction enzyme cleavage site at the 3' end of the reverse complement sequence of said second signature element;

the selectable marker gene;

the forward sequence of the second type IIS restriction enzyme site, with a restriction enzyme cleavage site at the 5' end of the first reverse complement sequence of the first signature element;

the reverse complement sequence of the first signature element;

the forward sequence of the second signature element; and the reverse complement sequence of the first type IIS restriction enzyme site, with a restriction enzyme cleavage site at the 3' end of the second signature element.

* * * * *

SEQUENCE LISTING

<160> NUMBER OF SEQ ID NOS: 274

<210> SEQ ID NO 1
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 1
acatgcagct cttcc                                                      15

<210> SEQ ID NO 2
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 2
ggaagagctg catgt                                                      15

<210> SEQ ID NO 3
<211> LENGTH: 15
<212> TYPE: DNA
<213> ORGANISM: Artificial Sequence

```
<220> FEATURE:
<223> OTHER INFORMATION: Synthetic Oligonucleoide

<400> SEQUENCE: 3
ggaagagctt cctcg                                                     15

<210> SEQ ID NO 4
<211> LENGTH: 15
<212> TYPE: DNA
<213> ORGANISM: Artificial Sequence
<220> FEATURE:
<223> OTHER INFORMATION: Synthetic Oligonucleoide

<400> SEQUENCE: 4
cgaggaagct cttcc                                                     15

<210> SEQ ID NO 5
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 5
caggctcttc gaccagaaga gtgg                                           24

<210> SEQ ID NO 6
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 6
tatgctcttc ggatagtaga agagggg                                        27

<210> SEQ ID NO 7
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 7
gctcttccac cccggg                                                    16

<210> SEQ ID NO 8
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 8
cccggggtgg aagagc                                                    16

<210> SEQ ID NO 9
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 9
cccgggatgg aagagc                                                    16
```

```
<210> SEQ ID NO 10
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 10
gctcttccat cccggg                                                    16

<210> SEQ ID NO 11
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 11
gctcttcgac cagaagagt                                                 19

<210> SEQ ID NO 12
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 12
actcttctgg tcgaagagc                                                 19

<210> SEQ ID NO 13
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 13
actcttcaga tagtcgaaga gc                                             22

<210> SEQ ID NO 14
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 14
gctcttcgac tatctgaaga gt                                             22

<210> SEQ ID NO 15
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 15
gctcttcgag taccagaaga gt                                             22

<210> SEQ ID NO 16
<211> LENGTH: 22
<212> TYPE: DNA
<213> ORGANISM: Artificial Sequence
<220> FEATURE:
<223> OTHER INFORMATION: Synthetic Oligonucleotide
```

```
<400> SEQUENCE: 16
actcttctgg tactcgaaga gc                                              22

<210> SEQ ID NO 17
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 17
actcttcaga tcgaagagc                                                  19

<210> SEQ ID NO 18
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 18
gctcttcgat ctgaagagt                                                  19

<210> SEQ ID NO 19
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 19
gctcttcgag taccagaaga gt                                              22

<210> SEQ ID NO 20
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 20
actcttctgg tactcgaaga gc                                              22

<210> SEQ ID NO 21
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 21
actcttcaga taatcgaaga gc                                              22

<210> SEQ ID NO 22
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 22
gctcttcgat tatctgaaga gt                                              22

<210> SEQ ID NO 23
<211> LENGTH: 22
```

```
<212> TYPE: DNA
<213> ORGANISM: Artificial Sequence
<220> FEATURE:
<223> OTHER INFORMATION: Synthetic Oligonucleotide

<400> SEQUENCE: 23
gctcttcgaa taccagaaga gt                                        22

<210> SEQ ID NO 24
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 24
actcttctgg tattcgaaga gc                                        22

<210> SEQ ID NO 25
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 25
actcttcaga tcgaagagc                                            19

<210> SEQ ID NO 26
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 26
gctcttcgat ctgaagagt                                            19

<210> SEQ ID NO 27
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 27
cctcttcaac ccgaagagc                                            19

<210> SEQ ID NO 28
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 28
gctcttcggg ttgaagagg                                            19

<210> SEQ ID NO 29
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 29
```

```
gctcttcgga tagtagaaga gg                                              22

<210> SEQ ID NO 30
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 30
cctcttctac tactccgaag agc                                             23

<210> SEQ ID NO 31
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 31
cctcttcaag tacccgaaga gc                                              22

<210> SEQ ID NO 32
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 32
gctcttcggg tacttgaaga gg                                              22

<210> SEQ ID NO 33
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 33
gctcttcgga tagaagagg                                                  19

<210> SEQ ID NO 34
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 34
cctcttctat ccgaagagc                                                  19

<210> SEQ ID NO 35
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 35
cctcttcaag tacccgaaga gc                                              22

<210> SEQ ID NO 36
<211> LENGTH: 22
<212> TYPE: DNA
<213> ORGANISM: Artificial Sequence
```

```
<220> FEATURE:
<223> OTHER INFORMATION: Synthetic Oligonuclotide

<400> SEQUENCE: 36
gctcttcggg tacttgaaga gg                                              22

<210> SEQ ID NO 37
<211> LENGTH: 22
<212> TYPE: DNA
<213> ORGANISM: Artificial Sequence
<220> FEATURE:
<223> OTHER INFORMATION: Synthetic Oligonuclotide

<400> SEQUENCE: 37
gctcttcgga taatagaaga gg                                              22

<210> SEQ ID NO 38
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 38
cctcttctat tatccgaaga gc                                              22

<210> SEQ ID NO 39
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 39
cctcttcaaa tacccgaaga gc                                              22

<210> SEQ ID NO 40
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 40
gctcttcggg tatttgaaga gg                                              22

<210> SEQ ID NO 41
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 41
gctcttcgga tagaagagg                                                  19

<210> SEQ ID NO 42
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 42
cctcttctat ccgaagagc                                                  19
```

```
<210> SEQ ID NO 43
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 43
gctcttcgac catcagaaga gt                                        22

<210> SEQ ID NO 44
<211> LENGTH: 22
<212> TYPE: DNA
<213> ORGANISM: Artificial Sequence
<220> FEATURE:
<223> OTHER INFORMATION: Synthetic Ologionucleotide

<400> SEQUENCE: 44
actcttctga tggtcgaaga gc                                        22

<210> SEQ ID NO 45
<211> LENGTH: 22
<212> TYPE: DNA
<213> ORGANISM: Artificial Sequence
<220> FEATURE:
<223> OTHER INFORMATION: Synthetic Ologionucleotide

<400> SEQUENCE: 45
actcttcagg tagtcgaaga gc                                        22

<210> SEQ ID NO 46
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 46
gctcttcgac tacctgaaga gt                                        22

<210> SEQ ID NO 47
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 47
gctcttcgag tatcagaaga gt                                        22

<210> SEQ ID NO 48
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 48
actcttctga tactcgaaga gc                                        22

<210> SEQ ID NO 49
<211> LENGTH: 22
<212> TYPE: DNA
<213> ORGANISM: Artificial Sequence
<220> FEATURE:
<223> OTHER INFORMATION: Synthetic Oligonucleotide
```

<400> SEQUENCE: 49
actcttcagg tgatcgaaga gc                                              22

<210> SEQ ID NO 50
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 50
gctcttcgat cacctgaaga gt                                              22

<210> SEQ ID NO 51
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 51
gctcttcgag tatcagaaga gt                                              22

<210> SEQ ID NO 52
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 52
catcttctga tactcgaaga gc                                              22

<210> SEQ ID NO 53
<211> LENGTH: 22
<212> TYPE: DNA
<213> ORGANISM: Artificial Sequence
<220> FEATURE:
<223> OTHER INFORMATION: Synthetic Oligonuclotide

<400> SEQUENCE: 53
actcttcagg taatcgaaga gc                                              22

<210> SEQ ID NO 54
<211> LENGTH: 22
<212> TYPE: DNA
<213> ORGANISM: Artificial Sequence
<220> FEATURE:
<223> OTHER INFORMATION: Synthetic Oligonuclotide

<400> SEQUENCE: 54
gctcttcgat tacctgaaga gt                                              22

<210> SEQ ID NO 55
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 55
gctcttcgaa tatcagaaga gt                                              22

<210> SEQ ID NO 56

```
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 56
actcttctga tattcgaaga gc                                              22

<210> SEQ ID NO 57
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 57
actcttcagg taatcgaaga gc                                              22

<210> SEQ ID NO 58
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 58
gctcttcgat cacctgaaga gt                                              22

<210> SEQ ID NO 59
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 59
cctcttcaac catccgaaga gc                                              22

<210> SEQ ID NO 60
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 60
gctcttcgga tggttgaaga gg                                              22

<210> SEQ ID NO 61
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 61
gctcttcggg tagtagaaga gg                                              22

<210> SEQ ID NO 62
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 62
```
cctcttctac tacccgaaga gc            22

<210> SEQ ID NO 63
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 63
cctcttcaag tatccgaaga gc            22

<210> SEQ ID NO 64
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 64
gctcttcgga tacttgaaga gg            22

<210> SEQ ID NO 65
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 65
gctcttcggg tgatagaaga gg            22

<210> SEQ ID NO 66
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 66
cctcttctat cacccgaaga gc            22

<210> SEQ ID NO 67
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 67
cctcttcaag tatccgaaga gc            22

<210> SEQ ID NO 68
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 68
gctcttcgga tacctgaaga gg            22

<210> SEQ ID NO 69
<211> LENGTH: 22
<212> TYPE: DNA

<213> ORGANISM: Artificial Sequence
<220> FEATURE:
<223> OTHER INFORMATION: Synthetic Oligonucleotide

<400> SEQUENCE: 69
gctcttcggg taatagaaga gg                                    22

<210> SEQ ID NO 70
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 70
cctcttctat tacccgaaga gc                                    22

<210> SEQ ID NO 71
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 71
cctcttcaaa tatccgaaga gc                                    22

<210> SEQ ID NO 72
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 72
gctcttcgga tatttgaaga gg                                    22

<210> SEQ ID NO 73
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 73
gctcttcggg tgatagaaga gg                                    22

<210> SEQ ID NO 74
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 74
cctcttctat cacccgaaga gc                                    22

<210> SEQ ID NO 75
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 75
gctcttccac c                                                11

<210> SEQ ID NO 76
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 76
ggtggaagag c    11

<210> SEQ ID NO 77
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 77
gatggaagag c    11

<210> SEQ ID NO 78
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 78
gctcttccat c    11

<210> SEQ ID NO 79
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 79
accagaagag    10

<210> SEQ ID NO 80
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 80
ctcttctggt    10

<210> SEQ ID NO 81
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 81
ctcttcagat agt    13

<210> SEQ ID NO 82
<211> LENGTH: 13
<212> TYPE: DNA
<213> ORGANISM: Artificial Sequence
<220> FEATURE:

<223> OTHER INFORMATION: Synthetic Oligonucleotide

<400> SEQUENCE: 82
actatctgaa gag                                                          13

<210> SEQ ID NO 83
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 83
accagaagag c                                                            11

<210> SEQ ID NO 84
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 84
gctcttctgg t                                                            11

<210> SEQ ID NO 85
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 85
gctcttcaga tagt                                                         14

<210> SEQ ID NO 86
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 86
actatctgaa gagc                                                         14

<210> SEQ ID NO 87
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 87
cactgccagt tgctcttcat atagca                                            26

<210> SEQ ID NO 88
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 88
cactgccagt tcctcttcat atagca                                            26

```
<210> SEQ ID NO 89
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 89
cactatgagt tgctcttcat atagca                                              26

<210> SEQ ID NO 90
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 90
cactggctgc cgctcttcat atagca                                              26

<210> SEQ ID NO 91
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 91
gccagttgct cttc                                                           14

<210> SEQ ID NO 92
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 92
gattgccagt tactcttctg ggacct                                              26

<210> SEQ ID NO 93
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 93
gattgccaga ctctcttctg ggacct                                              26

<210> SEQ ID NO 94
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 94
gattggctgc cactcttctg ggacct                                              26

<210> SEQ ID NO 95
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
```

```
<221> NAME/KEY: misc_feature
<222> LOCATION: (23)..(26)
<223> OTHER INFORMATION: n is a, c, g, or t

<400> SEQUENCE: 95
tgacacatgc agctcttcca ccnnnn                                          26

<210> SEQ ID NO 96
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (23)..(26)
<223> OTHER INFORMATION: n is a, c, g, or t

<400> SEQUENCE: 96
tgagcgagga agctcttcca tcnnnn                                          26

<210> SEQ ID NO 97
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (26)..(26)
<223> OTHER INFORMATION: n is a, c, g, or t

<400> SEQUENCE: 97
catgcctgca ggctcttcga vyaycn                                          26

<210> SEQ ID NO 98
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (26)..(26)
<223> OTHER INFORMATION: n is a, c, g, or t

<400> SEQUENCE: 98
aatctgatcc agctcttcga yyaycn                                          26

<210> SEQ ID NO 99
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (23)..(26)
<223> OTHER INFORMATION: n is a, c, g, or t

<400> SEQUENCE: 99
catgcctgca gactcttcaa ccnnnn                                          26

<210> SEQ ID NO 100
<211> LENGTH: 26
<212> TYPE: DNA
<213> ORGANISM: Artificial Sequence
<220> FEATURE:
<223> OTHER INFORMATION: Synthetic Oligonucleotide
```

```
<220> FEATURE:
<221> NAME/KEY: misc_feature
<222> LOCATION: (26)..(26)
<223> OTHER INFORMATION: n is a, c, g, or t

<400> SEQUENCE: 100
atgcctgcag mcctcttcaa vyaycn                                          26

<210> SEQ ID NO 101
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (26)..(26)
<223> OTHER INFORMATION: n is a, c, g, or t

<400> SEQUENCE: 101
aatctgatcc mmctcttcta yyaycn                                          26

<210> SEQ ID NO 102
<211> LENGTH: 1800
<212> TYPE: DNA
<213> ORGANISM: Artificial Sequence
<220> FEATURE:
<223> OTHER INFORMATION: Synthetic Oligonucleotide

<400> SEQUENCE: 102
gatcccgggt caatagcatt ctcaccaata aaaacgccc ggcggcaacc gagcgttctg      60
aacaaatcca gatggagttc tgaggtcatt actgtcaaca ggagtccaag cggccgcttt    120
ttttacctcc taaagttaa acaaaattat ttctagaggg aaaccgttgt ggaattgtga     180
gcgctcacca tattataatt gttatccgct cacaaagcaa ataaattttt catgatttca    240
ctgtgcatga agctcgtaat tgttatccgc tcacaattaa actcatgagc cgaagtggc    300 gagcccgatc ttccccatcg gtgatgtcgg cgatataggc gccagcaacc gcacctgtgg    360
cgccggtgat gccggtgcgt ccggcgtaga ggatcgagat ctcgatcccg cgaaataata    420
cgactcacta tagggaatt gtgagcggat aacaattccc ctctagaatt gtttaacttt    480
aagaaggaga tatacctggg tctgcctccg ctgctgagcc tgccgagcaa tagcgcaccg    540
cgtagcctgg gtcgtgttga accggaagtt gttgatttta tggttagcct ggccgaagca    600
ccgcgtggtg gtcgtgttct ggaaccggca tgtgcccatg gtccgtttct gcgtggtgaa    660
gcacatggca ccggttatcg ttttgttggt gttgaaattg atccgaaagc actggatctg    720
ccaccgtggg cagaaggtat tctggcagag ctgtgggaac cgggtgaagc atttgatctg    780
attctgggta atccgcctta tggtattgtt ggtgaagcaa gcaaatatcc gatccatgtt    840
tttgtgaaag atctgtacaa aaaagccttt agcacctgga aaggcaaata taacctgtat    900
ggtgcctttc tggaaaaagc agttcgtctg ctgaaacgtg ttctggtttt tgttgttccg    960
gcaacctggc tggtgctgga agattttgca ctgctgcgtg aatttctggc acgtgaaggt   1020
aaaaccagcg ttctgggtga agttttttccg cagaaaaaag ttagcgcagt ggttattcgt   1080
tttcagaaaa gcggtaaagg tctgagcctg tgggataccc aagaagcggt tttacccga    1140 ttctgtgggc tgaatatccg cattgggaag gtgaaattat tcgctttgaa accgaagaaa   1200
cccgcaaact ggaatttttg ccgctggggt acctgtttca tatccgtttt gcagcacgta   1260
gtccggaatt caaaaaacat ccggcagttc gtaaagaacc gggtccgggt ctggttctga   1320
```

| | | |
|---|---|---|
| ccggtcgtaa tctgaaacct ggttgggttg attatgaaaa aaatcatagc ggtctgtgga | | 1380 |
| tgccgaaaga acgtgcaaaa gaactgtttt atgcaacacc gcatctggtt gttgcacata | | 1440 |
| ccaaaggcac ccgtgttgtt gcagcatggg atgaacgtgc atatccgtgg cgtgaagaat | | 1500 |
| tgctgcctaa agaaggtgtt cgtctggatc cgagcagcct ggttcagtgg ctgaatagcg | | 1560 |
| aagcaatgca gaaacatgtt cgtaccctgt atcgtgttcc gcatctgacc ctgcgtatgc | | 1620 |
| tggaacgtct gccggttcgt cgtgaatatg gttttcatac cagtccggaa agcgcacgta | | 1680 |
| acttttaacc gaaaggaagc tgagttggct gctgccaccg ctgagcaata actagcataa | | 1740 |
| ccccttgggg cctctaaacg ggtcttgagg ggttttttgg gccactcgag cacctaggag | | 1800 |

<210> SEQ ID NO 103
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 103
gctcttccac cccggggctg gcttaactat gc                                    32

<210> SEQ ID NO 104
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 104
tggcgtaata gcgaggaggc ccgcacc                                          27

<210> SEQ ID NO 105
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 105
ggtgcgggcc tcctcgctat tacgcca                                          27

<210> SEQ ID NO 106
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 106
ctctagagga tcccctggta ccgagctcga a                                     31

<210> SEQ ID NO 107
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 107
ttcgagctcg gtaccagggg atcctctaga g                                     31

<210> SEQ ID NO 108
<211> LENGTH: 35

<210> SEQ ID NO 109
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 108
gctcttccat cccgggcgcc caatacgcaa accgc                                35

<210> SEQ ID NO 109
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 109
cccgggatgg aagagcttcc tcgctcactg actc                                34

<210> SEQ ID NO 110
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 110
gcttcaataa tattgaaaaa ggaggagtat gagtattcaa c                         41

<210> SEQ ID NO 111
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 111
gttgaatact catactcctc cttttcaat attattgaag c                          41

<210> SEQ ID NO 112
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 112
gccccggggt ggaagagctg catgtgtcag agg                                 33

<210> SEQ ID NO 113
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 113
cagctatgac catgattacg gattcac                                        27

<210> SEQ ID NO 114
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 114

```
ctcttccacc ccggggctgg cttaactatg cggcatcaga gcttattttt gacaccagac        60
caactgg                                                                 67
```

<210> SEQ ID NO 115
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 115

```
cgtaatcatg gtcatagctg tttcctgtgt g                                      31
```

<210> SEQ ID NO 116
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 116

```
gccccggggt ggaagagctg catgtgtcag agg                                    33
```

<210> SEQ ID NO 117
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 117

```
cattacagct tacgaaccga acgagg                                            26
```

<210> SEQ ID NO 118
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 118

```
gcagcgagtc agtgagcgag g                                                 21
```

<210> SEQ ID NO 119
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 119

```
ggaatttatg ccgcttccga ccatc                                             25
```

<210> SEQ ID NO 120
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 120

```
cctcgctcac tgactcgctg c                                                 21
```

<210> SEQ ID NO 121
<211> LENGTH: 37

-continued

```
<212> TYPE: DNA
<213> ORGANISM: Artificial Sequence
<220> FEATURE:
<223> OTHER INFORMATION: Synthetic Oligonucleotide

<400> SEQUENCE: 121
tcggttcgta agctgtaatg ttcctggcag ctctggc                              37

<210> SEQ ID NO 122
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 122
gatggtcgga agcggcataa attcc                                          25

<210> SEQ ID NO 123
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 123
tggatcagat tgtcgtttcc cgcc                                           24

<210> SEQ ID NO 124
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 124
ctgcaggcat gcagctcgaa ttat                                           24

<210> SEQ ID NO 125
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 125
gctcgaatta tcgatcatga gcggaga                                        27

<210> SEQ ID NO 126
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 126
gtttcccgcc ttcagtttaa actatcagtg                                     30

<210> SEQ ID NO 127
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 127
```
gctgcatgcc tgcaggctct tcga                                          24

<210> SEQ ID NO 128
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 128
gggaaacgac aatctgatcc agctcttcga                                    30

<210> SEQ ID NO 129
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 129
gcaggctctt cgaccagaag agtggcttaa ctatgcggca tcagagc                 47

<210> SEQ ID NO 130
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 130
gatccagctc ttcgactatc tgaagagtat acgcaaaccg cctctccc                48

<210> SEQ ID NO 131
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 131
gcaggctctt cgagtaccag aagagtggct taactatgcg gcatcagagc              50

<210> SEQ ID NO 132
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 132
gatccagctc ttcgatctga agagtatacg caaaccgcct ctccc                   45

<210> SEQ ID NO 133
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 133
gcaggctctt cgagtaccag aagagtggct taactatgcg gcatcagagc              50

<210> SEQ ID NO 134
<211> LENGTH: 48
<212> TYPE: DNA
<213> ORGANISM: Artificial Sequence

```
<220> FEATURE:
<223> OTHER INFORMATION: Synthetic Oligonucleotide

<400> SEQUENCE: 134
gatccagctc ttcgattatc tgaagagtat acgcaaaccg cctctccc                    48

<210> SEQ ID NO 135
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 135
gcaggctctt cgaataccag aagagtggct taactatgcg gcatcagagc                  50

<210> SEQ ID NO 136
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 136
gatccagctc ttcgatctga agagtatacg caaaccgcct ctccc                       45

<210> SEQ ID NO 137
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 137
gcaggctctt cgaccatcag aagagtggct taactatgcg gcatcagagc                  50

<210> SEQ ID NO 138
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 138
gatccagctc ttcgactacc tgaagagtat acgcaaaccg cctctccc                    48

<210> SEQ ID NO 139
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 139
gcaggctctt cgagtatcag aagagtggct taactatgcg gcatcagagc                  50

<210> SEQ ID NO 140
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 140
gatccagctc ttcgatcacc tgaagagtat acgcaaaccg cctctccc                    48
```

<210> SEQ ID NO 141
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 141
gctgcatgcc tgcagactct tc                                          22

<210> SEQ ID NO 142
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 142
gggaaacgac aatctgatcc aactcttc                                    28

<210> SEQ ID NO 143
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 143
gcagactctt caacccgaag agcggcttaa ctatgcggca tcagagc                47

<210> SEQ ID NO 144
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 144
gatccaactc ttctactatc cgaagagcat acgcaaaccg cctctccc              48

<210> SEQ ID NO 145
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 145
gcagactctt caagtacccg aagagcggct taactatgcg gcatcagagc            50

<210> SEQ ID NO 146
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 146
gatccaactc ttctatccga agagcatacg caaaccgcct ctccc                 45

<210> SEQ ID NO 147
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 147
gcagactctt caagtacccg aagagcggct taactatgcg gcatcagagc          50

<210> SEQ ID NO 148
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 148
gatccaactc ttctattatc cgaagagcat acgcaaaccg cctctccc            48

<210> SEQ ID NO 149
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 149
gcagactctt caaatacccg aagagcggct taactatgcg gcatcagagc          50

<210> SEQ ID NO 150
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 150
gatccaactc ttctatccga agagcatacg caaaccgcct ctccc               45

<210> SEQ ID NO 151
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 151
gcagactctt caaccatccg aagagcggct taactatgcg gcatcagagc          50

<210> SEQ ID NO 152
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 152
gatccaactc ttctactacc cgaagagcat acgcaaaccg cctctccc            48

<210> SEQ ID NO 153
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 153
gcagactctt caagtatccg aagagcggct taactatgcg gcatcagagc          50

<210> SEQ ID NO 154

<210> SEQ ID NO 154
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 154
gatccaactc ttctatcacc cgaagagcat acgcaaaccg cctctccc                48

<210> SEQ ID NO 155
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 155
gtttttcatt accgacgaga tcgaggcgga g                                  31

<210> SEQ ID NO 156
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 156
gcgcacagcc gacgagctgc aaaaag                                        26

<210> SEQ ID NO 157
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 157
caggcgctct tacgcttcct cgctc                                         25

<210> SEQ ID NO 158
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 158
ttcgccgcca agttcttcag caatatc                                       27

<210> SEQ ID NO 159
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 159
cgagcccctg atgttcttcg tccag                                         25

<210> SEQ ID NO 160
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 160
ctccgcctcg atctcgtcgg taatgaaaaa c                                31

<210> SEQ ID NO 161
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 161 cttttgcag ctcgtcggct gtgcgc                                       26

<210> SEQ ID NO 162
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 162
gagcgaggaa gcgtaagagc gcctg                                       25

<210> SEQ ID NO 163
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 163
gatattgctg aagaacttgg cggcgaa                                     27

<210> SEQ ID NO 164
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 164
ctggacgaag aacatcaggg gctcg                                       25

<210> SEQ ID NO 165
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 165
ctcttaggtt tacccgccaa ta                                          22

<210> SEQ ID NO 166
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 166
aacgtgactc ccttaattct cc                                          22

<210> SEQ ID NO 167
<211> LENGTH: 42
<212> TYPE: DNA

<213> ORGANISM: Artificial Sequence
<220> FEATURE:
<223> OTHER INFORMATION: Synthetic Oligonucleotide

<400> SEQUENCE: 167
ctcttcgacc ccggggctgg cttaactatg cggcatcaga gc            42

<210> SEQ ID NO 168
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 168
gccccggggt cgaagagctg catgtgtcag agg                       33

<210> SEQ ID NO 169
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 169
gccacctgac gtctaagaaa                                      20

<210> SEQ ID NO 170
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 170
cctgattctg tggataaccg tatta                                25

<210> SEQ ID NO 171
<211> LENGTH: 72
<212> TYPE: DNA
<213> ORGANISM: Artificial Sequence
<220> FEATURE:
<223> OTHER INFORMATION: Synthetic Oligonucleotide

<400> SEQUENCE: 171
acatgcagct cttccaccgg tgctggtggt tgctgccctg gttgctgcgg tggtgatgga    60
agagcttcct cg                                                        72

<210> SEQ ID NO 172
<211> LENGTH: 72
<212> TYPE: DNA
<213> ORGANISM: Artificial Sequence
<220> FEATURE:
<223> OTHER INFORMATION: Synthetic Oligonucleotide

<400> SEQUENCE: 172
cgaggaagct cttccatcac caccgcagca accagggcag caaccaccag caccggtgga    60
agagctgcat gt                                                        72

<210> SEQ ID NO 173
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 173
acatgcagct cttccaccgt gagcaagggc gagga					35

<210> SEQ ID NO 174
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 174
cgaggaagct cttccatcct tgtacagctc gtccatgc					38

<210> SEQ ID NO 175
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 175
acatgcagct cttccacccc taagaagaag cgtaaggtcg aggaccctga tggaagagct		60 tcctcg									66

<210> SEQ ID NO 176
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 176
cgaggaagct cttccatcag ggtcctcgac cttacgcttc ttcttagggg tggaagagct		60 gcatgt									66

<210> SEQ ID NO 177
<211> LENGTH: 93
<212> TYPE: DNA
<213> ORGANISM: Artificial Sequence
<220> FEATURE:
<223> OTHER INFORMATION: Synthetic Oligonucleotide

<400> SEQUENCE: 177
acatgcagct cttccaccgc taccaacttc tctctcctca agcaggctgg tgacgtcgag		60 gagaaccctg gtcctgatgg aagagcttcc tcg					93

<210> SEQ ID NO 178
<211> LENGTH: 93
<212> TYPE: DNA
<213> ORGANISM: Artificial Sequence
<220> FEATURE:
<223> OTHER INFORMATION: Synthetic Oligonucleotide

<400> SEQUENCE: 178
cgaggaagct cttccatcag gaccagggtt ctcctcgacg tcaccagcct gcttgaggag		60 agagaagttg gtagcggtgg aagagctgca tgt					93

<210> SEQ ID NO 179
<211> LENGTH: 96
<212> TYPE: DNA
<213> ORGANISM: Artificial Sequence
<220> FEATURE:

<223> OTHER INFORMATION: Synthetic Oligonucleotide

<400> SEQUENCE: 179

```
acatgcagct cttccacccg tgctgagggt cgtggttctc tcctcacctg cggtgacgtc    60
gaggagaacc ctggtcctga tggaagagct tcctcg                              96
```

<210> SEQ ID NO 180
<211> LENGTH: 96
<212> TYPE: DNA
<213> ORGANISM: Artificial Sequence
<220> FEATURE:
<223> OTHER INFORMATION: Synthetic Oligonucleotide

<400> SEQUENCE: 180

```
cgaggaagct cttccatcag gaccagggtt ctcctcgacg tcaccgcagg tgaggagaga    60
accacgaccc tcagcacggg tggaagagct gcatgt                              96
```

<210> SEQ ID NO 181
<211> LENGTH: 90
<212> TYPE: DNA
<213> ORGANISM: Artificial Sequence
<220> FEATURE:
<223> OTHER INFORMATION: Synthetic Oligonucleotide

<400> SEQUENCE: 181

```
acatgcagct cttccacccc ttgctctaac gctgctgacg aggtcgctac ccctgaggac    60
gtcgagcctg gtgatggaag agcttcctcg                                     90
```

<210> SEQ ID NO 182
<211> LENGTH: 90
<212> TYPE: DNA
<213> ORGANISM: Artificial Sequence
<220> FEATURE:
<223> OTHER INFORMATION: Synthetic Oligonucleotide

<400> SEQUENCE: 182

```
cgaggaagct cttccatcac caggctcgac gtcctcaggg gtagcgacct cgtcagcagc    60
gttagagcaa ggggtggaag agctgcatgt                                     90
```

<210> SEQ ID NO 183
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 183

```
acatgcagct cttccaccat ggcaaaggat gtggaag                             37
```

<210> SEQ ID NO 184
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 184

```
gatgtataag aataggagag tggctacgaa c                                   31
```

<210> SEQ ID NO 185
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 185
gttcgtagcc actctcctat tcttatacat c					31

<210> SEQ ID NO 186
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 186
cgaggaagct cttccatcag atctgtacag ctcgtcc					37

<210> SEQ ID NO 187
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 187
acatgcagct cttccaccca caacatacga gccggaagca					40

<210> SEQ ID NO 188
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 188
cgaggaagct cttccatcca tggctatcgt tcgtaaatgg tg					42

<210> SEQ ID NO 189
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 189
acatgcagct cttccaccta agtagctgaa tcccgcggcc atgct					45

<210> SEQ ID NO 190
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 190
cgaggaagct cttccatctc gggctaggcc cgacgtc					37

<210> SEQ ID NO 191
<211> LENGTH: 156
<212> TYPE: DNA
<213> ORGANISM: Artificial Sequence
<220> FEATURE:
<223> OTHER INFORMATION: Synthetic Oligonucleotide

<400> SEQUENCE: 191
acatgcagct cttccaccct cctcgctatc caccctaccg aggctcgtca caagcagaag					60 atcgtcgctc ctgtcaagca gaccctcaac ttcgacctcc tcaagctcgc tggtgacgtc    120
gagtctaacc ctggtcctga tggaagagct tcctcg                              156

<210> SEQ ID NO 192
<211> LENGTH: 156
<212> TYPE: DNA
<213> ORGANISM: Artificial Sequence
<220> FEATURE:
<223> OTHER INFORMATION: Synthetic Oligonucleotide

<400> SEQUENCE: 192
cgaggaagct cttccatcag gaccagggtt agactcgacg tcaccagcga gcttgaggag    60
gtcgaagttg agggtctgct tgacaggagc gacgatcttc tgcttgtgac gagcctcggt   120
agggtggata gcgaggaggg tggaagagct gcatgt                              156

<210> SEQ ID NO 193
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 193
acatgcagct cttccaccat ggattacaag gatgatgatg at                        42

<210> SEQ ID NO 194
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 194
gaatcgaaaa gaagtgcacc gataagg                                         27

<210> SEQ ID NO 195
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 195
ccttatcggt gcacttcttt tcgattc                                         27

<210> SEQ ID NO 196
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 196
actcgtaaag aagtgagtgc tttgg                                           25

<210> SEQ ID NO 197
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 197
ccaaagcact cacttcttta cgagt                                           25

<210> SEQ ID NO 198
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 198
tgctcgtgaa gtgaatctcc ctg                                          23

<210> SEQ ID NO 199
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 199
cagggagatt cacttcacga gca                                          23

<210> SEQ ID NO 200
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 200
cttagatgga agtgcaagct cgtt                                         24

<210> SEQ ID NO 201
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 201
aacgagcttg cacttccatc taag                                         24

<210> SEQ ID NO 202
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 202
cgaggaagct cttccatctt tatgcctgca ggtcgcgag                         39

<210> SEQ ID NO 203
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 203
cgagctgcat gcctgcagcc ctcttcaagt acccgaagag cggcttaact a           51

<210> SEQ ID NO 204
<211> LENGTH: 51
<212> TYPE: DNA
<213> ORGANISM: Artificial Sequence
<220> FEATURE:

<223> OTHER INFORMATION: Synthetic Oligonucleotide

<400> SEQUENCE: 204
tagttaagcc gctcttcggg tacttgaaga gggctgcagg catgcagctc g    51

<210> SEQ ID NO 205
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 205
cgagctgcat gcctgcagcc ctcttcaaat acccgaagag cggcttaact a    51

<210> SEQ ID NO 206
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 206
tagttaagcc gctcttcggg tatttgaaga gggctgcagg catgcagctc g    51

<210> SEQ ID NO 207
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 207
cgagctgcat gcctgcagcc ctcttcaacc atccgaagag cggcttaact a    51

<210> SEQ ID NO 208
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 208
tagttaagcc gctcttcgga tggttgaaga gggctgcagg catgcagctc g    51

<210> SEQ ID NO 209
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 209
cgagctgcat gcctgcagcc ctcttcaagt atccgaagag cggcttaact a    51

<210> SEQ ID NO 210
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 210
tagttaagcc gctcttcgga tacttgaaga gggctgcagg catgcagctc g    51

<210> SEQ ID NO 211
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 211
gtttgcgtat gctcttcgga taatagaaga gggggatcag attgtcgttt cccgccttca    60
gtttaaacta tcagtgtttg acag                                          84

<210> SEQ ID NO 212
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 212
ctgtcaaaca ctgatagttt aaactgaagg cgggaaacga caatctgatc cccctcttct    60
attatccgaa gagcatacgc aaac                                          84

<210> SEQ ID NO 213
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 213
gtttgcgtat gctcttcggg tagtagaaga gggggatcag attgtcgttt cccgccttca    60
gtttaaacta tcagtgtttg acag                                          84

<210> SEQ ID NO 214
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 214
ctgtcaaaca ctgatagttt aaactgaagg cgggaaacga caatctgatc cccctcttct    60
actacccgaa gagcatacgc aaac                                          84

<210> SEQ ID NO 215
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 215
gtttgcgtat gctcttcggg tgatagaaga gggggatcag attgtcgttt cccgccttca    60
gtttaaacta tcagtgtttg acag                                          84

<210> SEQ ID NO 216
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 216

```
ctgtcaaaca ctgatagttt aaactgaagg cgggaaacga caatctgatc ccctcttct    60 atcacccgaa gagcatacgc aaac                                          84
```

<210> SEQ ID NO 217
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 217

```
acatgcagct cttccaccat gttacgtcct gtagaaacc                          39
```

<210> SEQ ID NO 218
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 218

```
cgagcatctc ctcagcgtaa gg                                            22
```

<210> SEQ ID NO 219
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 219

```
ccttacgctg aggagatgct cg                                            22
```

<210> SEQ ID NO 220
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 220

```
tgactgcctc ctcgctgtac ag                                            22
```

<210> SEQ ID NO 221
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 221

```
ctgtacagcg aggaggcagt ca                                            22
```

<210> SEQ ID NO 222
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 222

```
acactgatac tcctcactcc aca                                           23
```

<210> SEQ ID NO 223
<211> LENGTH: 23

```
<212> TYPE: DNA
<213> ORGANISM: Artificial Sequence
<220> FEATURE:
<223> OTHER INFORMATION: Synthetic Oligonucleotide

<400> SEQUENCE: 223
tgtggagtga ggagtatcag tgt                                              23

<210> SEQ ID NO 224
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 224
cgaggaagct cttccatctt gtttgcctcc ctgctgcggt                            40

<210> SEQ ID NO 225
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 225
acatgcagct cttccaccat gaaaaagcct gaactcacc                             39

<210> SEQ ID NO 226
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 226
cacagcccct cctcgcctgg ta                                               22

<210> SEQ ID NO 227
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 227
taccaggcga ggaggggctg tg                                               22

<210> SEQ ID NO 228
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 228
cgtaacgcct cctccagcaa cg                                               22

<210> SEQ ID NO 229
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 229
```
cgttgctgga ggaggcgtta cg                                            22

<210> SEQ ID NO 230
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 230
cgaggaagct cttccatcac gtttgtaatc gatggcttct gg                      42

<210> SEQ ID NO 231
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 231
acatgcagct cttccaccat ggaagatgcc aaaaacataa ag                      42

<210> SEQ ID NO 232
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 232
gggcgtatct tttcatagcc t                                             21

<210> SEQ ID NO 233
<211> LENGTH: 21
<212> TYPE: DNA
<213> ORGANISM: Artificial Sequence
<220> FEATURE:
<223> OTHER INFORMATION: AGG CTA TGA AAA GAT ACG CCC

<400> SEQUENCE: 233
aggctatgaa aagatacgcc c                                             21

<210> SEQ ID NO 234
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 234
aagaattgaa gtgagttttc actgc                                         25

<210> SEQ ID NO 235
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 235
gcagtgaaaa ctcacttcaa ttctt                                         25

<210> SEQ ID NO 236
<211> LENGTH: 26
<212> TYPE: DNA
<213> ORGANISM: Artificial Sequence

```
<220> FEATURE:
<223> OTHER INFORMATION: Synthetic Oligonucleotide

<400> SEQUENCE: 236
cctcagaaac agttcttctt caaatc                                          26

<210> SEQ ID NO 237
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 237
gatttgaaga agaactgttt ctgagg                                          26

<210> SEQ ID NO 238
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 238
acatgcagct cttccaccga gggcggtccg ctgcctttt                            39

<210> SEQ ID NO 239
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 239
cgaggaagct cttccatccc ttgtttgcct ggcggcagt                            39

<210> SEQ ID NO 240
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 240
aaccgtctat cagggcgatg gc                                              22

<210> SEQ ID NO 241
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 241
ggctttccac ttccccgaaa cc                                              22

<210> SEQ ID NO 242
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 242
cgcaagcttg gatcgaagag ctcttag                                         27
```

```
<210> SEQ ID NO 243
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 243
ctaagagctc ttcgatccaa gcttgcg                                27

<210> SEQ ID NO 244
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 244
aatttgtcgc ttctc                                             15

<210> SEQ ID NO 245
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 245
agccagaatt tgtcgcttct c                                      21

<210> SEQ ID NO 246
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 246
ctcttcgctg tttaa                                             15

<210> SEQ ID NO 247
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 247
ctcttcgctg tttaagaccg at                                     22

<210> SEQ ID NO 248
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 248
gttcactgtc ttctc                                             15

<210> SEQ ID NO 249
<211> LENGTH: 22
<212> TYPE: DNA
<213> ORGANISM: Artificial Sequence
<220> FEATURE:
<223> OTHER INFORMATION: Synthetic Oligonucleotide
```

```
<400> SEQUENCE: 249
ccggcgtgtt cactgtcttc tc                                              22

<210> SEQ ID NO 250
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 250
ctcttctgtc acttg                                                      15

<210> SEQ ID NO 251
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 251
ctcttctgtc acttgtgcgg cc                                              22

<210> SEQ ID NO 252
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 252
cactgccagt tgctcttcat atagca                                          26

<210> SEQ ID NO 253
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (26)..(26)
<223> OTHER INFORMATION: "a" at position 26 is covalently linked to
      Acridine

<400> SEQUENCE: 253
cactgccagt tgctcttcat atagca                                          26

<210> SEQ ID NO 254
<211> LENGTH: 13
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: "g" at position 1 is covalently linked to
      Acridine
<220> FEATURE:
<221> NAME/KEY: misc_feature
<222> LOCATION: (2)..(8)
<223> OTHER INFORMATION: The sugar (ribose) is switched to the analog
      2',4'-BNANC (2'-O,4'-aminoethylene bridged nucleic acid).
<220> FEATURE:
<221> NAME/KEY: misc_feature
<222> LOCATION: (11)..(11)
<223> OTHER INFORMATION: The sugar (ribose) is switched to the analog
```

```
        2',4'-BNANC (2'-O,4'-aminoethylene bridged nucleic acid).
<220> FEATURE:
<221> NAME/KEY: misc_feature
<222> LOCATION: (13)..(13)
<223> OTHER INFORMATION: The sugar (ribose) is switched to the analog
        2',4'-BNANC (2'-O,4'-aminoethylene bridged nucleic acid).

<400> SEQUENCE: 254
gccagttgct ctc                                                          13

<210> SEQ ID NO 255
<211> LENGTH: 225
<212> TYPE: DNA
<213> ORGANISM: Artificial Sequence
<220> FEATURE:
<223> OTHER INFORMATION: Synthetic Oligonucleotide

<400> SEQUENCE: 255
acatgcagct cttccaccaa actcataaca gggaactata attaggacta aagaagattc        60
aacgtacatt gatctgacac agtagattta gttgtctctt gtacatacac agtatctagg      120
attattcaac gaaaacaata tcaattgtct ctacagaaac caacggccag tactcttttg      180
ccctaaaaag accgtaaccc taattgtcac actgagaatc taacg                      225

<210> SEQ ID NO 256
<211> LENGTH: 316
<212> TYPE: DNA
<213> ORGANISM: Artificial Sequence
<220> FEATURE:
<223> OTHER INFORMATION: Synthetic Oligonucleotide

<400> SEQUENCE: 256
tagcagatgc tacgatctgt cagcaactga gaagtctatt tgcttttgtg attcaggaat       60
atgctgaatt cctgcacgaa ttcatgtgcg ctgtaaagca gaactatgga gagaaagtgt      120
tggttcaggt gagccatagg atactctctt aagaactatg attgttgtca gaactacgat      180
aaaagatgtc cggaattaat atcatacact catcttttca gtttgaagat tttgcaaacc      240
acaatgcgtt tgacctttg tctaagtaca gtgatagctt tctgccactt gttgtatcga       300
tggaagagct tcctcg                                                      316

<210> SEQ ID NO 257
<211> LENGTH: 210
<212> TYPE: DNA
<213> ORGANISM: Artificial Sequence
<220> FEATURE:
<223> OTHER INFORMATION: Synthetic Oligonucleotide

<400> SEQUENCE: 257
gtcacactga gaatctaacg attgccagtt actcttctgg gacctacgac gaaggatgac       60
tccgtccacg ttcttcttca ctgtttgaca ataagctcca attttcagac ttttcatttc      120
aaacttgtgg gtctcatttt cctctggcct atataaatcc actatcctcc actgccagtt      180
gctcttcata tagcagatgc tacgatctgt                                       210

<210> SEQ ID NO 258
<211> LENGTH: 210
<212> TYPE: DNA
<213> ORGANISM: Artificial Sequence
<220> FEATURE:
<223> OTHER INFORMATION: Synthetic Oligonucleotide

<400> SEQUENCE: 258
```

```
gtcacactga gaatctaacg attaggtccc gctcttctgg gacctacgac gaaggatgac    60
tccgtccacg ttcttcttca ctgtttgaca ataagctcca attttcagac ttttcatttc   120
aaacttgtgg gtctcatttt cctctggcct atataaatcc actatcctcc actgccagtt   180
gctcttcata tagcagatgc tacgatctgt                                    210
```

<210> SEQ ID NO 259
<211> LENGTH: 210
<212> TYPE: DNA
<213> ORGANISM: Artificial Sequence
<220> FEATURE:
<223> OTHER INFORMATION: Synthetic Oligonucleotide

<400> SEQUENCE: 259

```
gtcacactga gaatctaacg attgccagtt actcttctgg gacctacgac gaaggatgac    60
tccgtccacg ttcttcttca ctgtttgaca ataagctcca attttcagac ttttcatttc   120
aaacttgtgg gtctcatttt cctctggcct atataaatcc actatcctcc actgccagtt   180
cctcttcata tagcagatgc tacgatctgt                                    210
```

<210> SEQ ID NO 260
<211> LENGTH: 210
<212> TYPE: DNA
<213> ORGANISM: Artificial Sequence
<220> FEATURE:
<223> OTHER INFORMATION: Synthetic Oligonucleotide

<400> SEQUENCE: 260

```
gtcacactga gaatctaacg attgccagac tctcttctgg gacctacgac gaaggatgac    60
tccgtccacg ttcttcttca ctgtttgaca ataagctcca attttcagac ttttcatttc   120
aaacttgtgg gtctcatttt cctctggcct atataaatcc actatcctcc actatgagtt   180
gctcttcata tagcagatgc tacgatctgt                                    210
```

<210> SEQ ID NO 261
<211> LENGTH: 210
<212> TYPE: DNA
<213> ORGANISM: Artificial Sequence
<220> FEATURE:
<223> OTHER INFORMATION: Synthetic Oligonucleotide

<400> SEQUENCE: 261

```
gtcacactga gaatctaacg attggctgcc actcttctgg gacctacgac gaaggatgac    60
tccgtccacg ttcttcttca ctgtttgaca ataagctcca attttcagac ttttcatttc   120
aaacttgtgg gtctcatttt cctctggcct atataaatcc actatcctcc actggctgcc   180
gctcttcata tagcagatgc tacgatctgt                                    210
```

<210> SEQ ID NO 262
<211> LENGTH: 1960
<212> TYPE: DNA
<213> ORGANISM: Artificial Sequence
<220> FEATURE:
<223> OTHER INFORMATION: Synthetic Oligonucleotide

<400> SEQUENCE: 262

```
aacgctgctt cggcctggta atggcccgcc gccttccagc gttcgaccca ggcgttaggg    60
tcaatgcggg tcgcttcact tacgccaatg tcgttatcca gcggtgcacg ggtgaactga   120
tcgcgcagcg gcgtcagcag ttgtttttta tcgccaatcc acatctgtga aagaaagcct   180
gactggcggt taaattgcca acgcttatta cccagctcga tgcaaaaatc catttcgctg   240
```

```
gtggtcagat gcgggatggc gtgggacgcg gcggggagcg tcacactgag gttttccgcc      300
agacgccact gctgccaggc gctgatgtgc ccggcttctg accatgcggt cgcgttcggt      360
tgcactacgc gtactgtgag ccagagttgc ccggcgctct ccggctgcgg tagttcaggc      420
agttcaatca actgtttacc ttgtggagcg acatccagag gcacttcacc gcttgccagc      480
ggcttaccat ccagcgccac catccagtgc aggagctcgt tatcgctatg acggaacagg      540
tattcgctgg tcacttcgat ggtttgcccg gataaacgga actggaaaaa ctgctgctgg      600
tgttttgctt ccgtcagcgc tggatgcggc gtgcggtcgg caaagaccag accgttcata      660
cagaactggc gatcgttcgg cgtatcgcca aaatcaccgc cgtaagccga ccacgggttg      720
ccgttttcat catatttaat cagcgactga tccacccagt cccagacgaa gccgccctgt      780
aaacggggat actgacgaaa cgcctgccag tatttagcga aaccgccaag actgttaccc      840
atcgcgtggg cgtattcgca aaggatcagc gggcgcgtct ctccaggtag cgaaagccat      900
tttttgatgg accatttcgg cacagccggg aagggctggt cttcatccac gcgcgcgtac      960
atcgggcaaa taatatcggt ggccgtggtg tcggctccgc cgccttcata ctgcaccggg     1020
cgggaaggat cgacagattt gatccagcga tacagcgcgt cgtgattagc gccgtggcct     1080
gattcattcc ccagcgacca gatgatcaca ctcgggtgat tacgatcgcg ctgcaccatt     1140
cgcgttacgc gttcgctcat cgccggtagc cagcgcggat catcggtcag acgattcatt     1200
ggcaccatgc cgtgggtttc aatattggct tcatccacca catacaggcc gtagcggtcg     1260
cacagcgtgt accacagcgg atggttcgga taatgcgaac agcgcacggc gttaaagttg     1320
ttctgcttca tcagcaggat atcctgcacc atcgtctgct catccatgac ctgaccatgc     1380
agaggatgat gctcgtgacg gttaacgcct cgaatcagca acggcttgcc gttcagcagc     1440
agcagaccat tttcaatccg cacctcgcgg aaaccgacat cgcaggcttc tgcttcaatc     1500
agcgtgccgt cggcggtgtg cagttcaacc accgcacgat agagattcgg gatttcggcg     1560
ctccacagtt tcgggttttc gacgttcaga cgtagtgtga cgcgatcggc ataaccacca     1620
cgctcatcga taatttcacc gccgaaaggc gcggtgccgc tggcgacctg cgtttcaccc     1680
tgccataaag aaactgttac ccgtaggtag tcacgcaact cgccgcacat ctgaacttca     1740
gcctccagta cagcgcggct gaaatcatca ttaaagcgag tggcaacatg gaaatcgctg     1800
atttgtgtag tcggtttatg cagcaacgag acgtcacgga aaatgccgct catccgccac     1860
atatcctgat cttccagata actgccgtca ctccagcgca gcaccatcac cgcgaggcgg     1920
ttttctccgg cgcgtaaaaa tgcgctcagg tcaaattcag                           1960
```

<210> SEQ ID NO 263
<211> LENGTH: 696
<212> TYPE: DNA
<213> ORGANISM: Artificial Sequence
<220> FEATURE:
<223> OTHER INFORMATION: Synthetic Oligonucleotide

<400> SEQUENCE: 263

```
attcgagctg catgcctgca ggctcttcga gtatcagaag agtggcttaa ctatgcggca       60
tcagagctta ttttgacac cagaccaact ggtaatggta cgaccggcg ctcagctgga        120 attccgccga tactgacggg ctccaggagt cgtcgccacc aatccccata tggaaaccgt      180
cgatattcag ccatgtgcct tcttccgcgt gcagcagatg gcgatggctg gtttccatca      240
gttgctgttg actgtagcgg ctgatgttga actggaagtc gccgcgccac tggtgtgggc      300
```

```
cataattcaa ttcgcgcgtc cgcagcgca gaccgttttc gctcgggaag acgtacgggg    360
tatacatgtc tgacaatggc agatcccagc ggtcaaaaca ggcggcagta aggcggtcgg    420
gatagttttc ttgcggccct aatccgagcc agtttacccg ctctgctacc tgcgccagct    480
ggcagttcag gccaatccgc gccggatgcg gtgtatcgct cgccacttca acatcaacgg    540
taatcgccat ttgaccacta ccatcaatcc ggtaggtttt ccggctgata aataaggttt    600 tccctgatg  ctgccacgcg tgagcggtcg taatcagcac cgcatcagca agtgtatctg    660
ccgtgcactg caacaacgct gcttcggcct ggtaat                             696
```

<210> SEQ ID NO 264  
<211> LENGTH: 718  
<212> TYPE: DNA  
<213> ORGANISM: Artificial Sequence  
<220> FEATURE:  
<223> OTHER INFORMATION: Synthetic Oligonucleotide

<400> SEQUENCE: 264

```
aatgcgctca ggtcaaattc agacggcaaa cgactgtcct ggccgtaacc gacccagcgc     60
ccgttgcacc acagatgaaa cgccgagtta acgccatcaa aaataattcg cgtctggcct    120
tcctgtagcc agctttcatc aacattaaat gtgagcgagt aacaacccgt cggattctcc    180
gtgggaacaa acggcggatt gaccgtaatg ggataggtca cgttggtgta gatgggcgca    240
tcgtaaccgt gcatctgcca gtttgagggg acgacgacga tatcggcctc aggaagatcg    300
cactccagcc agctttccgg caccgcttct ggtgccggaa accaggcaaa gcgccattcg    360
ccattcaggc tgcgcaactg ttgggaaggg cgatcggtgc gggcctcgac ggccagtgaa    420
tccgtaatca tggtcatagc tgttctgtg  tgaaattgtt atccgctcac aattccacac    480
aacatacgag ccggaagcat aaagtgtaaa gcctggggtg cctaatgagt gagctaactc    540
acattaattg cgttgcgctc actgcccgct ttccagtcgg gaaacctgtc gtgccagctg    600
cattaatgaa tcggccaacg cgcggggaga ggcggtttgc gtatactctt caggtaatcg    660
aagagctgga tcagattgtc gtttcccgcc ttcagtttaa actatcagtg tttgacag     718
```

<210> SEQ ID NO 265  
<211> LENGTH: 696  
<212> TYPE: DNA  
<213> ORGANISM: Artificial Sequence  
<220> FEATURE:  
<223> OTHER INFORMATION: Synthetic Oligonucleotide

<400> SEQUENCE: 265

```
attcgagctg catgcctgca ggctcttcga atatcagaag agtggcttaa ctatgcggca     60
tcagagctta tttttgacac cagaccaact ggtaatggta gcgaccggcg ctcagctgga    120
attccgccga tactgacggg ctccaggagt cgtcgccacc aatccccata tggaaaccgt    180
cgatattcag ccatgtgcct tcttccgcgt gcagcgatg  gcgatggctg gtttccatca    240
gttgctgttg actgtagcgg ctgatgttga actggaagtc gccgcgccac tggtgtgggc    300
cataattcaa ttcgcgcgtc cgcagcgca  gaccgttttc gctcgggaag acgtacgggg    360
tatacatgtc tgacaatggc agatcccagc ggtcaaaaca ggcggcagta aggcggtcgg    420
gatagttttc ttgcggccct aatccgagcc agtttacccg ctctgctacc tgcgccagct    480
ggcagttcag gccaatccgc gccggatgcg gtgtatcgct cgccacttca acatcaacgg    540
taatcgccat ttgaccacta ccatcaatcc ggtaggtttt ccggctgata aataaggttt    600 tccctgatg  ctgccacgcg tgagcggtcg taatcagcac cgcatcagca agtgtatctg    660
```

```
ccgtgcactg caacaacgct gcttcggcct ggtaat                               696
```

<210> SEQ ID NO 266
<211> LENGTH: 718
<212> TYPE: DNA
<213> ORGANISM: Artificial Sequence
<220> FEATURE:
<223> OTHER INFORMATION: Synthetic Oligonucleotide

<400> SEQUENCE: 266

```
aatgcgctca ggtcaaattc agacggcaaa cgactgtcct ggccgtaacc gacccagcgc      60
ccgttgcacc acagatgaaa cgccgagtta acgccatcaa aataattcg cgtctggcct     120
tcctgtagcc agctttcatc aacattaaat gtgagcgagt aacaacccgt cggattctcc    180
gtgggaacaa acggcggatt gaccgtaatg ggataggtca cgttggtgta gatgggcgca    240
tcgtaaccgt gcatctgcca gtttgagggg acgacgacag tatcggcctc aggaagatcg    300
cactccagcc agctttccgg caccgcttct ggtgccggaa accaggcaaa cgccattcg     360
ccattcaggc tgcgcaactg ttgggaaggg cgatcggtgc gggcctcgac ggccagtgaa    420
tccgtaatca tggtcatagc tgtttctgtg tgaaattgtt atccgctcac aattccacac    480
aacatacgag ccggaagcat aaagtgtaaa gcctggggtg cctaatgagt gagctaactc    540
acattaattg cgttgcgctc actgcccgct ttccagtcgg gaaacctgtc gtgccagctg    600
cattaatgaa tcggccaacg cgcggggaga ggcggtttgc gtatactctt caggtgatcg    660
aagagctgga tcagattgtc gtttcccgcc ttcagtttaa actatcagtg tttgacag      718
```

<210> SEQ ID NO 267
<211> LENGTH: 697
<212> TYPE: DNA
<213> ORGANISM: Artificial Sequence
<220> FEATURE:
<223> OTHER INFORMATION: Synthetic Oligonucleotide

<400> SEQUENCE: 267

```
attcgagctg catgcctgca gccctcttca agtatccgaa gagcggctta actatgcggc      60
atcagagctt attttttgaca ccagaccaac tggtaatggt agcgaccggc gctcagctgg    120
aattccgccg atactgacgg gctccaggag tcgtcgccac caatcccat atggaaaccg     180
tcgatattca gccatgtgcc ttcttccgcg tgcagcagat ggcgatggct ggtttccatc    240
agttgctgtt gactgtagcg gctgatgttg aactggaagt cgccgcgcca ctggtgtggg    300
ccataattca attcgcgcgt cccgcagcgc agaccgtttt cgctcgggaa gacgtacggg    360
gtatacatgt ctgacaatgg cagatcccag cggtcaaaac aggcggcagt aaggcggtcg    420
ggatagtttt cttgcggccc taatccgagc cagtttaccc gctctgctac ctgcgccagc    480
tggcagttca ggccaatccg cgccggatgc ggtgtatcgc tcgccacttc aacatcaacg    540
gtaatcgcca tttgaccact accatcaatc cggtaggttt tccggctgat aaataaggtt    600
ttcccctgat gctgccacgc gtgagcggtc gtaatcagca ccgcatcagc aagtgtatct    660
gccgtgcact gcaacaacgc tgcttcggcc tggtaat                             697
```

<210> SEQ ID NO 268
<211> LENGTH: 718
<212> TYPE: DNA
<213> ORGANISM: Artificial Sequence
<220> FEATURE:
<223> OTHER INFORMATION: Synthetic Oligonucleotide

<400> SEQUENCE: 268

```
aatgcgctca ggtcaaattc agacggcaaa cgactgtcct ggccgtaacc gacccagcgc      60
ccgttgcacc acagatgaaa cgccgagtta acgccatcaa aaataattcg cgtctggcct    120
tcctgtagcc agcttttcatc aacattaaat gtgagcgagt aacaacccgt cggattctcc    180
gtgggaacaa acggcggatt gaccgtaatg ggataggtca cgttggtgta gatgggcgca    240
tcgtaaccgt gcatctgcca gtttgagggg acgacgacag tatcggcctc aggaagatcg    300
cactccagcc agctttccgg caccgcttct ggtgccggaa accaggcaaa gcgccattcg    360
ccattcaggc tgcgcaactg ttgggaaggg cgatcggtgc gggcctcgac ggccagtgaa    420
tccgtaatca tggtcatagc tgtttctgtg tgaaattgtt atccgctcac aattccacac    480
aacatacgag ccggaagcat aaagtgtaaa gcctggggtg cctaatgagt gagctaactc    540
acattaattg cgttgcgctc actgcccgct ttccagtcgg gaaacctgtc gtgccagctg    600
cattaatgaa tcggccaacg cgcggggaga ggcggtttgc gtatgctctt cgggtaatag    660
aagaggggga tcagattgtc gtttcccgcc ttcagtttaa actatcagtg tttgacag     718
```

<210> SEQ ID NO 269
<211> LENGTH: 697
<212> TYPE: DNA
<213> ORGANISM: Artificial Sequence
<220> FEATURE:
<223> OTHER INFORMATION: Synthetic Oligonucleotide

<400> SEQUENCE: 269

```
attcgagctg catgcctgca gccctcttca aatatccgaa gagcggctta actatgcggc      60
atcagagctt attttttgaca ccagaccaac tggtaatggt agcgaccggc gctcagctgg    120
aattccgccg atactgacgg gctccaggag tcgtcgccac caatccccat atggaaaccg    180
tcgatattca gccatgtgcc ttcttccgcg tgcagcagat ggcgatggct ggtttccatc    240
agttgctgtt gactgtagcg gctgatgttg aactggaagt cgccgcgcca ctggtgtggg    300
ccataattca attcgcgcgt cccgcagcgc agaccgtttt cgctcgggaa gacgtacggg    360
gtatacatgt ctgacaatgg cagatcccag cggtcaaaac aggcggcagt aaggcggtcg    420
ggatagtttt cttgcggccc taatccgagc cagtttaccc gctctgctac ctgcgccagc    480
tggcagttca ggccaatccg cgccggatgc ggtgtatcgc tcgccacttc aacatcaacg    540
gtaatcgcca tttgaccact accatcaatc cggtaggttt tccggctgat aaataaggtt    600
ttcccctgat gctgccacgc gtgagcggtc gtaatcagca ccgcatcagc aagtgtatct    660
gccgtgcact gcaacaacgc tgcttcggcc tggtaat                              697
```

<210> SEQ ID NO 270
<211> LENGTH: 718
<212> TYPE: DNA
<213> ORGANISM: Artificial Sequence
<220> FEATURE:
<223> OTHER INFORMATION: Synthetic Oligonucleotide

<400> SEQUENCE: 270

```
aatgcgctca ggtcaaattc agacggcaaa cgactgtcct ggccgtaacc gacccagcgc      60
ccgttgcacc acagatgaaa cgccgagtta acgccatcaa aaataattcg cgtctggcct    120
tcctgtagcc agcttttcatc aacattaaat gtgagcgagt aacaacccgt cggattctcc    180
gtgggaacaa acggcggatt gaccgtaatg ggataggtca cgttggtgta gatgggcgca    240
tcgtaaccgt gcatctgcca gtttgagggg acgacgacag tatcggcctc aggaagatcg    300
```

```
cactccagcc agctttccgg caccgcttct ggtgccggaa accaggcaaa gcgccattcg    360
ccattcaggc tgcgcaactg ttgggaaggg cgatcggtgc gggcctcgac ggccagtgaa    420
tccgtaatca tggtcatagc tgtttctgtg tgaaattgtt atccgctcac aattccacac    480
aacatacgag ccggaagcat aaagtgtaaa gcctggggtg cctaatgagt gagctaactc    540
acattaattg cgttgcgctc actgcccgct ttccagtcgg gaaacctgtc gtgccagctg    600
cattaatgaa tcggccaacg cgcgggggaga ggcggtttgc gtatgctctt cgggtgatag    660
aagaggggga tcagattgtc gtttcccgcc ttcagtttaa actatcagtg tttgacag      718
```

<210> SEQ ID NO 271
<211> LENGTH: 247
<212> TYPE: DNA
<213> ORGANISM: Artificial Sequence
<220> FEATURE:
<223> OTHER INFORMATION: Synthetic Oligonucleotide

<400> SEQUENCE: 271

```
acatgcagct cttccaccgg gttactgatg agtccgtgag gacgaaacga gtaagctcgt     60
ctaacccaag gggtgacaag cgttttagag ctagaaatag caagttaaaa taaggctagt    120
ccgttatcaa cttgaaaaag tggcaccgag tcggtgcttt tggccggcat ggtcccagcc    180
tcctcgctgg cgccggctgg gcaacatgct tcggcatggc gaatgggacg atggaagagc    240
ttcctcg                                                              247
```

<210> SEQ ID NO 272
<211> LENGTH: 1924
<212> TYPE: DNA
<213> ORGANISM: Artificial Sequence
<220> FEATURE:
<223> OTHER INFORMATION: Synthetic Oligonucleotide

<400> SEQUENCE: 272

```
tcagatcccg ggtcaatagc attctcacca ataaaaaacg cccggcggca accgagcgtt     60
ctgaacaaat ccagatggag ttctgaggtc attactggat ctatcaacag gagtccaagc    120
ggccgctttt tttacctcct aaaagttaaa caaaattatt tctagaggga accgttgtg     180 gaattgtgag cgctcacaat tccacatatt ataattgtta tccgctcaca agcaaataa    240 attttttcatg atttcactgt gcatgaagct cgtaattgtt atccgctcac aattaaacaa    300
gcgctcatga gcccgaagtg gcgagcccga tcttccccat cggtgatgtc ggcgatatag    360
gcgccagcaa ccgcacctgt ggcgccggtg atgccggcca cgatgcgtcc ggcgtagagg    420
atcgagatct cgatcccgcg aaattaatac gactcactat aggggaattg tgagcggata    480
acaattcccc tctagaaata attttgttta actttaagaa ggagatatac catgggtctg    540
cctccgctgc tgagcctgcc gagcaatagc gcaccgcgta gcctgggtcg tgttgaaacc    600
cctccggaag ttgttgattt tatggttagc ctggccgaag caccgcgtgg tggtcgtgtt    660
ctggaaccgg catgtgccca tggtccgttt ctgcgtgcat ttcgtgaagc acatggcacc    720
ggttatcgtt ttgttggtgt tgaaattgat ccgaaagcac tggatctgcc accgtgggca    780
gaaggtattc tggcagattt tctgctgtgg gaaccgggtg aagcatttga tctgattctg    840
ggtaatccgc cttatggtat tgttggtgaa gcaagcaaat atccgatcca tgtttttaaa    900
gccgtgaaag atctgtacaa aaaagccttt agcacctgga aaggcaaata taacctgtat    960
ggtgcctttc tggaaaaagc agttcgtctg ctgaaaccgg gtggtgttct ggttttgtt   1020
```

```
gttccggcaa cctggctggt gctggaagat tttgcactgc tgcgtgaatt tctggcacgt    1080
gaaggtaaaa ccagcgttta ttatctgggt gaagtttttc cgcagaaaaa agttagcgca    1140
gtggttattc gttttcagaa aagcggtaaa ggtctgagcc tgtgggatac ccaagaaagc    1200
gaaagcggtt ttaccccgat tctgtgggct gaatatccgc attgggaagg tgaaattatt    1260
cgctttgaaa ccgaagaaac ccgcaaactg gaaatttcag gtatgccgct gggtgacctg    1320
tttcatatcc gttttgcagc acgtagtccg gaattcaaaa acatccggc agttcgtaaa    1380 gaaccgggtc cgggtctggt tccggttctg accggtcgta atctgaaacc tggttgggtt    1440
gattatgaaa aaaatcatag cggtctgtgg atgccgaaag aacgtgcaaa agaactgcgt    1500
gatttttatg caacaccgca tctggttgtt gcacatacca aaggcacccg tgttgttgca    1560
gcatgggatg aacgtgcata tccgtggcgt gaagaatttc atctgctgcc taaagaaggt    1620
gttcgtctgg atccgagcag cctggttcag tggctgaata gcgaagcaat gcagaaacat    1680
gttcgtaccc tgtatcgtga ttttgttccg catctgaccc tgcgtatgct ggaacgtctg    1740
ccggttcgtc gtgaatatgg ttttcatacc agtccgaaaa gcgcacgtaa cttttaacaa    1800
agcccgaaag gaagctgagt tggctgctgc caccgctgag caataactag cataacccct    1860
tggggcctct aaacgggtct tgaggggttt tttgctgaaa ggaggccact cgagcaccta    1920
ggag                                                                1924

<210> SEQ ID NO 273
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (19)..(38)
<223> OTHER INFORMATION: n can be any nucleotide

<400> SEQUENCE: 273
acatgcagct cttccaccnn nnnnnnnnnn nnnnnnnn                              38

<210> SEQ ID NO 274
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (19)..(38)
<223> OTHER INFORMATION: n can be any nucleotide

<400> SEQUENCE: 274
cgaggaagct cttccatcnn nnnnnnnnnn nnnnnnnn                              38
```